(12) United States Patent
Idelevich et al.

(10) Patent No.: US 9,182,403 B2
(45) Date of Patent: Nov. 10, 2015

(54) KITS FOR AND METHODS OF DIFFERENTIAL STAINING OF CERVICAL CANCER CELLS AND/OR TISSUES

(75) Inventors: Pavel Idelevich, Rechovot (IL); Adi Elkeles, Tel-Mond (IL); Dov Terkieltaub, Givat Shmuel (IL); Ami Eyal, Maccabim-Reut (IL)

(73) Assignee: Zetiq Technologies LTD. (IL)

( * ) Notice: Subject to any disclaimer, the term of this patent is extended or adjusted under 35 U.S.C. 154(b) by 0 days.

(21) Appl. No.: 13/320,558

(22) PCT Filed: May 17, 2010

(86) PCT No.: PCT/IL2010/000399
§ 371 (c)(1),
(2), (4) Date: Nov. 15, 2011

(87) PCT Pub. No.: WO2010/134073
PCT Pub. Date: Nov. 25, 2010

(65) Prior Publication Data
US 2012/0064526 A1   Mar. 15, 2012

Related U.S. Application Data

(60) Provisional application No. 61/213,228, filed on May 19, 2009.

(51) Int. Cl.
*G01N 33/574* (2006.01)

(52) U.S. Cl.
CPC ................................ *G01N 33/57411* (2013.01)

(58) Field of Classification Search
None
See application file for complete search history.

(56) References Cited

U.S. PATENT DOCUMENTS

| | | | |
|---|---|---|---|
| 3,791,932 A | 2/1974 | Schuurs | |
| 3,839,153 A | 10/1974 | Schuurs | |
| 3,850,578 A | 11/1974 | McConnell | |
| 3,850,752 A | 11/1974 | Schuurs | |
| 3,853,987 A | 12/1974 | Dreyer | |
| 3,867,517 A | 2/1975 | Ling | |
| 3,879,262 A | 4/1975 | Schuurs | |
| 3,901,654 A | 8/1975 | Gross | |
| 3,935,074 A | 1/1976 | Rubenstein | |
| 3,984,533 A | 10/1976 | Uzgiris | |
| 3,996,345 A | 12/1976 | Ullman | |
| 4,034,074 A | 7/1977 | Miles | |
| 4,036,945 A | 7/1977 | Haber | |
| 4,098,876 A | 7/1978 | Piasio | |
| 4,331,647 A | 5/1982 | Goldenberg | |
| 4,666,828 A | 5/1987 | Gusella | |
| 4,683,202 A | 7/1987 | Mullis | |
| 4,698,360 A | 10/1987 | Masquelier | |
| 4,801,531 A | 1/1989 | Frossard | |
| 4,879,219 A | 11/1989 | Wands | |
| 4,946,778 A | 8/1990 | Ladner | |
| 5,011,771 A | 4/1991 | Bellet | |
| 5,192,659 A | 3/1993 | Simons | |
| 5,272,057 A | 12/1993 | Smulson | |
| 5,281,521 A | 1/1994 | Trojanowski | |
| 6,051,393 A | 4/2000 | Jones et al. | |
| 6,284,543 B1 * | 9/2001 | Alvarez | 436/64 |
| 8,012,678 B2 * | 9/2011 | Pyeon et al. | 435/4 |
| 2002/0058028 A1 | 5/2002 | Malmros | |
| 2004/0260157 A1 * | 12/2004 | Montes | 600/301 |
| 2005/0181429 A1 | 8/2005 | Fejgin | |
| 2009/0117610 A1 | 5/2009 | Gelvan et al. | |
| 2009/0221430 A1 * | 9/2009 | Wu et al. | 506/7 |
| 2011/0318756 A1 | 12/2011 | Tsivis | |
| 2013/0102025 A1 | 4/2013 | Davis | |

FOREIGN PATENT DOCUMENTS

| | | | |
|---|---|---|---|
| CN | 1854709 A | 11/2006 | |
| CN | 1967196 A | 5/2007 | |
| WO | 96/16334 | 5/1996 | |
| WO | 03/091729 | 11/2003 | |
| WO | 2004/086937 | 10/2004 | |
| WO | 2007/015926 | 2/2007 | |
| WO | WO 2007/102146 | * 9/2007 | C12N 15/82 |
| WO | 2009/055052 | 4/2009 | |

OTHER PUBLICATIONS

Fukuda et al, Histochem, 1980, 65:269-276.*
Dilek et al, Exp J Obstet Gynecol, 1998, 79:149-151.*
Zhu et al, Oncol Rep, 2007, 18:157-160.*
Scimia, Adv Clin Pathol, 2001, 5:183-184.*
Trunk et al, Acta Cytologica, 2004, 48:771-782.*
Achilonu et al., (2008) Synthesis of proanthocyanidins. Part 1. The first oxidative formation of the interflavanyl bond in procyanidins. Organic Letters 10(17): 3865-3868.
Anantaraman and Ravindranath (1976) Histochemical characteristics of the egg envelopes of Acanthosentis sp. (*Acanthocephala*). Z Parasitenkd. Feb. 6, 1976;48(3-4): 227-38.
Desmedt et al., (2009) Quantitation of HER2 expression or HER2:HER2 dimers and differential survival in a cohort of metastatic breast cancer patients carefully selected for trastuzumab treatment primarily by FISH. Diag Mol Pathol 18 (1): 22-29—Abstract.
Idelevich et al., (2009) Novel Histochemical Stain for Tinctorial Detection of Cancer and Neoplastic Cells. The Journal of Histotechnology 32(3): 97-105.

(Continued)

*Primary Examiner* — Mark Halvorson
(74) *Attorney, Agent, or Firm* — Whitmyer IP Group LLC

(57) ABSTRACT

Provided are methods and kits for staining cervical cell sample by contacting the cervical cell sample with a *Ficus elastics* plant extract, staining the cervical cell sample with New Fuchsin, and staining the cervical cell sample with Light Green or Fast Green. Also provided are method of diagnosing a pre-malignant or a malignant cervical tumor in a subject, by staining the cervical cell sample and identifying at least one cervical cell having a red cytoplasm above a pre-determined threshold, wherein presence of the at least one cervical cell having the red cytoplasm above the pre-determined threshold is indicative of a non- or less-differentiated cell as compared to a normal cervical cell, thereby diagnosing the pre-malignant or a malignant cervical tumor in the subject.

13 Claims, 28 Drawing Sheets
(28 of 28 Drawing Sheet(s) Filed in Color)

(56) References Cited

OTHER PUBLICATIONS

Komen et al., (2008) Viability analysis and apoptosis induction of breast cancer cells in a microfluidic device: effect of cytostatic drugs. Biomed Microdevices 10(5): 727-737.

Kortekangas-Savolainen et al., (2006) Allergens of *Ficus Benjamina* (*weeping fig*):Unique allergens in sap. Allergy 61 (3): 393-394.

Molnar and Mehes (2009) Predictive molecular pathological testing in the diagnosis of high-grade tumors of glial origin. Magyer Oncologia 53(1):33-38—Abstract.

Sackeyfio et al., (1986) The anti-inflammatory effect of a crude aqueous extract of the root bark of *Ficus-Elastica* in the rat. Archives Internationales de Pharmacodynamie et de Therapie 281(1): 169-176.

Shao et al., (2003) Grape seed proanthocyanidin extract attenuates oxidant injury in cardiomyocytes. Pharmacological Research 47: 463-469.

Steven et al., (1996) Fluorescent location of cells of cytological interest in cervical smears prestained with thionin. Anticancer Res 16(3A):1193-1196.

Ye et al., (1999) The cytotoxic effects of a novel IH636 grape seed proanthocyanidin extract on cultured human cancer cells. Mol Cell Biochem 196(1-2): 99-108.

Duesbery et al., (2001) Suppression of ras-mediated transformation and inhibition of tumor growth and angiogenesis by anthrax lethal factor, a proteolytic inhibitor of multiple MEK pathways. Proc Natl Acad Sci U S A 98(7): 4089-94.

Hamburger and Hamilton (1951) A series of normal stages in the development of the chick embryo. J Morphol 88(1): 49-92.

Klein et al., (2005) Transitional cell hyperplasia and carcinomas in urinary bladders of transgenic mice with keratin 5 promoter-driven cyclooxygenase-2 overexpression. Cancer Res 65(5): 1808-1813.

Papanicolaou and Traut (1941) The diagnostic value of vaginal smears in carcinoma of the uterus. Am J Obstet Gynecol 42: 193-206.

Proctor et al., (2010) Biomarkers in bladder cancer. Histopathology 57(1): 1-13.

Scholzen and Gerdes (2000) The Ki-67 protein: from the known and the unknown. J Cell Physiol 182(3): 311-322.

Giovanni et al., (2003) ThinPrep versus conventional Papanicolaou smear in the cytologic follow-up of women with equivocal cervical smears. Cancer 99(6): 342-345.

Nifli et al., (2005) Monomeric and oligomeric flavanols are agonists of membrane androgen receptors. Exp Cell Res 309(2): 329-339.

Zhang et al., (2005) Proanthocyanidin from grape seeds potentiates anti-tumor activity of doxorubicin via immunomodulatory mechanism. Int Immunopharmacol 5(7-8): 1247-1257.

Pan et al., (2001) Comparative study on liquid-based cytology for cervical carcinoma screening in a higlr risk area of China. Chinese Journal of Oncology 23(4): 309-321. Translated abstract.

Gong et al., (2002) Composite staining method of displaying mucin, elastin and collagen and the application thereof. Chinese Journal of Histochemistry and Cytochemistry 11(4): 503-504. English translation.

Coste et al., (2003) Cross sectional study of conventional cervical smear, monolayer cytology, and human papillomavirus DNA testing for cervical cancer screening. BMJ 326(7392): 733.

Arbyn et al., (2008) Liquid compared with conventional cervical cytology: a systematic review and meta-analysis. Obstet Gynecol 111(1): 167-77.

\* cited by examiner

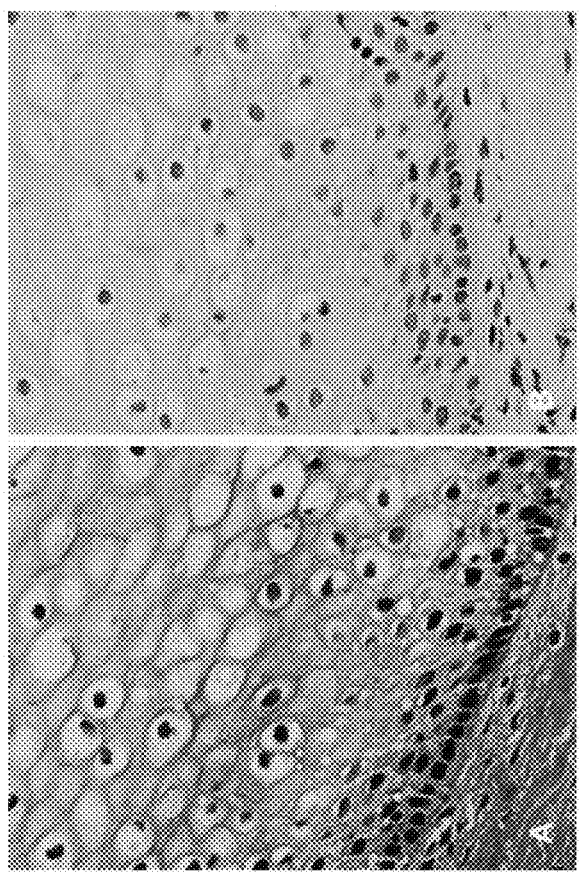

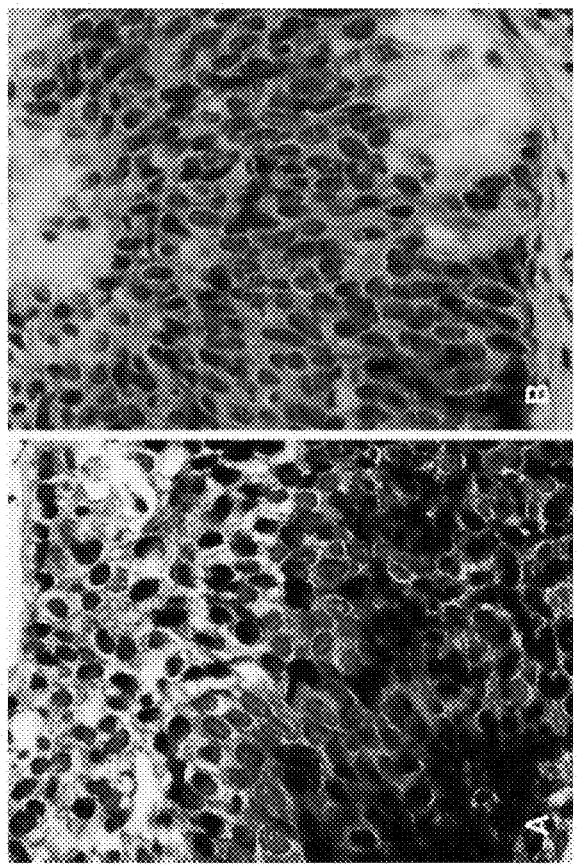

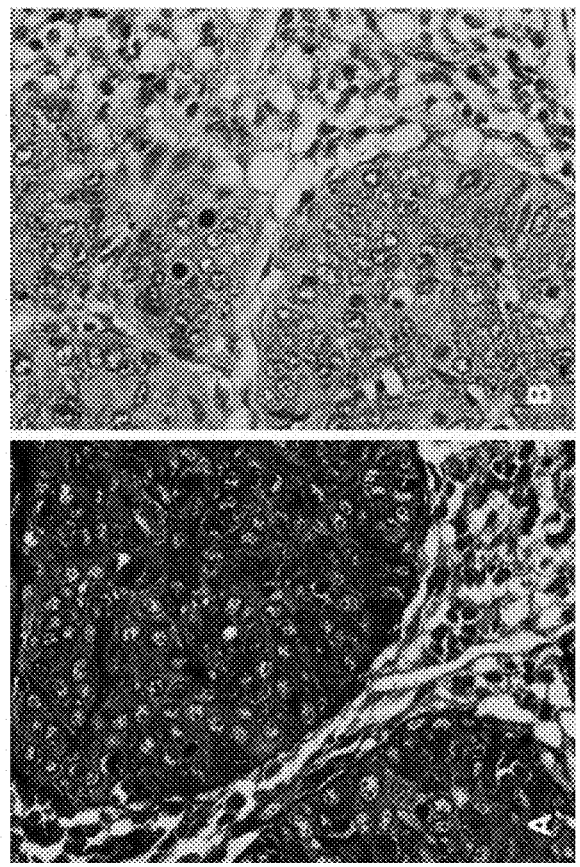

x4

Staining method of the invention x20
Pap staining

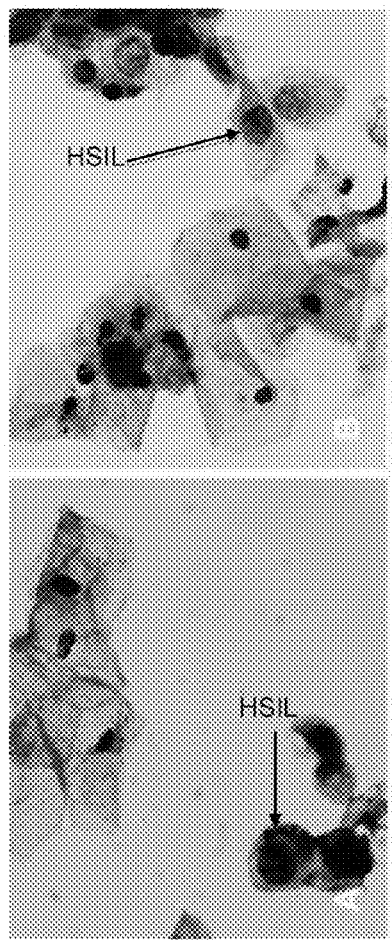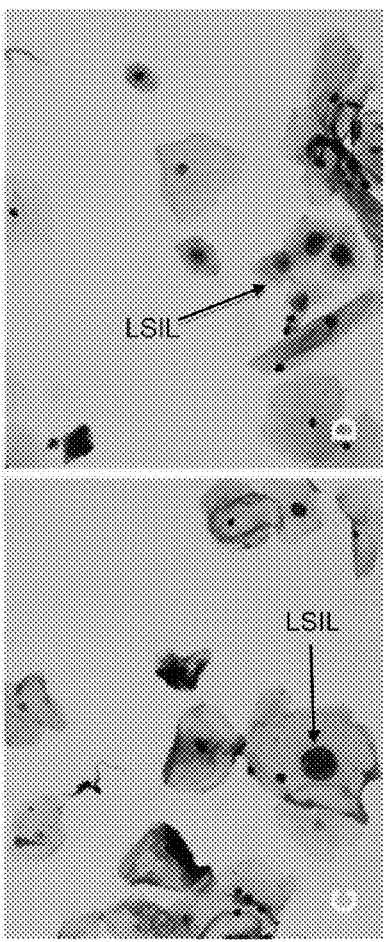

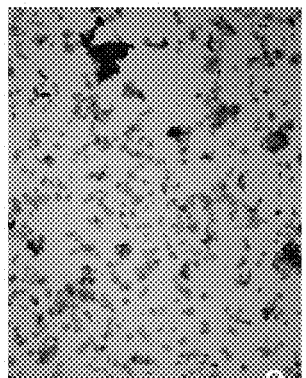
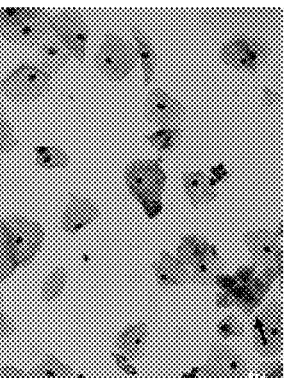
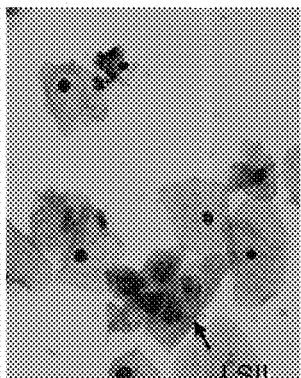
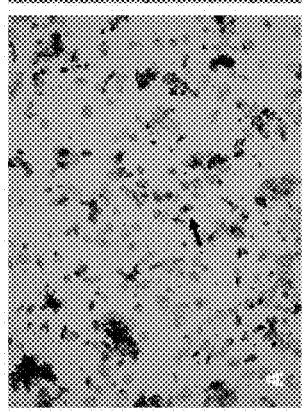
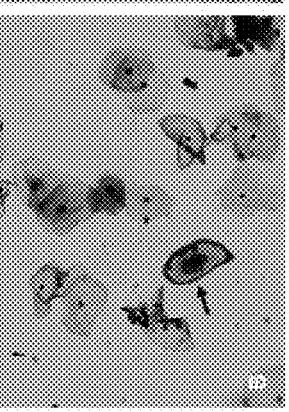
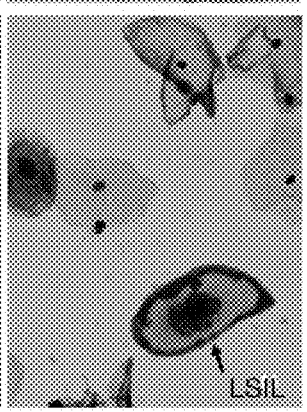
FIG. 7D  FIG. 7E  FIG. 7F
FIG. 7A  FIG. 7B  FIG. 7C

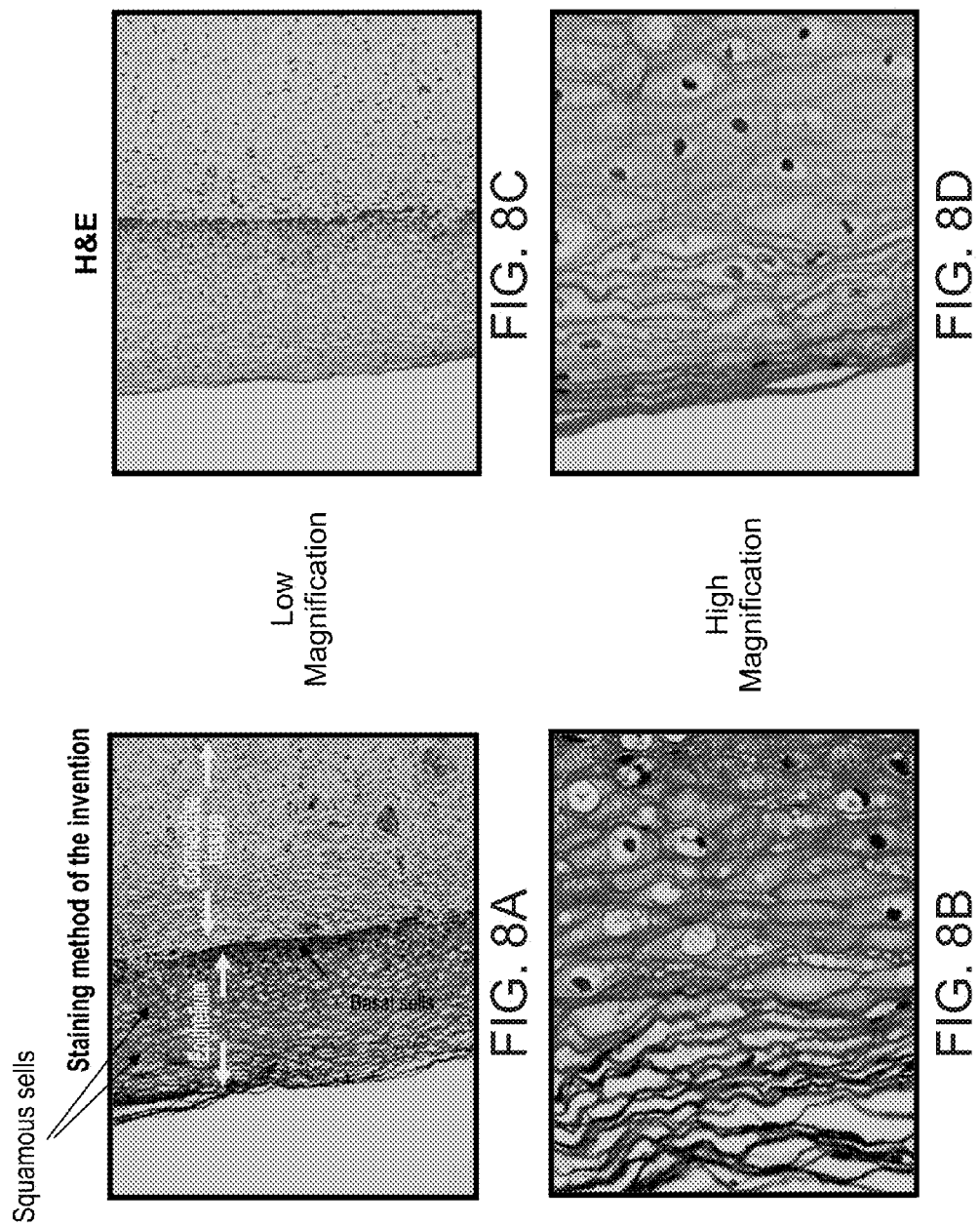

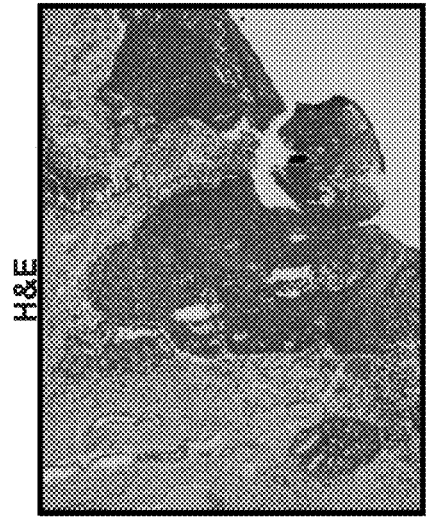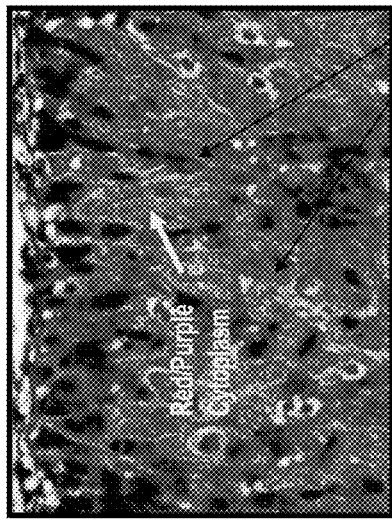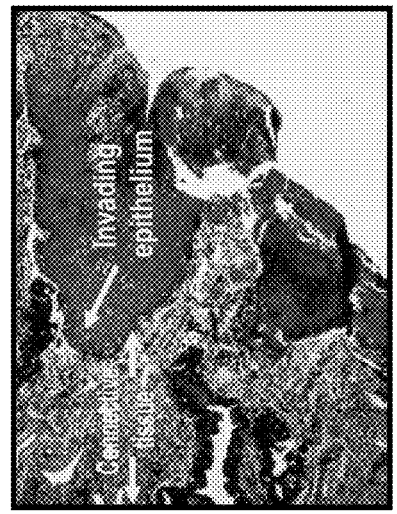

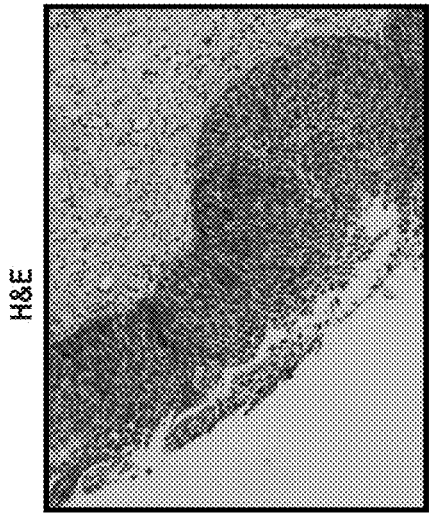
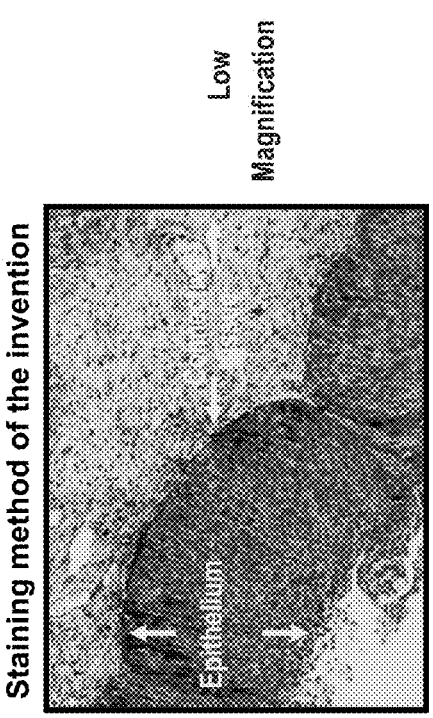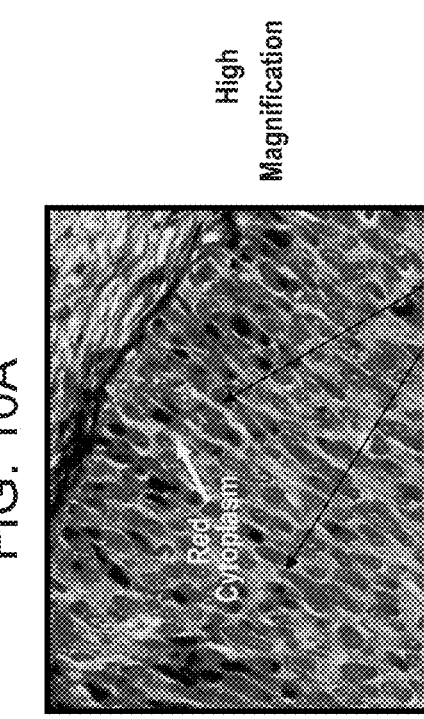
FIG. 10A  FIG. 10B  FIG. 10C  FIG. 10D

FIG. 16 — Squamous cell carcinoma cells

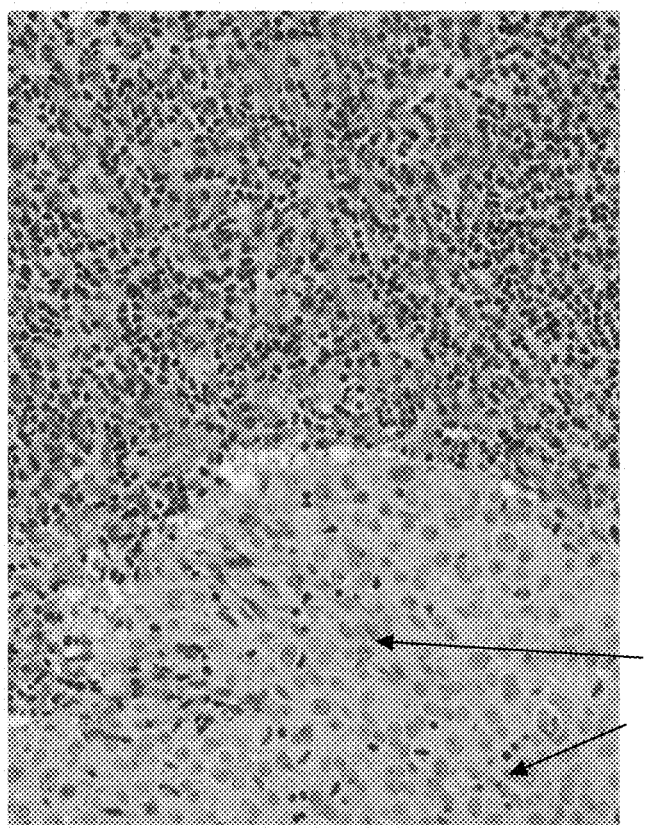
FIG. 29 — Non-keratinizing squamous carcinoma cells

SEQUENCE LISTING

<160> NUMBER OF SEQ ID NOS: 30

<210> SEQ ID NO 1
<211> LENGTH: 4082
<212> TYPE: DNA
<213> ORGANISM: Homo sapiens

<400> SEQUENCE: 1

| | | | | | | |
|---|---|---|---|---|---|---|
| gcgcgcgccg | gcctgggcag | gcgagcgggc | gcgctcccgc | cccctctccc | ctccccgcgc | 60 |
| gcccgagcgc | gcctccgccc | ttgcccgccc | cctgacgctg | cctcagctcc | tcagtgcaca | 120 |
| gtgctgcctc | gtctgagggg | acaggaggat | caccctcttc | gtcgcttcgg | ccagtgtgtc | 180 |
| gggctgggcc | ctgacaagcc | acctgaggag | aggctcggag | ccgggcccgg | accccggcga | 240 |
| ttgccgcccg | cttctctcta | gtctcacgag | gggtttcccg | cctcgcaccc | ccacctctgg | 300 |
| acttgccttt | ccttctcttc | tccgcgtgtg | gagggagcca | gcgcttaggc | cggagcgagc | 360 |
| ctgggggccc | cccgccgtga | agacatcgcg | ggaccgatt | caccatggag | ggcgccggcg | 420 |
| gcgcgaacga | caagaaaaag | ataagttctg | aacgtcgaaa | agaaaagtct | cgagatgcag | 480 |
| ccagatctcg | gcgaagtaaa | gaatctgaag | ttttttatga | gcttgctcat | cagttgccac | 540 |
| ttccacataa | tgtgagttcg | catcttgata | aggcctctgt | gatgaggctt | accatcagct | 600 |
| atttgcgtgt | gaggaaactt | ctggatgctg | gtgatttgga | tattgaagat | gacatgaaag | 660 |
| cacagatgaa | ttgcttttat | ttgaaagcct | tggatggttt | tgttatggtt | ctcacagatg | 720 |
| atggtgacat | gatttacatt | tctgataatg | tgaacaaata | catgggatta | actcagtttg | 780 |
| aactaactgg | acacagtgtg | tttgatttta | ctcatccatg | tgaccatgag | gaaatgagag | 840 |
| aaatgcttac | acacagaaat | ggccttgtga | aaaagggtaa | agaacaaaac | acacagcgaa | 900 |
| gcttttttct | cagaatgaag | tgtaccctaa | ctagccgagg | aagaactatg | aacataaagt | 960 |
| ctgcaacatg | gaaggtattg | cactgcacag | gccacattca | cgtatatgat | accaacagta | 1020 |
| accaacctca | gtgtgggtat | aagaaaccac | ctatgacctg | cttggtgctg | atttgtgaac | 1080 |
| ccattcctca | cccatcaaat | attgaaattc | ctttagatag | caagactttc | ctcagtcgac | 1140 |
| acagcctgga | tatgaaattt | tcttattgtg | atgaaagaat | taccgaattg | atgggatatg | 1200 |
| agccagaaga | acttttaggc | cgctcaattt | atgaatatta | tcatgctttg | gactctgatc | 1260 |
| atctgaccaa | aactcatcat | gatatgttta | ctaaaggaca | agtcaccaca | ggacagtaca | 1320 |
| ggatgcttgc | caaaagaggt | ggatatgtct | gggttgaaac | tcaagcaact | gtcatatata | 1380 |
| acaccaagaa | ttctcaacca | cagtgcattg | tatgtgtgaa | ttacgttgtg | agtggtatta | 1440 |
| ttcagcacga | cttgattttc | tcccttcaac | aaacagaatg | tgtccttaaa | ccggttgaat | 1500 |
| cttcagatat | gaaaatgact | cagctattca | ccaaagttga | atcagaagat | acaagtagcc | 1560 |
| tctttgacaa | acttaagaag | gaacctgatg | ctttaacttt | gctggcccca | gccgctggag | 1620 |
| acacaatcat | atctttagat | tttggcagca | acgacacaga | aactgatgac | cagcaacttg | 1680 |
| aggaagtacc | attatataat | gatgtaatgc | tcccctcacc | caacgaaaaa | ttacagaata | 1740 |
| taaatttggc | aatgtctcca | ttacccaccg | ctgaaacgcc | aaagccactt | cgaagtagtg | 1800 |
| ctgaccctgc | actcaatcaa | gaagttgcat | taaaattaga | accaaatcca | gagtcactgg | 1860 |
| aactttcttt | taccatgccc | cagattcagg | atcagacacc | tagtccttcc | gatggaagca | 1920 |
| ctagacaaag | ttcacctgag | cctaatagtc | ccagtgaata | ttgtttttat | gtggatagtg | 1980 |
| atatggtcaa | tgaattcaag | ttggaattgg | tagaaaaact | ttttgctgaa | gacacagaag | 2040 |
| caaagaaccc | attttctact | caggacacag | atttagactt | ggagatgtta | gctccctata | 2100 |

-continued

| | |
|---|---|
| tcccaatgga tgatgacttc cagttacgtt ccttcgatca gttgtcacca ttagaaagca | 2160 |
| gttccgcaag ccctgaaagc gcaagtcctc aaagcacagt tacagtattc cagcagactc | 2220 |
| aaatacaaga acctactgct aatgccacca ctaccactgc caccactgat gaattaaaaa | 2280 |
| cagtgacaaa agaccgtatg gaagacatta aaatattgat tgcatctcca tctcctaccc | 2340 |
| acatacataa agaaactact agtgccacat catcaccata tagagatact caaagtcgga | 2400 |
| cagcctcacc aaacagagca ggaaaaggag tcatagaaca gacagaaaaa tctcatccaa | 2460 |
| gaagccctaa cgtgttatct gtcgctttga gtcaaagaac tacagttcct gaggaagaac | 2520 |
| taaatccaaa gatactagct ttgcagaatg ctcagaaaa gcgaaaaatg aacatgatg | 2580 |
| gttcactttt tcaagcagta ggaattggaa cattattaca gcagccagac gatcatgcag | 2640 |
| ctactacatc actttcttgg aaacgtgtaa aaggatgcaa atctagtgaa cagaatggaa | 2700 |
| tggagcaaaa gacaattatt ttaataccct ctgatttagc atgtagactg ctggggcaat | 2760 |
| caatggatga aagtggatta ccacagctga ccagttatga ttgtgaagtt aatgctccta | 2820 |
| tacaaggcag cagaaaccta ctgcagggtg aagaattact cagagctttg gatcaagtta | 2880 |
| actgagcttt tcttaatttt cattcctttt tttggacact ggtggctcat tacctaaagc | 2940 |
| agtctattta tattttctac atctaatttt agaagcctgg ctacaatact gcacaaactt | 3000 |
| ggttagttca attttgatcc ccttttctact aatttacat taatgctctt ttttagtatg | 3060 |
| ttctttaatg ctggatcaca gacagctcat tttctcagtt ttttggtatt taaaccattg | 3120 |
| cattgcagta gcatcatttt aaaaaatgca ccttttttatt tattttatttt tggctaggga | 3180 |
| gtttatccct ttttcgaatt attttttaaga agatgccaat ataattttg taagaaggca | 3240 |
| gtaacctttc atcatgatca taggcagttg aaaaattttt acaccttttt tttcacattt | 3300 |
| tacataaata ataatgcttt gccagcagta cgtggtagcc acaattgcac aatatatttt | 3360 |
| cttaaaaaat accagcagtt actcatggaa tatattctgc gtttataaaa ctagttttta | 3420 |
| agaagaaatt ttttttggcc tatgaaattg ttaaacctgg aacatgacat tgttaatcat | 3480 |
| ataataatga ttcttaaatg ctgtatggtt tattatttaa atgggtaaag ccatttacat | 3540 |
| aatatagaaa gatatgcata tatctagaag gtatgtggca tttatttgga taaaattctc | 3600 |
| aattcagaga aatcatctga tgtttctata gtcactttgc cagctcaaaa gaaaacaata | 3660 |
| ccctatgtag ttgtggaagt ttatgctaat attgtgtaac tgatattaaa cctaaatgtt | 3720 |
| ctgcctaccc tgttggtata aagatatttt gagcagactg taaacaagaa aaaaaaatc | 3780 |
| atgcattctt agcaaaattg cctagtatgt taatttgctc aaaatacaat gtttgatttt | 3840 |
| atgcactttg tcgctattaa catccttttt ttcatgtaga tttcaataat tgagtaattt | 3900 |
| tagaagcatt attttaggaa tatatagttg tcacagtaaa tatcttgttt tttctatgta | 3960 |
| cattgtacaa attttcatt cctttttgctc tttgtggttg gatctaacac taactgtatt | 4020 |
| gttttgttac atcaaataaa catcttctgt ggaccaggca aaaaaaaaa aaaaaaaaa | 4080 |
| aa | 4082 |

<210> SEQ ID NO 2
<211> LENGTH: 826
<212> TYPE: PRT
<213> ORGANISM: Homo sapiens

<400> SEQUENCE: 2

Met Glu Gly Ala Gly Gly Ala Asn Asp Lys Lys Lys Ile Ser Ser Glu
1               5                   10                  15

-continued

Arg Arg Lys Glu Lys Ser Arg Asp Ala Ala Arg Ser Arg Arg Ser Lys
            20                  25                  30

Glu Ser Glu Val Phe Tyr Glu Leu Ala His Gln Leu Pro Leu Pro His
            35                  40                  45

Asn Val Ser Ser His Leu Asp Lys Ala Ser Val Met Arg Leu Thr Ile
 50                  55                  60

Ser Tyr Leu Arg Val Arg Lys Leu Leu Asp Ala Gly Asp Leu Asp Ile
 65                  70                  75                  80

Glu Asp Asp Met Lys Ala Gln Met Asn Cys Phe Tyr Leu Lys Ala Leu
                85                  90                  95

Asp Gly Phe Val Met Val Leu Thr Asp Gly Asp Met Ile Tyr Ile
            100                 105                 110

Ser Asp Asn Val Asn Lys Tyr Met Gly Leu Thr Gln Phe Glu Leu Thr
            115                 120                 125

Gly His Ser Val Phe Asp Phe Thr His Pro Cys Asp His Glu Glu Met
 130                 135                 140

Arg Glu Met Leu Thr His Arg Asn Gly Leu Val Lys Lys Gly Lys Glu
145                 150                 155                 160

Gln Asn Thr Gln Arg Ser Phe Phe Leu Arg Met Lys Cys Thr Leu Thr
            165                 170                 175

Ser Arg Gly Arg Thr Met Asn Ile Lys Ser Ala Thr Trp Lys Val Leu
            180                 185                 190

His Cys Thr Gly His Ile His Val Tyr Asp Thr Asn Ser Asn Gln Pro
            195                 200                 205

Gln Cys Gly Tyr Lys Lys Pro Pro Met Thr Cys Leu Val Leu Ile Cys
210                 215                 220

Glu Pro Ile Pro His Pro Ser Asn Ile Glu Ile Pro Leu Asp Ser Lys
225                 230                 235                 240

Thr Phe Leu Ser Arg His Ser Leu Asp Met Lys Phe Ser Tyr Cys Asp
            245                 250                 255

Glu Arg Ile Thr Glu Leu Met Gly Tyr Glu Pro Glu Glu Leu Leu Gly
            260                 265                 270

Arg Ser Ile Tyr Glu Tyr Tyr His Ala Leu Asp Ser Asp His Leu Thr
            275                 280                 285

Lys Thr His His Asp Met Phe Thr Lys Gly Gln Val Thr Thr Gly Gln
            290                 295                 300

Tyr Arg Met Leu Ala Lys Arg Gly Gly Tyr Val Trp Val Glu Thr Gln
305                 310                 315                 320

Ala Thr Val Ile Tyr Asn Thr Lys Asn Ser Gln Pro Gln Cys Ile Val
            325                 330                 335

Cys Val Asn Tyr Val Val Ser Gly Ile Ile Gln His Asp Leu Ile Phe
            340                 345                 350

Ser Leu Gln Gln Thr Glu Cys Val Leu Lys Pro Val Glu Ser Ser Asp
            355                 360                 365

Met Lys Met Thr Gln Leu Phe Thr Lys Val Glu Ser Glu Asp Thr Ser
            370                 375                 380

Ser Leu Phe Asp Lys Leu Lys Lys Glu Pro Asp Ala Leu Thr Leu Leu
385                 390                 395                 400

Ala Pro Ala Ala Gly Asp Thr Ile Ile Ser Leu Asp Phe Gly Ser Asn
            405                 410                 415

Asp Thr Glu Thr Asp Asp Gln Gln Leu Glu Glu Val Pro Leu Tyr Asn
            420                 425                 430

```
Asp Val Met Leu Pro Ser Pro Asn Glu Lys Leu Gln Asn Ile Asn Leu
            435                 440                 445

Ala Met Ser Pro Leu Pro Thr Ala Glu Thr Pro Lys Pro Leu Arg Ser
450                 455                 460

Ser Ala Asp Pro Ala Leu Asn Gln Glu Val Ala Leu Lys Leu Glu Pro
465                 470                 475                 480

Asn Pro Glu Ser Leu Glu Leu Ser Phe Thr Met Pro Gln Ile Gln Asp
                485                 490                 495

Gln Thr Pro Ser Pro Ser Asp Gly Ser Thr Arg Gln Ser Ser Pro Glu
            500                 505                 510

Pro Asn Ser Pro Ser Glu Tyr Cys Phe Tyr Val Asp Ser Asp Met Val
            515                 520                 525

Asn Glu Phe Lys Leu Glu Leu Val Glu Lys Leu Phe Ala Glu Asp Thr
            530                 535                 540

Glu Ala Lys Asn Pro Phe Ser Thr Gln Asp Thr Asp Leu Asp Leu Glu
545                 550                 555                 560

Met Leu Ala Pro Tyr Ile Pro Met Asp Asp Asp Phe Gln Leu Arg Ser
                565                 570                 575

Phe Asp Gln Leu Ser Pro Leu Glu Ser Ser Ser Ala Ser Pro Glu Ser
            580                 585                 590

Ala Ser Pro Gln Ser Thr Val Thr Val Phe Gln Gln Thr Gln Ile Gln
            595                 600                 605

Glu Pro Thr Ala Asn Ala Thr Thr Thr Thr Ala Thr Thr Asp Glu Leu
            610                 615                 620

Lys Thr Val Thr Lys Asp Arg Met Glu Asp Ile Lys Ile Leu Ile Ala
625                 630                 635                 640

Ser Pro Ser Pro Thr His Ile His Lys Glu Thr Thr Ser Ala Thr Ser
                645                 650                 655

Ser Pro Tyr Arg Asp Thr Gln Ser Arg Thr Ala Ser Pro Asn Arg Ala
            660                 665                 670

Gly Lys Gly Val Ile Glu Gln Thr Glu Lys Ser His Pro Arg Ser Pro
            675                 680                 685

Asn Val Leu Ser Val Ala Leu Ser Gln Arg Thr Thr Val Pro Glu Glu
            690                 695                 700

Glu Leu Asn Pro Lys Ile Leu Ala Leu Gln Asn Ala Gln Arg Lys Arg
705                 710                 715                 720

Lys Met Glu His Asp Gly Ser Leu Phe Gln Ala Val Gly Ile Gly Thr
                725                 730                 735

Leu Leu Gln Gln Pro Asp Asp His Ala Ala Thr Thr Ser Leu Ser Trp
            740                 745                 750

Lys Arg Val Lys Gly Cys Lys Ser Ser Glu Gln Asn Gly Met Glu Gln
            755                 760                 765

Lys Thr Ile Ile Leu Ile Pro Ser Asp Leu Ala Cys Arg Leu Leu Gly
770                 775                 780

Gln Ser Met Asp Glu Ser Gly Leu Pro Gln Leu Thr Ser Tyr Asp Cys
785                 790                 795                 800

Glu Val Asn Ala Pro Ile Gln Gly Ser Arg Asn Leu Leu Gln Gly Glu
                805                 810                 815

Glu Leu Leu Arg Ala Leu Asp Gln Val Asn
            820                 825

<210> SEQ ID NO 3
<211> LENGTH: 1234
<212> TYPE: DNA
```

<213> ORGANISM: Homo sapiens

<400> SEQUENCE: 3

```
attccacgtt cttaactgtt ccattttccg tatctgcttc gggcttccac ctcattttt    60
tcgctttgcc cattctgttt cagccagtcg ccaagaatca tgaaagtcgc cagtggcagc   120
accgccaccg ccgccgcggg ccccagctgc gcgctgaagg ccggcaagac agcgagcggt   180
gcgggcgagg tggtgcgctg tctgtctgag cagagcgtgg ccatctcgcg ctgcgccggg   240
ggcgccgggg cgcgcctgcc tgccctgctg gacgagcagc aggtaaacgt gctgctctac   300
gacatgaacg ctgttactc acgcctcaag gagctggtgc ccaccctgcc ccagaaccgc    360
aaggtgagca aggtggagat ctccagcac gtcatcgact acatcaggga ccttcagttg    420
gagctgaact cggaatccga agttggaacc cccgggggcc gagggctgcc ggtccgggct   480
ccgctcagca ccctcaacgg cgagatcagc gccctgacgg ccgaggtgag atccagatcc   540
gaccactaga tcatccttat accgacgggg aaacggaggc cagagagggc gtgggcgctt   600
gcaccacttc cgtcccatcc ttgcgggtac ctggctatgc gggggtgcct aaggagcctg   660
gaaaaagcgc tcccccgtcg tgcttcctgg ggaaggggc gttcgctgcg ctcggagcgg    720
cgtcccttcc aacccgccgg tctcattcct tctcgttttc acaggcggca tgcgttcctg   780
cggacgatcg catcttgtgt cgctgaagcg cctcccccag ggaccggcgg accccagcca   840
tccaggggc aagaggaatt acgtgctctg tgggtctccc ccaacgcgcc tcgccggatc    900
tgagggagaa caagaccgat cggcggccac tgcgccctta actgcatcca gcctgggct    960
gaggctgagg cactggcgag gagagggcgc tcctctctgc acacctacta gtcaccagag   1020
actttagggg gtgggattcc actcgtgtgt ttctattttt tgaaaagcag acattttaaa   1080
aaatggtcac gtttggtgct tctcagattt ctgaggaaat tgctttgtat tgtatattac   1140
aatgatcacc gactgaaaat attgttttac aatagttctg tggggctgtt ttttgttat    1200
taaacaaata atttagatgg tgaaaaaaaa aaaa                              1234
```

<210> SEQ ID NO 4
<211> LENGTH: 149
<212> TYPE: PRT
<213> ORGANISM: Homo sapiens

<400> SEQUENCE: 4

```
Met Lys Val Ala Ser Gly Ser Thr Ala Thr Ala Ala Gly Pro Ser
1               5                   10                  15

Cys Ala Leu Lys Ala Gly Lys Thr Ala Ser Gly Ala Gly Glu Val Val
            20                  25                  30

Arg Cys Leu Ser Glu Gln Ser Val Ala Ile Ser Arg Cys Ala Gly Gly
        35                  40                  45

Ala Gly Ala Arg Leu Pro Ala Leu Leu Asp Glu Gln Gln Val Asn Val
    50                  55                  60

Leu Leu Tyr Asp Met Asn Gly Cys Tyr Ser Arg Leu Lys Glu Leu Val
65                  70                  75                  80

Pro Thr Leu Pro Gln Asn Arg Lys Val Ser Lys Val Glu Ile Leu Gln
                85                  90                  95

His Val Ile Asp Tyr Ile Arg Asp Leu Gln Leu Glu Leu Asn Ser Glu
            100                 105                 110

Ser Glu Val Gly Thr Pro Gly Gly Arg Gly Leu Pro Val Arg Ala Pro
        115                 120                 125

Leu Ser Thr Leu Asn Gly Glu Ile Ser Ala Leu Thr Ala Glu Val Arg
```

Ser Arg Ser Asp His
145

<210> SEQ ID NO 5
<211> LENGTH: 1163
<212> TYPE: DNA
<213> ORGANISM: Homo sapiens

<400> SEQUENCE: 5

| ctcctccgag cactcgctca cggcgtcccc ttgcctggaa agataccgcg gtccctccag | 60 |
| aggatttgag ggacagggtc ggaggggggct cttccgccag caccggagga agaaagagga | 120 |
| ggggctggct ggtcaccaga gggtggggcg gaccgcgtgc gctcggcggc tgcggagagg | 180 |
| gggagagcag gcagcgggcg gcggggagca gcatggagcc ggcggcgggg agcagcatgg | 240 |
| agccttcggc tgactggctg ccacggccg cggcccgggg tcgggtagag gaggtgcggg | 300 |
| cgctgctgga ggcgggggcg ctgcccaacg caccgaatag ttacggtcgg aggccgatcc | 360 |
| aggtcatgat gatgggcagc gcccgagtgg cggagctgct gctgctccac ggcgcggagc | 420 |
| ccaactgcgc cgaccccgcc actctcaccc gacccgtgca cgacgctgcc cgggagggct | 480 |
| tcctggacac gctggtggtg ctgcaccggg ccggggcgcg gctggacgtg cgcgatgcct | 540 |
| ggggccgtct gcccgtggac ctggctgagg agctgggcca tcgcgatgtc gcacggtacc | 600 |
| tgcgcgcggc tgcggggggc accagaggca gtaaccatgc ccgcatagat gccgcggaag | 660 |
| gtccctcaga catccccgat tgaaagaacc agagaggctc tgagaaacct cgggaaactt | 720 |
| agatcatcag tcaccgaagg tcctacaggg ccacaactgc cccgccaca acccaccccg | 780 |
| ctttcgtagt tttcatttag aaaatagagc ttttaaaaat gtcctgcctt ttaacgtaga | 840 |
| tatatgcctt cccccactac cgtaaatgtc catttatatc attttttata tattcttata | 900 |
| aaaatgtaaa aaagaaaaac accgcttctg cctttcact gtgttggagt tttctggagt | 960 |
| gagcactcac gccctaagcg cacattcatg tgggcatttc ttgcgagcct cgcagcctcc | 1020 |
| ggaagctgtc gacttcatga caagcatttt gtgaactagg gaagctcagg ggggttactg | 1080 |
| gcttctcttg agtcacactg ctagcaaatg gcagaaccaa agctcaaata aaaataaaat | 1140 |
| aattttcatt cattcactca aaa | 1163 |

<210> SEQ ID NO 6
<211> LENGTH: 156
<212> TYPE: PRT
<213> ORGANISM: Homo sapiens

<400> SEQUENCE: 6

Met Glu Pro Ala Ala Gly Ser Ser Met Glu Pro Ser Ala Asp Trp Leu
1               5                   10                  15

Ala Thr Ala Ala Ala Arg Gly Arg Val Glu Glu Val Arg Ala Leu Leu
            20                  25                  30

Glu Ala Gly Ala Leu Pro Asn Ala Pro Asn Ser Tyr Gly Arg Arg Pro
        35                  40                  45

Ile Gln Val Met Met Met Gly Ser Ala Arg Val Ala Glu Leu Leu Leu
    50                  55                  60

Leu His Gly Ala Glu Pro Asn Cys Ala Asp Pro Ala Thr Leu Thr Arg
65                  70                  75                  80

Pro Val His Asp Ala Ala Arg Glu Gly Phe Leu Asp Thr Leu Val Val
                85                  90                  95

```
Leu His Arg Ala Gly Ala Arg Leu Asp Val Arg Asp Ala Trp Gly Arg
            100                 105                 110
Leu Pro Val Asp Leu Ala Glu Glu Leu Gly His Arg Asp Val Ala Arg
        115                 120                 125
Tyr Leu Arg Ala Ala Ala Gly Gly Thr Arg Gly Ser Asn His Ala Arg
    130                 135                 140
Ile Asp Ala Ala Glu Gly Pro Ser Asp Ile Pro Asp
145                 150                 155

<210> SEQ ID NO 7
<211> LENGTH: 2168
<212> TYPE: DNA
<213> ORGANISM: Homo sapiens

<400> SEQUENCE: 7
gtatatcagg gccgcgctga gctgcgccag ctgaggtgtg agcagctgcc gaagtcagtt     60
ccttgtggag ccggagctgg gcgcggattc gccgaggcac cgaggcactc agaggaggcg    120
ccatgtcaga accggctggg gatgtccgtc agaacccatg cggcagcaag gcctgccgcc    180
gcctcttcgg cccagtggac agcgagcagc tgagccgcga ctgtgatgcg ctaatggcgg    240
gctgcatcca ggaggcccgt gagcgatgga acttcgactt tgtcaccgag acaccactgg    300
agggtgactt cgcctgggag cgtgtgcggg ccttggcct  gcccaagctc taccttccca    360
cggggccccg cgcaggccgg gatgagttgg gaggaggcag gcggcctggc acctcacctg    420
ctctgctgca ggggacagca gaggaagacc atgtggacct gtcactgtct tgtacccttg    480
tgcctcgctc aggggagcag gctgaagggt cccaggtgg  acctggagac tctcagggtc    540
gaaaacggcg gcagaccagc atgacagatt tctaccactc caaacgccgg ctgatcttct    600
ccaagaggaa gccctaatcc gcccacagga agcctgcagt cctggaagcg cgagggcctc    660
aaaggcccgc tctacatctt ctgccttagt ctcagtttgt gtgtcttaat tattatttgt    720
gttttaattt aaacacctcc tcatgtacat accctggccg ccccctgccc ccagcctct    780
ggcattagaa ttatttaaac aaaaactagg cggttgaatg agaggttcct aagagtgctg    840
ggcatttta  ttttatgaaa actatttaa  agcctcctca tcccgtgttc tccttttcct    900
ctctcccgga ggttgggtgg gccggcttca tgccagctac ttcctcctcc ccacttgtcc    960
gctgggtggt accctctgga ggggtgtggc tccttcccat cgctgtcaca ggcggttatg   1020
aaattcaccc cctttcctgg acactcagac ctgaattctt tttcatttga aagtaaaca   1080
gatggcactt tgaagggggcc tcaccgagtg ggggcatcat caaaaacttt ggagtccct   1140
cacctcctct aaggttgggc agggtgaccc tgaagtgagc acagcctagg gctgagctgg   1200
ggacctggta ccctcctggc tcttgatacc ccctctgtc ttgtgaaggc agggggaagg   1260
tggggtcctg gagcagacca ccccgcctgc cctcatggcc cctctgacct gcactgggga   1320
gcccgtctca gtgttgagcc ttttccctct ttggctcccc tgtacctttt gaggagcccc   1380
agctacccct cttctccagc tgggctctgc aattcccctc tgctgctgtc cctccccctt   1440
gtcctttccc ttcagtaccc tctcagctcc aggtggctct gaggtgcctg tcccaccccc   1500
accccagct  caatggactg aaggggaag  ggacacacaa gaagaagggc acctagttc    1560
tacctcaggc agctcaagca gcgaccgccc cctcctctag ctgtgggggt gagggtccca   1620
tgtggtggca caggccccct tgagtggggt tatctctgtg ttaggggtat atgatggggg   1680
agtagatctt tctaggaggg agacactggc ccctcaaatc gtccagcgac cttcctcatc   1740
caccccatcc ctccccagtt cattgcactt tgattagcag cggaacaagg agtcagacat   1800
```

```
tttaagatgg tggcagtaga ggctatggac agggcatgcc acgtgggctc atatggggct    1860
gggagtagtt gtctttcctg cactaacgt tgagcccctg gaggcactga agtgcttagt    1920
gtacttggag tattggggtc tgaccccaaa caccttccag ctcctgtaac atactggcct    1980
ggactgtttt ctctcggctc cccatgtgtc ctggttcccg tttctccacc tagactgtaa    2040
acctctcgag ggcagggacc acaccctgta ctgttctgtg tctttcacag ctcctcccac    2100
aatgctgaat atacagcagg tgctcaataa atgattctta gtgactttaa aaaaaaaaa    2160 aaaaaaaa                                                             2168
```

<210> SEQ ID NO 8
<211> LENGTH: 164
<212> TYPE: PRT
<213> ORGANISM: Homo sapiens

<400> SEQUENCE: 8

```
Met Ser Glu Pro Ala Gly Asp Val Arg Gln Asn Pro Cys Gly Ser Lys
1               5                   10                  15

Ala Cys Arg Arg Leu Phe Gly Pro Val Asp Ser Glu Gln Leu Ser Arg
            20                  25                  30

Asp Cys Asp Ala Leu Met Ala Gly Cys Ile Gln Glu Ala Arg Glu Arg
        35                  40                  45

Trp Asn Phe Asp Phe Val Thr Glu Thr Pro Leu Glu Gly Asp Phe Ala
    50                  55                  60

Trp Glu Arg Val Arg Gly Leu Gly Leu Pro Lys Leu Tyr Leu Pro Thr
65                  70                  75                  80

Gly Pro Arg Arg Gly Arg Asp Glu Leu Gly Gly Gly Arg Arg Pro Gly
                85                  90                  95

Thr Ser Pro Ala Leu Leu Gln Gly Thr Ala Glu Glu Asp His Val Asp
            100                 105                 110

Leu Ser Leu Ser Cys Thr Leu Val Pro Arg Ser Gly Glu Gln Ala Glu
        115                 120                 125

Gly Ser Pro Gly Gly Pro Gly Asp Ser Gln Gly Arg Lys Arg Arg Gln
    130                 135                 140

Thr Ser Met Thr Asp Phe Tyr His Ser Lys Arg Arg Leu Ile Phe Ser
145                 150                 155                 160

Lys Arg Lys Pro
```

<210> SEQ ID NO 9
<211> LENGTH: 2586
<212> TYPE: DNA
<213> ORGANISM: Homo sapiens

<400> SEQUENCE: 9

```
gattggggtt ttcccctccc atgtgctcaa gactggcgct aaaagttttg agcttctcaa     60
aagtctagag ccaccgtcca gggagcaggt agctgctggg ctccggggac actttgcgtt    120
cgggctggga gcgtgctttc cacgacggtg acacgcttcc ctggattggc agccagactg    180
ccttccgggt cactgccatg gaggagccgc agtcagatcc tagcgtcgag ccccctctga    240
gtcaggaaac attttcagac ctatggaaac tacttcctga aaacaacgtt ctgtccccct    300
tgccgtccca agcaatggat gatttgatgc tgtccccgga cgatattgaa caatggttca    360
ctgaagaccc aggtccagat gaagctccca atgtgcaga ggctgctccc ccgtggcc     420 ctgcaccagc agctcctaca ccggcggccc ctgcaccagc ccctcctgg ccctgtcat     480
```

| | |
|---|---|
| cttctgtccc ttcccagaaa acctaccagg gcagctacgg tttccgtctg ggcttcttgc | 540 |
| attctgggac agccaagtct gtgacttgca cgtactcccc tgccctcaac aagatgtttt | 600 |
| gccaactggc caagacctgc cctgtgcagc tgtgggttga ttccacaccc ccgcccggca | 660 |
| cccgcgtccg cgccatggcc atctacaagc agtcacagca catgacggag gttgtgaggc | 720 |
| gctgccccca ccatgagcgc tgctcagata gcgatggtct ggcccctcct cagcatctta | 780 |
| tccgagtgga aggaaatttg cgtgtggagt atttggatga cagaaacact tttcgacata | 840 |
| gtgtggtggt gccctatgag ccgcctgagg ttggctctga ctgtaccacc atccactaca | 900 |
| actacatgtg taacagttcc tgcatgggcg gcatgaaccg gaggcccatc ctcaccatca | 960 |
| tcacactgga agactccagt ggtaatctac tgggacggaa cagctttgag gtgcgtgttt | 1020 |
| gtgcctgtcc tgggagagac cggcgcacag aggaagagaa tctccgcaag aaaggggagc | 1080 |
| ctcaccacga gctgccccca gggagcacta agcgagcact gcccaacaac accagctcct | 1140 |
| ctccccagcc aaagaagaaa ccactggatg agaatatttc acccttcag atccgtgggc | 1200 |
| gtgagcgctt cgagatgttc cgagagctga atgaggcctt ggaactcaag gatgcccagg | 1260 |
| ctgggaagga gccagggggg agcagggctc actccagcca cctgaagtcc aaaaagggtc | 1320 |
| agtctacctc ccgccataaa aaactcatgt tcaagacaga agggcctgac tcagactgac | 1380 |
| attctccact tcttgttccc cactgacagc ctcccacccc catctctccc tccctgcca | 1440 |
| ttttgggttt tgggtctttg aacccttgct tgcaataggt gtgcgtcaga agcacccagg | 1500 |
| acttccattt gctttgtccc ggggctccac tgaacaagtt ggcctgcact ggtgttttgt | 1560 |
| tgtggggagg aggatgggga gtaggacata ccagcttaga ttttaaggtt tttactgtga | 1620 |
| gggatgtttg ggagatgtaa gaaatgttct tgcagttaag ggttagttta caatcagcca | 1680 |
| cattctaggt aggggcccac ttcaccgtac taaccaggga agctgtccct cactgttgaa | 1740 |
| ttttctctaa cttcaaggcc catatctgtg aaatgctggc atttgcacct acctcacaga | 1800 |
| gtgcattgtg agggttaatg aaataatgta catctggcct tgaaaccacc ttttattaca | 1860 |
| tggggtctag aacttgaccc ccttgagggt gcttgttccc tctccctgtt ggtcggtggg | 1920 |
| ttggtagttt ctacagttgg gcagctggtt aggtagaggg agttgtcaag tctctgctgg | 1980 |
| cccagccaaa ccctgtctga caacctcttg gtgaacctta gtacctaaaa ggaaatctca | 2040 |
| ccccatccca caccctggag gatttcatct cttgtatatg atgatctgga tccaccaaga | 2100 |
| cttgttttat gctcagggtc aatttctttt ttcttttttt tttttttttt tcttttcttt | 2160 |
| tgagactggg tctcgctttg ttgcccaggc tggagtggag tggcgtgatc ttggcttact | 2220 |
| gcagcctttg cctccccggc tcgagcagtc ctgcctcagc ctccggagta gctgggacca | 2280 |
| caggttcatg ccaccatggc cagccaactt ttgcatgttt tgtagagatg gggtctcaca | 2340 |
| gtgttgccca ggctggtctc aaactcctgg gctcaggcga tccacctgtc tcagcctccc | 2400 |
| agagtgctgg gattacaatt gtgagccacc acgtccagct ggaagggtca acatcttta | 2460 |
| cattctgcaa gcacatctgc attttcaccc cacccttccc ctccttctcc ctttttatat | 2520 |
| cccatttta tatcgatctc ttatttaca ataaaacttt gctgccacct gtgtgtctga | 2580 |
| ggggtg | 2586 |

<210> SEQ ID NO 10
<211> LENGTH: 393
<212> TYPE: PRT
<213> ORGANISM: Homo sapiens

<400> SEQUENCE: 10

```
Met Glu Glu Pro Gln Ser Asp Pro Ser Val Glu Pro Leu Ser Gln
1               5                   10                  15

Glu Thr Phe Ser Asp Leu Trp Lys Leu Leu Pro Glu Asn Asn Val Leu
            20                  25                  30

Ser Pro Leu Pro Ser Gln Ala Met Asp Asp Leu Met Leu Ser Pro Asp
            35                  40                  45

Asp Ile Glu Gln Trp Phe Thr Glu Asp Pro Gly Pro Asp Glu Ala Pro
        50                  55                  60

Arg Met Pro Glu Ala Ala Pro Pro Val Ala Pro Ala Pro Ala Ala Pro
65                  70                  75                  80

Thr Pro Ala Ala Pro Ala Pro Ala Pro Ser Trp Pro Leu Ser Ser Ser
                85                  90                  95

Val Pro Ser Gln Lys Thr Tyr Gln Gly Ser Tyr Gly Phe Arg Leu Gly
            100                 105                 110

Phe Leu His Ser Gly Thr Ala Lys Ser Val Thr Cys Thr Tyr Ser Pro
        115                 120                 125

Ala Leu Asn Lys Met Phe Cys Gln Leu Ala Lys Thr Cys Pro Val Gln
        130                 135                 140

Leu Trp Val Asp Ser Thr Pro Pro Gly Thr Arg Val Arg Ala Met
145                 150                 155                 160

Ala Ile Tyr Lys Gln Ser Gln His Met Thr Glu Val Val Arg Arg Cys
        165                 170                 175

Pro His His Glu Arg Cys Ser Asp Ser Asp Gly Leu Ala Pro Pro Gln
        180                 185                 190

His Leu Ile Arg Val Glu Gly Asn Leu Arg Val Glu Tyr Leu Asp Asp
        195                 200                 205

Arg Asn Thr Phe Arg His Ser Val Val Val Pro Tyr Glu Pro Pro Glu
        210                 215                 220

Val Gly Ser Asp Cys Thr Thr Ile His Tyr Asn Tyr Met Cys Asn Ser
225                 230                 235                 240

Ser Cys Met Gly Gly Met Asn Arg Arg Pro Ile Leu Thr Ile Ile Thr
            245                 250                 255

Leu Glu Asp Ser Ser Gly Asn Leu Leu Gly Arg Asn Ser Phe Glu Val
            260                 265                 270

Arg Val Cys Ala Cys Pro Gly Arg Asp Arg Arg Thr Glu Glu Glu Asn
        275                 280                 285

Leu Arg Lys Lys Gly Glu Pro His His Glu Leu Pro Pro Gly Ser Thr
        290                 295                 300

Lys Arg Ala Leu Pro Asn Asn Thr Ser Ser Ser Pro Gln Pro Lys Lys
305                 310                 315                 320

Lys Pro Leu Asp Gly Glu Tyr Phe Thr Leu Gln Ile Arg Gly Arg Glu
            325                 330                 335

Arg Phe Glu Met Phe Arg Glu Leu Asn Glu Ala Leu Glu Leu Lys Asp
            340                 345                 350

Ala Gln Ala Gly Lys Glu Pro Gly Gly Ser Arg Ala His Ser Ser His
        355                 360                 365

Leu Lys Ser Lys Lys Gly Gln Ser Thr Ser Arg His Lys Lys Leu Met
        370                 375                 380

Phe Lys Thr Glu Gly Pro Asp Ser Asp
385                 390

<210> SEQ ID NO 11
<211> LENGTH: 12507
```

<212> TYPE: DNA
<213> ORGANISM: Homo sapiens

<400> SEQUENCE: 11

```
taccgggcgg aggtgagcgc ggcgccggct cctcctgcgg cggactttgg gtgcgacttg      60
acgagcggtg gttcgacaag tggccttgcg ggccggatcg tcccagtgga agagttgtaa     120
atttgcttct ggccttcccc tacggattat acctggcctt ccctacgga ttatactcaa      180
cttactgttt agaaaatgtg gcccacgaga cgcctggtta ctatcaaaag gagcggggtc     240
gacggtcccc actttcccct gagcctcagc acctgcttgt ttggaagggg tattgaatgt     300
gacatccgta tccagcttcc tgttgtgtca aaacaacatt gcaaaattga aatccatgag     360
caggaggcaa tattacataa tttcagttcc acaaatccaa cacaagtaaa tgggtctgtt     420
attgatgagc ctgtacggct aaaacatgga gatgtaataa ctattattga tcgttccttc     480
aggtatgaaa atgaaagtct tcagaatgga aggaagtcaa ctgaatttcc aagaaaaata     540
cgtgaacagg agccagcacg tcgtgtctca agatctagct tctcttctga ccctgatgag     600
aaagctcaag attccaaggc ctattcaaaa atcactgaag gaaaagtttc aggaaatcct     660
caggtacata tcaagaatgt caaagaagac agtaccgcag atgactcaaa agacagtgtt     720
gctcagggaa caactaatgt tcattcctca gaacatgctg gacgtaatgg cagaaatgca     780
gctgatccca tttctgggga ttttaaagaa atttccagcg ttaaattagt gagccgttat     840
ggagaattga agtctgttcc cactacacaa tgtcttgaca atagcaaaaa aaatgaatct     900
ccctttgga agctttatga gtcagtgaag aaagagttgg atgtaaaatc acaaaaagaa     960
aatgtcctac agtattgtag aaaatctgga ttacaaactg attacgcaac agagaaagaa    1020
agtgctgatg gtttacaggg ggagacccaa ctgttggtct cgcgtaagtc aagaccaaaa    1080
tctggtggga gcggccacgc tgtggcagag cctgcttcac ctgaacaaga gcttgaccag    1140
aacaagggga agggaagaga cgtggagtct gttcagactc ccagcaaggc tgtgggcgcc    1200
agctttcctc tctatgagcc ggctaaaatg aagaccctg tacaatattc acagcaacaa    1260
aattctccac aaaaacataa gaacaaagac ctgtatacta ctggtagaag agaatctgtg    1320
aatctgggta aaagtgaagg cttcaaggct ggtgataaaa ctcttactcc caggaagctt    1380
tcaactagaa atcgaacacc agctaaagtt gaagatgcag ctgactctgc cactaagcca    1440
gaaaatctct cttccaaaac cagaggaagt attcctacag atgtggaagt tctgcctacg    1500
gaaactgaaa ttcacaatga gccattttta actctgtggc tcactcaagt tgagaggaag    1560
atccaaaagg attccctcag caagcctgag aaattgggca ctacagctgg acagatgtgc    1620
tctgggttac ctggtcttag ttcagttgat atcaacaact ttggtgattc cattaatgag    1680
agtgagggaa tacctttgaa aagaaggcgt gtgtcctttg gtgggcacct aagacctgaa    1740
ctatttgatg aaaacttgcc tcctaatacg cctctcaaaa ggggagaagc cccaaccaaa    1800
agaaagtctc tggtaatgca cactccacct gtcctgaaga aaatcatcaa ggaacagcct    1860
caaccatcag aaaacaaga gtcaggttca gaaatccatg tggaagtgaa ggcacaaagc    1920
ttggttataa gccctccagc tcctagtcct aggaaaactc cagttgccag tgatcaacgc    1980
cgtaggtcct gcaaaacagc ccctgcttcc agcagcaaat ctcagacaga ggttcctaag    2040
agaggaggga gaaagagtgg caacctgcct tcaaagagag tgtctatcag ccgaagtcaa    2100
catgatattt tacagatgat atgttccaaa gaagaagtg gtgcttcgga agcaaatctg    2160
attgttgcaa aatcatgggc agatgtagta aaacttggtg caaaacaaac acaaactaaa    2220
```

```
gtcataaaac atggtcctca aaggtcaatg aacaaaaggc aaagaagacc tgctactcca    2280
aagaagcctg tgggcgaagt tcacagtcaa tttagtacag gccacgcaaa ctctccttgt    2340
accataataa tagggaaagc tcatactgaa aaagtacatg tgcctgctcg accctacaga    2400
gtgctcaaca acttcatttc caaccaaaaa atggactttta aggaagatct ttcaggaata    2460
gctgaaatgt tcaagacccc agtgaaggag caaccgcagt tgacaagcac atgtcacatc    2520
gctatttcaa attcagagaa tttgcttgga aaacagtttc aaggaactga ttcaggagaa    2580
gaacctctgc tccccacctc agagagttttt ggaggaaatg tgttcttcag tgcacagaat    2640
gcagcaaaac agccatctga taaatgctct gcaagccctc ccttaagacg gcagtgtatt    2700
agagaaaatg gaaacgtagc aaaaacgccc aggaacacct acaaaatgac ttctctggag    2760
acaaaaactt cagatactga gacagagcct tcaaaaacag tatccactgc aaacaggtca    2820
ggaaggtcta cagagttcag gaatatacag aagctacctg tggaaagtaa gagtgaagaa    2880
acaaatacag aaattgttga gtgcatccta aaaagaggtc agaaggcaac actactacaa    2940
caaaggagag aaggagagat gaaggaaata gaaagacctt ttgagacata taggaaaaat    3000
attgaattaa aagaaaacga tgaaaagatg aaagcaatga gagatcaag aacttgggggg    3060 cagaaatgtg caccaatgtc tgacctgaca gacctcaaga gcttgcctga tacagaactc    3120
atgaaagaca cggcacgtgg ccagaatctc ctccaaaccc aagatcatgc caaggcacca    3180
aagagtgaga aaggcaaaat cactaaaatg ccctgccagt cattcaaacc agaaccaata    3240
aacaccccaa cacacacaaa acaacagttg aaggcatccc tggggaaagt aggtgtgaaa    3300
gaagagctcc tagcagtcgg caagttcaca cggacgtcag gggagaccac gcacacgcac    3360
agagagccag caggagatgg caagagcatc agaacgttta aggagtctcc aaagcagatc    3420
ctggacccag cagcccgtgt aactggaatg aagaagtggc caagaacgcc taaggaagag    3480
gcccagtcac tagaagacct ggctggcttc aaagagctct tccagacacc aggtccctct    3540
gaggaatcaa tgactgatga gaaaactacc aaaatagcct gcaaatctcc accaccagaa    3600
tcagtggaca ctccaacaag cacaaagcaa tggcctaaga aagtctcag gaaagcagat    3660 gtagaggaag aattcttagc actcaggaaa ctaacaccat cagcagggaa agccatgctt    3720
acgcccaaac cagcaggagg tgatgagaaa gacattaaag catttatggg aactccagtg    3780
cagaaactgg acctggcagg aactttacct ggcagcaaaa gacagctaca gactcctaag    3840
gaaaaggccc aggctctaga agacctggct ggctttaaag agctcttcca gactcctggt    3900
cacaccgagg aattagtggc tgctggtaaa accactaaaa taccctgcga ctctccacag    3960
tcagacccag tggacacccc aacaagcaca aagcaacgac ccaagagaag tatcaggaaa    4020
gcagatgtag agggagaact cttagcgtgc aggaatctaa tgccatcagc aggcaaagcc    4080
atgcacacgc ctaaaccatc agtaggtgaa gagaaagaca tcatcatatt tgtgggaact    4140
ccagtgcaga aactggacct gacagagaac ttaccggca gcaagagacg gccacaaact    4200
cctaaggaag aggcccaggc tctggaagac ctgactggct ttaaagagct cttccagacc    4260
cctggtcata ctgaagaagc agtggctgct ggcaaaacta ctaaaatgcc ctgcgaatct    4320
tctccaccag aatcagcaga caccccaaca agcacaagaa ggcagcccaa gacacctttg    4380
gagaaaaggg acgtacagaa ggagctctca gccctgaaga agctcacaca gacatcaggg    4440
gaaaccacac acacagataa agtaccagga ggtgaggata aaagcatcaa cgcgtttagg    4500
gaaactgcaa aacagaaact ggaccagca gcaagtgtaa ctggtagcaa gaggcaccca    4560
aaaactaagg aaaaggccca ccccctagaa gacctggctg gcttgaaaga gctcttccag    4620
```

```
acaccagtat gcactgacaa gcccacgact cacgagaaaa ctaccaaaat agcctgcaga    4680
tcacaaccag acccagtgga cacaccaaca agctccaagc cacagtccaa gagaagtctc    4740
aggaaagtgg acgtagaaga agaattcttc gcactcagga aacgaacacc atcagcaggc    4800
aaagccatgc acacacccaa accagcagta agtggtgaga aaaacatcta cgcatttatg    4860
ggaactccag tgcagaaact ggacctgaca gagaacttaa ctggcagcaa gagacggcta    4920
caaactccta aggaaaaggc ccaggctcta aagacctgg ctggctttaa agagctcttc     4980
cagacacgag gtcacactga ggaatcaatg actaacgata aaactgccaa agtagcctgc    5040
aaatcttcac aaccagaccc agacaaaaac ccagcaagct ccaagcgacg gctcaagaca    5100
tccctgggga aagtgggcgt gaaagaagag ctcctagcag ttggcaagct cacacagaca    5160
tcaggagaga ctacacacac acacacagag ccaacaggga tggtaagag catgaaagca     5220 tttatggagt ctccaaagca gatcttagac tcagcagcaa gtctaactgg cagcaagagg    5280
cagctgagaa ctcctaaggg aaagtctgaa gtccctgaag acctggccgg cttcatcgag    5340
ctcttccaga caccaagtca cactaaggaa tcaatgacta acgaaaaaac taccaaagta    5400
tcctacagag cttcacagcc agacctagtg acacccccaa caagctccaa gccacagccc    5460
aagagaagtc tcaggaaagc agacactgaa gaagaatttt tagcatttag gaaacaaacg    5520
ccatcagcag gcaaagccat gcacacaccc aaaccagcag taggtgaaga gaaagacatc    5580
aacacgtttt tgggaactcc agtgcagaaa ctggaccagc caggaaattt acctggcagc    5640
aatagacggc tacaaactcg taaggaaaag gcccaggctc tagaagaact gactggcttc    5700
agagagcttt tccagacacc atgcactgat aaccccacga ctgatgagaa aactaccaaa    5760
aaaatactct gcaaatctcc gcaatcagac ccagcggaca ccccaacaaa cacaaagcaa    5820
cggcccaaga gaagcctcaa gaaagcagac gtagaggaag aatttttagc attcaggaaa    5880
ctaacaccat cagcaggcaa agccatgcac acgcctaaag cagcagtagg tgaagagaaa    5940
gacatcaaca catttgtggg gactccagtg gagaaactgg acctgctagg aaatttacct    6000
ggcagcaaga gacggccaca aactcctaaa gaaaaggcca aggctctaga agatctggct    6060
ggcttcaaag agctcttcca gacaccaggt cacactgagg aatcaatgac cgatgacaaa    6120
atcacagaag tatcctgcaa atctccacaa ccagacccag tcaaaacccc aacaagctcc    6180
aagcaacgac tcaagatatc cttggggaaa gtaggtgtga agaagaggt cctaccagtc     6240 ggcaagctca cacagacgtc agggaagacc acacagacac acagagagac agcaggagat    6300
ggaaagagca tcaaagcgtt taaggaatct gcaaagcaga tgctggaccc agcaaactat    6360
ggaactggga tggagaggtg gccaagaaca cctaaggaag aggcccaatc actagaagac    6420
ctggccggct tcaagagct cttccagaca ccagaccaca ctgaggaatc aacaactgat     6480
gacaaaacta ccaaaatagc ctgcaaatct ccaccaccag aatcaatgga cactccaaca    6540
agcacaagga ggcggcccaa acacctttg ggaaaaggg atatagtgga agagctctca      6600
gccctgaagc agctcacaca gaccacacac acagacaaag taccaggaga tgaggataaa    6660
ggcatcaacg tgttcaggga aactgcaaaa cagaaactgg acccagcagc aagtgtaact    6720
ggtagcaaga ggcagccaag aactcctaag ggaaaagccc aaccctaga agacttggct     6780 ggcttgaaag agctcttcca gacaccaata tgcactgaca gcccacgac tcatgagaaa     6840 actaccaaaa tagcctgcag atctccacaa ccagacccag tgggtacccc aacaatcttc    6900
aagccacagt ccaagagaag tctcaggaaa gcagacgtag aggaagaatc cttagcactc    6960
```

```
aggaaacgaa caccatcagt agggaaagct atggacacac ccaaaccagc aggaggtgat      7020
gagaaagaca tgaaagcatt tatgggaact ccagtgcaga aattggacct gccaggaaat      7080
ttacctggca gcaaaagatg gccacaaact cctaaggaaa aggcccaggc tctagaagac      7140
ctggctggct tcaaagagct cttccagaca ccaggcactg acaagcccac gactgatgag      7200
aaaactacca aaatagcctg caaatctcca caaccagacc cagtggacac cccagcaagc      7260
acaaagcaac ggcccaagag aaacctcagg aaagcagacg tagaggaaga atttttagca      7320
ctcaggaaac gaacaccatc agcaggcaaa gccatggaca caccaaaacc agcagtaagt      7380
gatgagaaaa atatcaacac atttgtggaa actccagtgc agaaactgga cctgctagga      7440
aatttacctg gcagcaagag acagccacag actcctaagg aaaaggctga ggctctagag      7500
gacctggttg gcttcaaaga actcttccag acaccaggtc acactgagga atcaatgact      7560
gatgacaaaa tcacagaagt atcctgtaaa tctccacagc cagagtcatt caaaacctca      7620
agaagctcca agcaaaggct caagataccc ctggtgaaag tggacatgaa agaagagccc      7680
ctagcagtca gcaagctcac acggacatca ggggagacta cgcaaacaca cacagagcca      7740
acaggagata gtaagagcat caaagcgttt aaggagtctc caaagcagat cctggaccca      7800
gcagcaagtg taactggtag caggaggcag ctgagaactc gtaaggaaaa gcccgtgct       7860 ctagaagacc tggttgactt caaagagctc ttctcagcac caggtcacac tgaagagtca      7920
atgactattg caaaaacac aaaaattccc tgcaaatctc ccccaccaga actaacagac        7980
actgccacga gcacaaagag atgccccaag acacgtccca ggaaagaagt aaaagaggag      8040
ctctcagcag ttgagaggct cacgcaaaca tcagggcaaa gcacacacac acacaaagaa      8100
ccagcaagcg gtgatgaggg catcaaagta ttgaagcaac gtgcaaagaa gaaaccaaac      8160
ccagtagaag aggaacccag caggagaagg ccaagagcac taaggaaaaa ggcccaaccc      8220
ctggaagacc tggccggctt cacagagctc tctgaaacat caggtcacac tcaggaatca      8280
ctgactgctg gcaaagccac taaaataccc tgcgaatctc ccccactaga agtggtagac      8340
accacagcaa gcacaaagag gcatctcagg acacgtgtgc agaaggtaca agtaaaagaa      8400
gagccttcag cagtcaagtt cacacaaaca tcagggggaaa ccacggatgc agacaaagaa     8460
ccagcaggtg aagataaagg catcaaagca ttgaaggaat ctgcaaaaca gacaccggct      8520
ccagcagcaa gtgtaactgg cagcaggaga cggccaagag cacccaggga agtgcccaa       8580 gccatagaag acctagctgg cttcaaagac ccagcagcag gtcacactga agaatcaatg      8640
actgatgaca aaaccactaa aatacccgtc aaatcatcac cagaactaga agacaccgca      8700
acaagctcaa agagacggcc caggacacgt gcccagaaag tagaagtgaa ggaggagctg      8760
ttagcagttg gcaagctcac acaaacctca ggggagacca cgcacaccga caaagagccg      8820
gtaggtgagg gcaaaggcac gaaagcattt aagcaacctg caaagcggaa gctggacgca      8880
gaagatgtaa ttggcagcag gagacagcca agagcaccta ggaaaaaggc caacccctg       8940 gaagatctgg ccagcttcca agagctctct caaacaccag gccacactga ggaactggca      9000
aatggtgctg ctgatagctt tacaagcgct ccaaagcaaa cacctgacag tggaaaacct      9060
ctaaaaatat ccagaagagt tcttcgggcc cctaaagtag aacccgtggg agacgtggta      9120
agcaccagag accctgtaaa atcacaaagc aaaagcaaca cttccctgcc cccactgccc      9180
ttcaagaggg gaggtggcaa agatggaagc gtcacgggaa ccaagaggct gcgctgcatg      9240
ccagcaccag aggaaattgt ggaggagctg ccagccagca gaagcagag ggttgctccc       9300 agggcaagag gcaaatcatc cgaacccgtg gtcatcatga agagaagttt gaggacttct      9360
```

```
gcaaaagaa ttgaacctgc ggaagagctg aacagcaacg acatgaaaac caacaaagag   9420
gaacacaaat tacaagactc ggtccctgaa aataagggaa tatccctgcg ctccagacgc   9480
caaaataaga ctgaggcaga acagcaaata actgaggtct ttgtattagc agaaagaata   9540
gaaataaaca gaaatgaaaa gaagcccatg aagacctccc cagagatgga cattcagaat   9600
ccagatgatg gagcccggaa acccatacct agagacaaag tcactgagaa caaaaggtgc   9660
ttgaggtctg ctagacagaa tgagagctcc cagcctaagg tggcagagga gagcggaggg   9720
cagaagagtg cgaaggttct catgcagaat cagaaaggga aggagaagc aggaaattca    9780 gactccatgt gcctgagatc aagaaagaca aaaagccagc ctgcagcaag cactttggag   9840
agcaaatctg tgcagagagt aacgcggagt gtcaagaggt gtgcagaaaa tccaaagaag   9900
gctgaggaca atgtgtgtgt caagaaaata agaaccagaa gtcatagga cagtgaagat    9960 atttgacaga aaaatcgaac tgggaaaaat ataataaagt tagttttgtg ataagttcta  10020
gtgcagtttt tgtcataaat tacaagtgaa ttctgtaagt aaggctgtca gtctgcttaa  10080
gggaagaaaa ctttggattt gctgggtctg aatcggcttc ataaactcca ctgggagcac  10140
tgctgggctc ctggactgag aatagttgaa caccgggggc tttgtgaagg agtctgggcc  10200
aaggtttgcc ctcagctttg cagaatgaag ccttgaggtc tgtcaccacc cacagccacc  10260
ctacagcagc cttaactgtg acacttgcca cactgtgtcg tcgtttgttt gcctatgtcc  10320
tccagggcac ggtggcagga acaactatcc tcgtctgtcc caacactgag caggcactcg  10380
gtaaacacga atgaatggat gagcgcacgg atgaatggag cttacaagat ctgtctttcc  10440
aatggccggg ggcatttggt ccccaaatta aggctattgg acatctgcac aggacagtcc  10500 tattttgat gtccttcct ttctgaaaat aaagtttgt gctttggaga atgactcgtg     10560
agcacatctt tagggaccaa gagtgacttt ctgtaaggag tgactcgtgg cttgccttgg  10620
tctcttggga atacttttct aactagggtt gctctcacct gagacattct ccacccgcgg  10680
aatctcaggg tcccaggctg tgggccatca cgacctcaaa ctggctccta atctccagct  10740
ttcctgtcat tgaaagcttc ggaagtttac tggctctgct cccgcctgtt ttctttctga  10800
ctctatctgg cagcccgatg ccacccagta caggaagtga caccagtact ctgtaaagca  10860
tcatcatcct tggagagact gagcactcag caccttcagc cacgatttca ggatcgcttc  10920
cttgtgagcc gctgcctccg aaatctcctt tgaagcccag acatctttct ccagcttcag  10980
acttgtagat ataactcgtt catcttcatt tactttccac tttgccccct gtcctctctg  11040
tgttccccaa atcagagaat agcccgccat ccccaggtc acctgtctgg attcctcccc   11100
attcacccac cttgccaggt gcaggtgagg atggtgcacc agacagggta gctgtccccc  11160
aaaatgtgcc ctgtgcgggc agtgccctgt ctccacgttt gtttcccag tgtctggcgg   11220 ggagccaggt gacatcataa atacttgctg aatgaatgca gaaatcagcg gtactgactt  11280
gtactatatt ggctgccatg ataggttct cacagcgtca tccatgatcg taagggaaa    11340 tgacattctg cttgagggag ggaatagaaa ggggcaggga ggggacatct gagggcttca  11400
cagggctgca aagggtacag ggattgcacc agggcagaac aggggagggt gttcaaggaa  11460
gagtggctct tagcagaggc actttggaag gtgtgaggca taaatgcttc cttctacgta  11520
ggccaacctc aaaactttca gtaggaatgt tgctatgatc aagttgttct aacactttag  11580
acttagtagt aattatgaac ctcacataga aaaatttcat ccagccatat gcctgtggag  11640
tggaatattc tgtttagtag aaaaatccctt tagagttcag ctctaaccag aaatcttgct  11700
```

```
gaagtatgtc agcaccttt ctcaccctgg taagtacagt atttcaagag cacgctaagg   11760
gtggttttca ttttacaggg ctgttgatga tgggttaaaa atgttcattt aagggctacc   11820
cccgtgttta atagatgaac accacttcta cacaaccctc cttggtactg ggggagggag   11880
agatctgaca aatactgccc attccctag gctgactgga tttgagaaca aatacccacc   11940
catttccacc atggtatggt aacttctctg agcttcagtt tccaagtgaa tttccatgta   12000
ataggacatt cccattaaat acaagctgtt tttacttttt cgcctcccag ggcctgtggg   12060
atctggtccc ccagcctctc ttgggctttc ttacactaac tctgtaccta ccatctcctg   12120
cctcccttag gcaggcacct ccaaccacca cacactccct gctgttttcc ctgcctggaa   12180
ctttccctcc tgccccacca agatcattc atccagtcct gagctcagct taagggaggc   12240
ttcttgcctg tgggttccct caccccatg cctgtcctcc aggctggggc aggttcttag   12300
tttgcctgga attgttctgt acctctttgt agcacgtagt gttgtggaaa ctaagccact   12360
aattgagttt ctggctcccc tcctgggggtt gtaagttttg ttcattcatg agggccgact   12420
gcatttcctg gttactctat cccagtgacc agccacagga gatgtccaat aaagtatgtg   12480
atgaaatggt cttaaaaaaa aaaaaaa                                       12507
```

<210> SEQ ID NO 12
<211> LENGTH: 3256
<212> TYPE: PRT
<213> ORGANISM: Homo sapiens

<400> SEQUENCE: 12

Met Trp Pro Thr Arg Arg Leu Val Thr Ile Lys Arg Ser Gly Val Asp
1               5                   10                  15

Gly Pro His Phe Pro Leu Ser Leu Ser Thr Cys Leu Phe Gly Arg Gly
                20                  25                  30

Ile Glu Cys Asp Ile Arg Ile Gln Leu Pro Val Val Ser Lys Gln His
            35                  40                  45

Cys Lys Ile Glu Ile His Glu Gln Glu Ala Ile Leu His Asn Phe Ser
        50                  55                  60

Ser Thr Asn Pro Thr Gln Val Asn Gly Ser Val Ile Asp Glu Pro Val
65                  70                  75                  80

Arg Leu Lys His Gly Asp Val Ile Thr Ile Ile Asp Arg Ser Phe Arg
                85                  90                  95

Tyr Glu Asn Glu Ser Leu Gln Asn Gly Arg Lys Ser Thr Glu Phe Pro
            100                 105                 110

Arg Lys Ile Arg Glu Gln Glu Pro Ala Arg Arg Val Ser Arg Ser Ser
        115                 120                 125

Phe Ser Ser Asp Pro Asp Glu Lys Ala Gln Asp Ser Lys Ala Tyr Ser
    130                 135                 140

Lys Ile Thr Glu Gly Lys Val Ser Gly Asn Pro Gln Val His Ile Lys
145                 150                 155                 160

Asn Val Lys Glu Asp Ser Thr Ala Asp Ser Lys Asp Ser Val Ala
                165                 170                 175

Gln Gly Thr Thr Asn Val His Ser Ser Glu His Ala Gly Arg Asn Gly
            180                 185                 190

Arg Asn Ala Ala Asp Pro Ile Ser Gly Asp Phe Lys Glu Ile Ser Ser
        195                 200                 205

Val Lys Leu Val Ser Arg Tyr Gly Glu Leu Lys Ser Val Pro Thr Thr
    210                 215                 220

Gln Cys Leu Asp Asn Ser Lys Lys Asn Glu Ser Pro Phe Trp Lys Leu

-continued

```
                225                 230                 235                 240
Tyr Glu Ser Val Lys Lys Glu Leu Asp Val Lys Ser Gln Lys Glu Asn
                245                 250                 255

Val Leu Gln Tyr Cys Arg Lys Ser Gly Leu Gln Thr Asp Tyr Ala Thr
            260                 265                 270

Glu Lys Glu Ser Ala Asp Gly Leu Gln Gly Glu Thr Gln Leu Leu Val
        275                 280                 285

Ser Arg Lys Ser Arg Pro Lys Ser Gly Ser Gly His Ala Val Ala
    290                 295                 300

Glu Pro Ala Ser Pro Glu Gln Glu Leu Asp Gln Asn Lys Gly Lys Gly
305                 310                 315                 320

Arg Asp Val Glu Ser Val Gln Thr Pro Ser Lys Ala Val Gly Ala Ser
                325                 330                 335

Phe Pro Leu Tyr Glu Pro Ala Lys Met Lys Thr Pro Val Gln Tyr Ser
            340                 345                 350

Gln Gln Gln Asn Ser Pro Gln Lys His Lys Asn Lys Asp Leu Tyr Thr
        355                 360                 365

Thr Gly Arg Arg Glu Ser Val Asn Leu Gly Lys Ser Glu Gly Phe Lys
    370                 375                 380

Ala Gly Asp Lys Thr Leu Thr Pro Arg Lys Leu Ser Thr Arg Asn Arg
385                 390                 395                 400

Thr Pro Ala Lys Val Glu Asp Ala Ala Asp Ser Ala Thr Lys Pro Glu
                405                 410                 415

Asn Leu Ser Ser Lys Thr Arg Gly Ser Ile Pro Thr Asp Val Glu Val
            420                 425                 430

Leu Pro Thr Glu Thr Glu Ile His Asn Glu Pro Phe Leu Thr Leu Trp
        435                 440                 445

Leu Thr Gln Val Glu Arg Lys Ile Gln Lys Asp Ser Leu Ser Lys Pro
    450                 455                 460

Glu Lys Leu Gly Thr Thr Ala Gly Gln Met Cys Ser Gly Leu Pro Gly
465                 470                 475                 480

Leu Ser Ser Val Asp Ile Asn Asn Phe Gly Asp Ser Ile Asn Glu Ser
                485                 490                 495

Glu Gly Ile Pro Leu Lys Arg Arg Val Ser Phe Gly Gly His Leu
            500                 505                 510

Arg Pro Glu Leu Phe Asp Glu Asn Leu Pro Pro Asn Thr Pro Leu Lys
        515                 520                 525

Arg Gly Glu Ala Pro Thr Lys Arg Lys Ser Leu Val Met His Thr Pro
    530                 535                 540

Pro Val Leu Lys Lys Ile Ile Lys Glu Gln Pro Gln Pro Ser Gly Lys
545                 550                 555                 560

Gln Glu Ser Gly Ser Glu Ile His Val Glu Val Lys Ala Gln Ser Leu
                565                 570                 575

Val Ile Ser Pro Pro Ala Pro Ser Pro Arg Lys Thr Pro Val Ala Ser
            580                 585                 590

Asp Gln Arg Arg Arg Ser Cys Lys Thr Ala Pro Ala Ser Ser Ser Lys
        595                 600                 605

Ser Gln Thr Glu Val Pro Lys Arg Gly Arg Lys Ser Gly Asn Leu
    610                 615                 620

Pro Ser Lys Arg Val Ser Ile Ser Arg Ser Gln His Asp Ile Leu Gln
625                 630                 635                 640

Met Ile Cys Ser Lys Arg Arg Ser Gly Ala Ser Glu Ala Asn Leu Ile
                645                 650                 655
```

```
Val Ala Lys Ser Trp Ala Asp Val Val Lys Leu Gly Ala Lys Gln Thr
        660                 665                 670

Gln Thr Lys Val Ile Lys His Gly Pro Gln Arg Ser Met Asn Lys Arg
        675                 680                 685

Gln Arg Arg Pro Ala Thr Pro Lys Lys Pro Val Gly Glu Val His Ser
690                 695                 700

Gln Phe Ser Thr Gly His Ala Asn Ser Pro Cys Thr Ile Ile Gly
705                 710                 715                 720

Lys Ala His Thr Glu Lys Val His Val Pro Ala Arg Pro Tyr Arg Val
                725                 730                 735

Leu Asn Asn Phe Ile Ser Asn Gln Lys Met Asp Phe Lys Glu Asp Leu
            740                 745                 750

Ser Gly Ile Ala Glu Met Phe Lys Thr Pro Val Lys Glu Gln Pro Gln
        755                 760                 765

Leu Thr Ser Thr Cys His Ile Ala Ile Ser Asn Ser Glu Asn Leu Leu
    770                 775                 780

Gly Lys Gln Phe Gln Gly Thr Asp Ser Gly Glu Glu Pro Leu Leu Pro
785                 790                 795                 800

Thr Ser Glu Ser Phe Gly Gly Asn Val Phe Phe Ser Ala Gln Asn Ala
                805                 810                 815

Ala Lys Gln Pro Ser Asp Lys Cys Ser Ala Ser Pro Pro Leu Arg Arg
            820                 825                 830

Gln Cys Ile Arg Glu Asn Gly Asn Val Ala Lys Thr Pro Arg Asn Thr
        835                 840                 845

Tyr Lys Met Thr Ser Leu Glu Thr Lys Thr Ser Asp Thr Glu Thr Glu
    850                 855                 860

Pro Ser Lys Thr Val Ser Thr Ala Asn Arg Ser Gly Arg Ser Thr Glu
865                 870                 875                 880

Phe Arg Asn Ile Gln Lys Leu Pro Val Glu Ser Lys Ser Glu Glu Thr
                885                 890                 895

Asn Thr Glu Ile Val Glu Cys Ile Leu Lys Arg Gly Gln Lys Ala Thr
            900                 905                 910

Leu Leu Gln Gln Arg Arg Glu Gly Glu Met Lys Glu Ile Glu Arg Pro
        915                 920                 925

Phe Glu Thr Tyr Lys Glu Asn Ile Glu Leu Lys Glu Asn Asp Glu Lys
    930                 935                 940

Met Lys Ala Met Lys Arg Ser Arg Thr Trp Gly Gln Lys Cys Ala Pro
945                 950                 955                 960

Met Ser Asp Leu Thr Asp Leu Lys Ser Leu Pro Asp Thr Glu Leu Met
                965                 970                 975

Lys Asp Thr Ala Arg Gly Gln Asn Leu Leu Gln Thr Gln Asp His Ala
            980                 985                 990

Lys Ala Pro Lys Ser Glu Lys Gly Lys Ile Thr Lys Met Pro Cys Gln
        995                 1000                1005

Ser Leu Gln Pro Glu Pro Ile Asn Thr Pro Thr His Thr Lys Gln
    1010                1015                1020

Gln Leu Lys Ala Ser Leu Gly Lys Val Gly Val Lys Glu Glu Leu
    1025                1030                1035

Leu Ala Val Gly Lys Phe Thr Arg Thr Ser Gly Glu Thr Thr His
    1040                1045                1050

Thr His Arg Glu Pro Ala Gly Asp Gly Lys Ser Ile Arg Thr Phe
    1055                1060                1065
```

```
Lys Glu Ser Pro Lys Gln Ile Leu Asp Pro Ala Ala Arg Val Thr
    1070                1075                1080

Gly Met Lys Lys Trp Pro Arg Thr Pro Lys Glu Glu Ala Gln Ser
    1085                1090                1095

Leu Glu Asp Leu Ala Gly Phe Lys Glu Leu Phe Gln Thr Pro Gly
    1100                1105                1110

Pro Ser Glu Glu Ser Met Thr Asp Glu Lys Thr Thr Lys Ile Ala
    1115                1120                1125

Cys Lys Ser Pro Pro Glu Ser Val Asp Thr Pro Thr Ser Thr
    1130                1135                1140

Lys Gln Trp Pro Lys Arg Ser Leu Arg Lys Ala Asp Val Glu Glu
    1145                1150                1155

Glu Phe Leu Ala Leu Arg Lys Leu Thr Pro Ser Ala Gly Lys Ala
    1160                1165                1170

Met Leu Thr Pro Lys Pro Ala Gly Gly Asp Glu Lys Asp Ile Lys
    1175                1180                1185

Ala Phe Met Gly Thr Pro Val Gln Lys Leu Asp Leu Ala Gly Thr
    1190                1195                1200

Leu Pro Gly Ser Lys Arg Gln Leu Gln Thr Pro Lys Glu Lys Ala
    1205                1210                1215

Gln Ala Leu Glu Asp Leu Ala Gly Phe Lys Glu Leu Phe Gln Thr
    1220                1225                1230

Pro Gly His Thr Glu Glu Leu Val Ala Ala Gly Lys Thr Thr Lys
    1235                1240                1245

Ile Pro Cys Asp Ser Pro Gln Ser Asp Pro Val Asp Thr Pro Thr
    1250                1255                1260

Ser Thr Lys Gln Arg Pro Lys Arg Ser Ile Arg Lys Ala Asp Val
    1265                1270                1275

Glu Gly Glu Leu Leu Ala Cys Arg Asn Leu Met Pro Ser Ala Gly
    1280                1285                1290

Lys Ala Met His Thr Pro Lys Pro Ser Val Gly Glu Glu Lys Asp
    1295                1300                1305

Ile Ile Ile Phe Val Gly Thr Pro Val Gln Lys Leu Asp Leu Thr
    1310                1315                1320

Glu Asn Leu Thr Gly Ser Lys Arg Arg Pro Gln Thr Pro Lys Glu
    1325                1330                1335

Glu Ala Gln Ala Leu Glu Asp Leu Thr Gly Phe Lys Glu Leu Phe
    1340                1345                1350

Gln Thr Pro Gly His Thr Glu Glu Ala Val Ala Ala Gly Lys Thr
    1355                1360                1365

Thr Lys Met Pro Cys Glu Ser Ser Pro Pro Glu Ser Ala Asp Thr
    1370                1375                1380

Pro Thr Ser Thr Arg Arg Gln Pro Lys Thr Pro Leu Glu Lys Arg
    1385                1390                1395

Asp Val Gln Lys Glu Leu Ser Ala Leu Lys Lys Leu Thr Gln Thr
    1400                1405                1410

Ser Gly Glu Thr Thr His Thr Asp Lys Val Pro Gly Gly Glu Asp
    1415                1420                1425

Lys Ser Ile Asn Ala Phe Arg Glu Thr Ala Lys Gln Lys Leu Asp
    1430                1435                1440

Pro Ala Ala Ser Val Thr Gly Ser Lys Arg His Pro Lys Thr Lys
    1445                1450                1455

Glu Lys Ala Gln Pro Leu Glu Asp Leu Ala Gly Leu Lys Glu Leu
```

-continued

```
            1460                1465                1470
Phe Gln Thr Pro Val Cys Thr Asp Lys Pro Thr Thr His Glu Lys
            1475                1480                1485
Thr Thr Lys Ile Ala Cys Arg Ser Gln Pro Asp Pro Val Asp Thr
            1490                1495                1500
Pro Thr Ser Ser Lys Pro Gln Ser Lys Arg Ser Leu Arg Lys Val
            1505                1510                1515
Asp Val Glu Glu Glu Phe Phe Ala Leu Arg Lys Arg Thr Pro Ser
            1520                1525                1530
Ala Gly Lys Ala Met His Thr Pro Lys Pro Ala Val Ser Gly Glu
            1535                1540                1545
Lys Asn Ile Tyr Ala Phe Met Gly Thr Pro Val Gln Lys Leu Asp
            1550                1555                1560
Leu Thr Glu Asn Leu Thr Gly Ser Lys Arg Arg Leu Gln Thr Pro
            1565                1570                1575
Lys Glu Lys Ala Gln Ala Leu Glu Asp Leu Ala Gly Phe Lys Glu
            1580                1585                1590
Leu Phe Gln Thr Arg Gly His Thr Glu Glu Ser Met Thr Asn Asp
            1595                1600                1605
Lys Thr Ala Lys Val Ala Cys Lys Ser Ser Gln Pro Asp Pro Asp
            1610                1615                1620
Lys Asn Pro Ala Ser Ser Lys Arg Arg Leu Lys Thr Ser Leu Gly
            1625                1630                1635
Lys Val Gly Val Lys Glu Glu Leu Leu Ala Val Gly Lys Leu Thr
            1640                1645                1650
Gln Thr Ser Gly Glu Thr Thr His Thr His Thr Glu Pro Thr Gly
            1655                1660                1665
Asp Gly Lys Ser Met Lys Ala Phe Met Glu Ser Pro Lys Gln Ile
            1670                1675                1680
Leu Asp Ser Ala Ala Ser Leu Thr Gly Ser Lys Arg Gln Leu Arg
            1685                1690                1695
Thr Pro Lys Gly Lys Ser Glu Val Pro Glu Asp Leu Ala Gly Phe
            1700                1705                1710
Ile Glu Leu Phe Gln Thr Pro Ser His Thr Lys Glu Ser Met Thr
            1715                1720                1725
Asn Glu Lys Thr Thr Lys Val Ser Tyr Arg Ala Ser Gln Pro Asp
            1730                1735                1740
Leu Val Asp Thr Pro Thr Ser Ser Lys Pro Gln Pro Lys Arg Ser
            1745                1750                1755
Leu Arg Lys Ala Asp Thr Glu Glu Phe Leu Ala Phe Arg Lys
            1760                1765                1770
Gln Thr Pro Ser Ala Gly Lys Ala Met His Thr Pro Lys Pro Ala
            1775                1780                1785
Val Gly Glu Glu Lys Asp Ile Asn Thr Phe Leu Gly Thr Pro Val
            1790                1795                1800
Gln Lys Leu Asp Gln Pro Gly Asn Leu Pro Gly Ser Asn Arg Arg
            1805                1810                1815
Leu Gln Thr Arg Lys Glu Lys Ala Gln Ala Leu Glu Glu Leu Thr
            1820                1825                1830
Gly Phe Arg Glu Leu Phe Gln Thr Pro Cys Thr Asp Asn Pro Thr
            1835                1840                1845
Thr Asp Glu Lys Thr Thr Lys Lys Ile Leu Cys Lys Ser Pro Gln
            1850                1855                1860
```

```
Ser Asp Pro Ala Asp Thr Pro Thr Asn Thr Lys Gln Arg Pro Lys
1865                1870                1875

Arg Ser Leu Lys Lys Ala Asp Val Glu Glu Glu Phe Leu Ala Phe
1880                1885                1890

Arg Lys Leu Thr Pro Ser Ala Gly Lys Ala Met His Thr Pro Lys
1895                1900                1905

Ala Ala Val Gly Glu Glu Lys Asp Ile Asn Thr Phe Val Gly Thr
1910                1915                1920

Pro Val Glu Lys Leu Asp Leu Leu Gly Asn Leu Pro Gly Ser Lys
1925                1930                1935

Arg Arg Pro Gln Thr Pro Lys Glu Lys Ala Lys Ala Leu Glu Asp
1940                1945                1950

Leu Ala Gly Phe Lys Glu Leu Phe Gln Thr Pro Gly His Thr Glu
1955                1960                1965

Glu Ser Met Thr Asp Asp Lys Ile Thr Glu Val Ser Cys Lys Ser
1970                1975                1980

Pro Gln Pro Asp Pro Val Lys Thr Pro Thr Ser Ser Lys Gln Arg
1985                1990                1995

Leu Lys Ile Ser Leu Gly Lys Val Gly Val Lys Glu Glu Val Leu
2000                2005                2010

Pro Val Gly Lys Leu Thr Gln Thr Ser Gly Lys Thr Thr Gln Thr
2015                2020                2025

His Arg Glu Thr Ala Gly Asp Gly Lys Ser Ile Lys Ala Phe Lys
2030                2035                2040

Glu Ser Ala Lys Gln Met Leu Asp Pro Ala Asn Tyr Gly Thr Gly
2045                2050                2055

Met Glu Arg Trp Pro Arg Thr Pro Lys Glu Glu Ala Gln Ser Leu
2060                2065                2070

Glu Asp Leu Ala Gly Phe Lys Glu Leu Phe Gln Thr Pro Asp His
2075                2080                2085

Thr Glu Glu Ser Thr Thr Asp Asp Lys Thr Thr Lys Ile Ala Cys
2090                2095                2100

Lys Ser Pro Pro Pro Glu Ser Met Asp Thr Pro Thr Ser Thr Arg
2105                2110                2115

Arg Arg Pro Lys Thr Pro Leu Gly Lys Arg Asp Ile Val Glu Glu
2120                2125                2130

Leu Ser Ala Leu Lys Gln Leu Thr Gln Thr Thr His Thr Asp Lys
2135                2140                2145

Val Pro Gly Asp Glu Asp Lys Gly Ile Asn Val Phe Arg Glu Thr
2150                2155                2160

Ala Lys Gln Lys Leu Asp Pro Ala Ala Ser Val Thr Gly Ser Lys
2165                2170                2175

Arg Gln Pro Arg Thr Pro Lys Gly Lys Ala Gln Pro Leu Glu Asp
2180                2185                2190

Leu Ala Gly Leu Lys Glu Leu Phe Gln Thr Pro Ile Cys Thr Asp
2195                2200                2205

Lys Pro Thr Thr His Glu Lys Thr Thr Lys Ile Ala Cys Arg Ser
2210                2215                2220

Pro Gln Pro Asp Pro Val Gly Thr Pro Thr Ile Phe Lys Pro Gln
2225                2230                2235

Ser Lys Arg Ser Leu Arg Lys Ala Asp Val Glu Glu Ser Leu
2240                2245                2250
```

-continued

| | | | | | | | | | | | |
|---|---|---|---|---|---|---|---|---|---|---|---|
| Ala | Leu | Arg | Lys | Arg | Thr | Pro | Ser | Val | Gly | Lys | Ala | Met | Asp | Thr |
| | 2255 | | | | | 2260 | | | | | 2265 | | | |

Pro Lys Pro Ala Gly Gly Asp Glu Lys Asp Met Lys Ala Phe Met
    2270                2275                2280

Gly Thr Pro Val Gln Lys Leu Asp Leu Pro Gly Asn Leu Pro Gly
    2285                2290                2295

Ser Lys Arg Trp Pro Gln Thr Pro Lys Glu Lys Ala Gln Ala Leu
    2300                2305                2310

Glu Asp Leu Ala Gly Phe Lys Glu Leu Phe Gln Thr Pro Gly Thr
    2315                2320                2325

Asp Lys Pro Thr Thr Asp Glu Lys Thr Thr Lys Ile Ala Cys Lys
    2330                2335                2340

Ser Pro Gln Pro Asp Pro Val Asp Thr Pro Ala Ser Thr Lys Gln
    2345                2350                2355

Arg Pro Lys Arg Asn Leu Arg Lys Ala Asp Val Glu Glu Glu Phe
    2360                2365                2370

Leu Ala Leu Arg Lys Arg Thr Pro Ser Ala Gly Lys Ala Met Asp
    2375                2380                2385

Thr Pro Lys Pro Ala Val Ser Asp Glu Lys Asn Ile Asn Thr Phe
    2390                2395                2400

Val Glu Thr Pro Val Gln Lys Leu Asp Leu Leu Gly Asn Leu Pro
    2405                2410                2415

Gly Ser Lys Arg Gln Pro Gln Thr Pro Lys Glu Lys Ala Glu Ala
    2420                2425                2430

Leu Glu Asp Leu Val Gly Phe Lys Glu Leu Phe Gln Thr Pro Gly
    2435                2440                2445

His Thr Glu Glu Ser Met Thr Asp Asp Lys Ile Thr Glu Val Ser
    2450                2455                2460

Cys Lys Ser Pro Gln Pro Glu Ser Phe Lys Thr Ser Arg Ser Ser
    2465                2470                2475

Lys Gln Arg Leu Lys Ile Pro Leu Val Lys Val Asp Met Lys Glu
    2480                2485                2490

Glu Pro Leu Ala Val Ser Lys Leu Thr Arg Thr Ser Gly Glu Thr
    2495                2500                2505

Thr Gln Thr His Thr Glu Pro Thr Gly Asp Ser Lys Ser Ile Lys
    2510                2515                2520

Ala Phe Lys Glu Ser Pro Lys Gln Ile Leu Asp Pro Ala Ala Ser
    2525                2530                2535

Val Thr Gly Ser Arg Arg Gln Leu Arg Thr Arg Lys Glu Lys Ala
    2540                2545                2550

Arg Ala Leu Glu Asp Leu Val Asp Phe Lys Glu Leu Phe Ser Ala
    2555                2560                2565

Pro Gly His Thr Glu Glu Ser Met Thr Ile Asp Lys Asn Thr Lys
    2570                2575                2580

Ile Pro Cys Lys Ser Pro Pro Pro Glu Leu Thr Asp Thr Ala Thr
    2585                2590                2595

Ser Thr Lys Arg Cys Pro Lys Thr Arg Pro Arg Lys Glu Val Lys
    2600                2605                2610

Glu Glu Leu Ser Ala Val Glu Arg Leu Thr Gln Thr Ser Gly Gln
    2615                2620                2625

Ser Thr His Thr His Lys Glu Pro Ala Ser Gly Asp Glu Gly Ile
    2630                2635                2640

Lys Val Leu Lys Gln Arg Ala Lys Lys Lys Pro Asn Pro Val Glu

-continued

```
            2645                2650                2655

Glu Glu Pro Ser Arg Arg Pro Arg Ala Pro Lys Glu Lys Ala
    2660                2665                2670

Gln Pro Leu Glu Asp Leu Ala Gly Phe Thr Glu Leu Ser Glu Thr
    2675                2680                2685

Ser Gly His Thr Gln Glu Ser Leu Thr Ala Gly Lys Ala Thr Lys
    2690                2695                2700

Ile Pro Cys Glu Ser Pro Pro Leu Glu Val Val Asp Thr Thr Ala
    2705                2710                2715

Ser Thr Lys Arg His Leu Arg Thr Arg Val Gln Lys Val Gln Val
    2720                2725                2730

Lys Glu Glu Pro Ser Ala Val Lys Phe Thr Gln Thr Ser Gly Glu
    2735                2740                2745

Thr Thr Asp Ala Asp Lys Glu Pro Ala Gly Glu Asp Lys Gly Ile
    2750                2755                2760

Lys Ala Leu Lys Glu Ser Ala Lys Gln Thr Pro Ala Pro Ala Ala
    2765                2770                2775

Ser Val Thr Gly Ser Arg Arg Arg Pro Arg Ala Pro Arg Glu Ser
    2780                2785                2790

Ala Gln Ala Ile Glu Asp Leu Ala Gly Phe Lys Asp Pro Ala Ala
    2795                2800                2805

Gly His Thr Glu Glu Ser Met Thr Asp Asp Lys Thr Thr Lys Ile
    2810                2815                2820

Pro Cys Lys Ser Ser Pro Glu Leu Glu Asp Thr Ala Thr Ser Ser
    2825                2830                2835

Lys Arg Arg Pro Arg Thr Arg Ala Gln Lys Val Glu Val Lys Glu
    2840                2845                2850

Glu Leu Leu Ala Val Gly Lys Leu Thr Gln Thr Ser Gly Glu Thr
    2855                2860                2865

Thr His Thr Asp Lys Glu Pro Val Gly Glu Gly Lys Gly Thr Lys
    2870                2875                2880

Ala Phe Lys Gln Pro Ala Lys Arg Lys Leu Asp Ala Glu Asp Val
    2885                2890                2895

Ile Gly Ser Arg Arg Gln Pro Arg Ala Pro Lys Glu Lys Ala Gln
    2900                2905                2910

Pro Leu Glu Asp Leu Ala Ser Phe Gln Glu Leu Ser Gln Thr Pro
    2915                2920                2925

Gly His Thr Glu Glu Leu Ala Asn Gly Ala Ala Asp Ser Phe Thr
    2930                2935                2940

Ser Ala Pro Lys Gln Thr Pro Asp Ser Gly Lys Pro Leu Lys Ile
    2945                2950                2955

Ser Arg Arg Val Leu Arg Ala Pro Lys Val Glu Pro Val Gly Asp
    2960                2965                2970

Val Val Ser Thr Arg Asp Pro Val Lys Ser Gln Ser Lys Ser Asn
    2975                2980                2985

Thr Ser Leu Pro Pro Leu Pro Phe Lys Arg Gly Gly Lys Asp
    2990                2995                3000

Gly Ser Val Thr Gly Thr Lys Arg Leu Arg Cys Met Pro Ala Pro
    3005                3010                3015

Glu Glu Ile Val Glu Glu Leu Pro Ala Ser Lys Lys Gln Arg Val
    3020                3025                3030

Ala Pro Arg Ala Arg Gly Lys Ser Ser Glu Pro Val Val Ile Met
    3035                3040                3045
```

```
Lys Arg  Ser Leu Arg Thr Ser  Ala Lys Arg Ile Glu  Pro Ala Glu
    3050             3055              3060

Glu Leu  Asn Ser Asn Asp Met  Lys Thr Asn Lys Glu  Glu His Lys
    3065             3070              3075

Leu Gln  Asp Ser Val Pro Glu  Asn Lys Gly Ile Ser  Leu Arg Ser
    3080             3085              3090

Arg Arg  Gln Asn Lys Thr Glu  Ala Glu Gln Gln Ile  Thr Glu Val
    3095             3100              3105

Phe Val  Leu Ala Glu Arg Ile  Glu Ile Asn Arg Asn  Glu Lys Lys
    3110             3115              3120

Pro Met  Lys Thr Ser Pro Glu  Met Asp Ile Gln Asn  Pro Asp Asp
    3125             3130              3135

Gly Ala  Arg Lys Pro Ile Pro  Arg Asp Lys Val Thr  Glu Asn Lys
    3140             3145              3150

Arg Cys  Leu Arg Ser Ala Arg  Gln Asn Glu Ser Ser  Gln Pro Lys
    3155             3160              3165

Val Ala  Glu Glu Ser Gly Gly  Gln Lys Ser Ala Lys  Val Leu Met
    3170             3175              3180

Gln Asn  Gln Lys Gly Lys Gly  Glu Ala Gly Asn Ser  Asp Ser Met
    3185             3190              3195

Cys Leu  Arg Ser Arg Lys Thr  Lys Ser Gln Pro Ala  Ala Ser Thr
    3200             3205              3210

Leu Glu  Ser Lys Ser Val Gln  Arg Val Thr Arg Ser  Val Lys Arg
    3215             3220              3225

Cys Ala  Glu Asn Pro Lys Lys  Ala Glu Asp Asn Val  Cys Val Lys
    3230             3235              3240

Lys Ile  Arg Thr Arg Ser His  Arg Asp Ser Glu Asp  Ile
    3245             3250              3255

<210> SEQ ID NO 13
<211> LENGTH: 1355
<212> TYPE: DNA
<213> ORGANISM: Homo sapiens

<400> SEQUENCE: 13
ggatggccgg agctggcgcc ctggttctgg aggtaaccgg ttactgaggg cgagaagcgc    60
cacccggagg ctctagcctg acaaatgctt gctgacctgg gccagagctc ttcccttacg   120
caagtctcag ccggtcgtcg cgacgttcgc ccgctcgctc tgaggctcct gaagccgaaa   180
ccagctagac tttcctcctt cccgcctgcc tgtagcggcg ttgttgccac tccgccacca   240
tgttcgaggc gcgcctggtc cagggctcca tcctcaagaa ggtgttggag cactcaagg    300 acctcatcaa cgaggcctgc tgggatatta gctccagcgg tgtaaacctg cagagcatgg   360
actcgtccca cgtctctttg gtgcagctca ccctgcggtc tgagggcttc gacacctacc   420
gctgcgaccg caacctggcc atgggcgtga acctcaccag tatgtccaaa atactaaaat   480
gcgccggcaa tgaagatatc attacactaa gggccgaaga taacgcggat accttggcgc   540
tagtatttga agcaccaaac caggagaaag tttcagacta tgaaatgaag ttgatggatt   600
tagatgttga caacttgga attccagaac aggagtacag ctgtgtagta agatgccctt   660
ctggtgaatt tgcacgtata tgccgagatc tcagccatat tggagatgct gttgtaattt   720
cctgtgcaaa agacggagtg aaattttctg caagtggaga acttggaaat ggaaacatta   780
aattgtcaca gacaagtaat gtcgataaag aggaggaagc tgttaccata gagatgaatg   840
```

```
aaccagttca actaacttttt gcactgaggt acctgaactt ctttacaaaa gccactccac    900
tctcttcaac ggtgcacactc agtatgtctg cagatgtacc ccttgttgta gagtataaaa    960
ttgcggatat gggacactta aaatactact tggctcccaa gatcgaggat gaagaaggat   1020
cttaggcatt cttaaaattc aagaaaataa aactaagctc tttgagaact gcttctaaga   1080
tgccagcata tactgaagtc ttttctgtca ccaaatttgt acctctaagt acatatgtag   1140
atattgtttt ctgtaaataa cctattttt tctctattct ctgcaatttg tttaaagaat   1200
aaagtccaaa gtcagatctg gtctagttaa cctagaagta ttttttgtctc ttagaaatac   1260 ttgtgatttt tataatacaa aagggtcttg actctaaatg cagttttaag aattgttttt   1320
gaatttaaat aaagttactt gaatttcaaa catca                              1355
```

<210> SEQ ID NO 14
<211> LENGTH: 261
<212> TYPE: PRT
<213> ORGANISM: Homo sapiens

<400> SEQUENCE: 14

```
Met Phe Glu Ala Arg Leu Val Gln Gly Ser Ile Leu Lys Lys Val Leu
 1               5                  10                  15

Glu Ala Leu Lys Asp Leu Ile Asn Glu Ala Cys Trp Asp Ile Ser Ser
                20                  25                  30

Ser Gly Val Asn Leu Gln Ser Met Asp Ser Ser His Val Ser Leu Val
            35                  40                  45

Gln Leu Thr Leu Arg Ser Glu Gly Phe Asp Thr Tyr Arg Cys Asp Arg
        50                  55                  60

Asn Leu Ala Met Gly Val Asn Leu Thr Ser Met Ser Lys Ile Leu Lys
 65                  70                  75                  80

Cys Ala Gly Asn Glu Asp Ile Ile Thr Leu Arg Ala Glu Asp Asn Ala
                85                  90                  95

Asp Thr Leu Ala Leu Val Phe Glu Ala Pro Asn Gln Glu Lys Val Ser
            100                 105                 110

Asp Tyr Glu Met Lys Leu Met Asp Leu Asp Val Glu Gln Leu Gly Ile
        115                 120                 125

Pro Glu Gln Glu Tyr Ser Cys Val Val Lys Met Pro Ser Gly Glu Phe
    130                 135                 140

Ala Arg Ile Cys Arg Asp Leu Ser His Ile Gly Asp Ala Val Val Ile
145                 150                 155                 160

Ser Cys Ala Lys Asp Gly Val Lys Phe Ser Ala Ser Gly Glu Leu Gly
                165                 170                 175

Asn Gly Asn Ile Lys Leu Ser Gln Thr Ser Asn Val Asp Lys Glu Glu
            180                 185                 190

Glu Ala Val Thr Ile Glu Met Asn Glu Pro Val Gln Leu Thr Phe Ala
        195                 200                 205

Leu Arg Tyr Leu Asn Phe Phe Thr Lys Ala Thr Pro Leu Ser Ser Thr
    210                 215                 220

Val Thr Leu Ser Met Ser Ala Asp Val Pro Leu Val Val Glu Tyr Lys
225                 230                 235                 240

Ile Ala Asp Met Gly His Leu Lys Tyr Tyr Leu Ala Pro Lys Ile Glu
                245                 250                 255

Asp Glu Glu Gly Ser
            260
```

<210> SEQ ID NO 15

<211> LENGTH: 238
<212> TYPE: PRT
<213> ORGANISM: Aequorea macrodactyla

<400> SEQUENCE: 15

```
Met Ser Lys Gly Glu Glu Leu Phe Thr Gly Ile Val Pro Val Leu Ile
1               5                   10                  15
Glu Leu Asp Gly Asp Val His Gly His Lys Phe Ser Val Arg Gly Glu
            20                  25                  30
Gly Glu Gly Asp Ala Asp Tyr Gly Lys Leu Glu Ile Lys Phe Ile Cys
        35                  40                  45
Thr Thr Gly Lys Leu Pro Val Pro Trp Pro Thr Leu Val Thr Thr Leu
50                  55                  60
Gly Tyr Gly Ile Gln Cys Phe Ala Arg Tyr Pro Glu His Met Lys Met
65                  70                  75                  80
Asn Asp Phe Phe Lys Ser Ala Met Pro Glu Gly Tyr Ile Gln Glu Arg
                85                  90                  95
Thr Ile Phe Phe Gln Asp Asp Gly Lys Tyr Lys Thr Arg Gly Glu Val
            100                 105                 110
Lys Phe Glu Gly Asp Thr Leu Val Asn Arg Ile Glu Leu Lys Gly Met
        115                 120                 125
Asp Phe Lys Glu Asp Gly Asn Ile Leu Gly His Lys Leu Glu Tyr Asn
    130                 135                 140
Phe Asn Ser His Asn Val Tyr Ile Met Pro Asp Lys Ala Asn Asn Gly
145                 150                 155                 160
Leu Lys Val Asn Phe Lys Ile Arg His Asn Ile Glu Gly Gly Gly Val
                165                 170                 175
Gln Leu Ala Asp His Tyr Gln Thr Asn Val Pro Leu Gly Asp Gly Pro
            180                 185                 190
Val Leu Ile Pro Ile Asn His Tyr Leu Ser Leu Gln Thr Ala Ile Ser
        195                 200                 205
Lys Asp Arg Asn Glu Thr Arg Asp His Met Val Phe Leu Glu Phe Phe
    210                 215                 220
Ser Ala Cys Gly His Thr His Gly Met Asp Glu Leu Tyr Lys
225                 230                 235
```

<210> SEQ ID NO 16
<211> LENGTH: 717
<212> TYPE: DNA
<213> ORGANISM: Aequorea macrodactyla

<400> SEQUENCE: 16

| | | | | |
|---|---|---|---|---|
| atgagtaaag gagaagaact | tttcactggg | attgtcccag | ttctcattga | gttagacggt | 60 |
| gatgtccatg gacataaatt | ctctgtcaga | ggagaagggg | aaggcgatgc | agattatgga | 120 |
| aaacttgaaa tcaaattcat | ttgcactact | ggaaagctac | cagttccatg | gccaacactt | 180 |
| gttactacac tgggctacgg | catccaatgt | ttcgcaagat | acccagaaca | catgaaaatg | 240 |
| aatgacttct tcaagagtgc | catgcctgag | ggttacattc | aagaagaac | catctttttc | 300 |
| caagatgatg gaaaatacaa | gacacgtggt | gaagtcaagt | ttgaaggtga | tactcttgtt | 360 |
| aacagaattg agctcaaagg | tatggacttt | aagaagatg | caatatcct | tggacacaag | 420 |
| ttggagtaca attttaattc | acataatgta | tacattatgc | cggacaaagc | caataatgga | 480 |
| ctcaaagtca atttcaaaat | tagacacaat | atcgaaggtg | gtggtgtcca | acttgctgat | 540 |
| cattaccaaa caaatgttcc | ccttggagac | ggtcctgtcc | ttataccaat | caatcactac | 600 |

```
ctatccttgc aaacagccat ttcaaaagat cgaaatgaga cgagagatca tatggtgttt    660
ctggaatttt tctcagcttg tggacataca catggcatgg atgaactata caaataa       717
```

<210> SEQ ID NO 17
<211> LENGTH: 489
<212> TYPE: PRT
<213> ORGANISM: Artificial sequence
<220> FEATURE:
<223> OTHER INFORMATION: Alkaline phosphatase

<400> SEQUENCE: 17

```
Met Lys Gln Ser Thr Ile Ala Leu Ala Leu Leu Pro Leu Leu Phe Thr
1               5                   10                  15

Pro Val Thr Lys Ala Arg Thr Pro Glu Met Pro Leu Gln Gly Thr Ala
            20                  25                  30

Val Asp Gly Gly Gly Ser Met His Ala Ser Leu Glu Val Leu Glu
        35                  40                  45

Asn Arg Ala Ala Gln Gly Asp Ile Thr Ala Pro Gly Gly Ala Arg Arg
50                  55                  60

Leu Thr Gly Asp Gln Thr Ala Ala Leu Arg Asp Ser Leu Ser Asp Lys
65                  70                  75                  80

Pro Ala Lys Asn Ile Ile Leu Leu Ile Gly Asp Gly Met Gly Asp Ser
                85                  90                  95

Glu Ile Thr Ala Ala Arg Asn Tyr Ala Glu Gly Ala Gly Gly Phe Phe
            100                 105                 110

Lys Gly Ile Asp Ala Leu Pro Leu Thr Gly Gln Tyr Thr His Tyr Ala
        115                 120                 125

Leu Asn Lys Lys Thr Gly Lys Pro Asp Tyr Val Thr Asp Ser Ala Ala
130                 135                 140

Ser Ala Thr Ala Trp Ser Thr Gly Val Lys Thr Tyr Asn Gly Ala Leu
145                 150                 155                 160

Gly Val Asp Ile His Glu Lys Asp His Pro Thr Ile Leu Glu Met Ala
                165                 170                 175

Lys Ala Ala Gly Leu Ala Thr Gly Asn Val Ser Thr Ala Glu Leu Gln
            180                 185                 190

Asp Ala Thr Pro Ala Ala Leu Val Ala His Val Thr Ser Arg Lys Cys
        195                 200                 205

Tyr Gly Pro Ser Ala Thr Ser Glu Lys Cys Pro Gly Asn Ala Leu Glu
210                 215                 220

Lys Gly Gly Lys Gly Ser Ile Thr Glu Gln Leu Leu Asn Ala Arg Ala
225                 230                 235                 240

Asp Val Thr Leu Gly Gly Gly Ala Lys Thr Phe Ala Glu Thr Ala Thr
                245                 250                 255

Ala Gly Glu Trp Gln Gly Lys Thr Leu Arg Glu Gln Ala Gln Ala Arg
            260                 265                 270

Gly Tyr Gln Leu Val Ser Asp Ala Ala Ser Leu Asn Ser Val Thr Glu
        275                 280                 285

Ala Asn Gln Gln Lys Pro Leu Leu Gly Leu Phe Ala Asp Gly Asn Met
290                 295                 300

Pro Val Arg Trp Leu Gly Pro Lys Ala Thr Tyr His Gly Asn Ile Asp
305                 310                 315                 320

Lys Pro Ala Val Thr Cys Thr Pro Asn Pro Gln Arg Asn Asp Ser Val
                325                 330                 335

Pro Thr Leu Ala Gln Met Thr Asp Lys Ala Ile Glu Leu Leu Ser Lys
            340                 345                 350
```

```
Asn Glu Lys Gly Phe Phe Leu Gln Val Glu Gly Ala Ser Ile Asp Lys
            355                 360                 365

Gln Asp His Ala Ala Asn Pro Cys Gly Gln Ile Gly Glu Thr Val Asp
    370                 375                 380

Leu Asp Glu Ala Val Gln Arg Ala Leu Glu Phe Ala Lys Lys Glu Gly
385                 390                 395                 400

Asn Thr Leu Val Ile Val Thr Ala Asp His Ala His Ala Ser Gln Ile
                405                 410                 415

Val Ala Pro Asp Thr Lys Ala Pro Gly Leu Thr Gln Ala Leu Asn Thr
            420                 425                 430

Lys Asp Gly Ala Val Met Val Met Ser Tyr Gly Asn Ser Glu Glu Asp
        435                 440                 445

Ser Gln Glu His Thr Gly Ser Gln Leu Arg Ile Ala Ala Tyr Gly Pro
    450                 455                 460

His Ala Ala Asn Val Val Gly Leu Thr Asp Gln Thr Asp Leu Phe Tyr
465                 470                 475                 480

Thr Met Lys Ala Ala Leu Gly Leu Lys
                485

<210> SEQ ID NO 18
<211> LENGTH: 1470
<212> TYPE: DNA
<213> ORGANISM: Artificial sequence
<220> FEATURE:
<223> OTHER INFORMATION: Alkaline phosphatase coding sequence

<400> SEQUENCE: 18
ttatttcagc cccagagcgg ctttcatggt gtagaagaga tcggtctggt cggtcagtcc      60
aacaacattg gcggcatgcg ggccatacgc cgcaatacgc aactgactgc ggtatgttc     120 ttgtgaatcc tcttcggagt tcccgtaact catcaccatc actgcgccat ctttggtatt    180
tagcgcctgg gtgaggcccg gagctttggt atccggcgca acaatctggc tggcgtgggc    240
gtgatcagcg gtgactatga ccagcgtgtt accctccttt ttagcgaatt ccagcgcccg    300
ttgtacggct tcatcgagat cgaccgtctc gccaatttgc cacaaggat cgcagcatg     360 atcctgttta tcgattgacg caccttcaac ttgcaggaaa aagcctttct cattttact    420 caacaattca atggctttgt cggtcatctg cgccagggtt ggtacactgt cattacgttg    480
cggatttggc gtacaggtga ctgcgggctt atcgatattg ccatggtacg ttgctttcgg    540
tcctagccag cgcactggca tattgccgtc agcaaacagg ccaagcaggg gtttttgctg    600
attcgcttcc gtcaccgaat tcagtgaggc agcatcgctc accaactgat aaccacgcgc    660
ctgtgcctgt tcacgcagcg ttttcccctg ccattcacca gcggttgccg tttcagcaaa    720
ggtttttgcg ccgccgccaa gcgtaacgtc ggcacgagcg ttaagcagct gttcggtaat    780
cgatcctttt ccgccttttt ccagagcgtt accggacat ttttcactgg tcgcgctcgg    840
accgtagcat ttgcgcgagg tcacatgtgc accagcgca gcgggcgtgg catcctgcaa    900
ctctgcggta gaaacgttac cggtcgccag acctgcggct tttgccattt ccagaatcgt    960
tgggtgatct ttttcgtgaa tatcgacgcc cagcgcgccg ttataggttt tgacaccggt   1020
tgaccaggcg gttgctgatg cagccgagtc ggtgacgtag tccggtttgc cggtttttt    1080 attcagcgca tagtgagtgt attgcccggt aagcggtaag gcatctatac ctttaaaaaa   1140 gccgccgca ccttcggcat aattacgtgc ggcagtaatt tccgagtccc ccatcccatc    1200
gccaatcagc aaaataatat tttttgcagg tttatcgcta agagaatcac gcagagcggc   1260
```

```
agtctgatca cccgttaaac ggcgagcacc gccgggtgca gtaatatcgc cctgagcagc    1320
ccggttttcc agaacctcga ggctagcatg catagaaccg ccaccaccgt cgacagcggt    1380
accctgcaga ggcatttctg tgtccgggc ttttgtcaca ggggtaaaca gtaacggtaa     1440
gagtgccagt gcaatagtgc tttgtttcac                                     1470
```

<210> SEQ ID NO 19
<211> LENGTH: 334
<212> TYPE: PRT
<213> ORGANISM: Arabidopsis thaliana

<400> SEQUENCE: 19

| | | | | | | | | | | | | | | |
|---|---|---|---|---|---|---|---|---|---|---|---|---|---|---|
|Met|Ser|Asn|Met|Gln|Phe|Ser|Arg|Gly|Phe|Asn|Pro|Phe|Val|Ile|Leu|
|1| | | |5| | | | |10| | | | |15| |
|Phe|Cys|Leu|Ala|Val|Val|Ala|Pro|Ile|Ile|Ser|Ala|Asp|Val|Ala|Ile|
| | | |20| | | | |25| | | | |30| | |
|Leu|Arg|Thr|Asp|Tyr|Tyr|Gln|Lys|Thr|Cys|Pro|Asp|Phe|His|Lys|Ile|
| | |35| | | | |40| | | | |45| | | |
|Val|Arg|Glu|Ala|Val|Thr|Thr|Lys|Gln|Val|Gln|Gln|Pro|Thr|Thr|Ala|
|50| | | | |55| | | | |60| | | | | |
|Ala|Gly|Thr|Leu|Arg|Leu|Phe|Phe|His|Asp|Cys|Phe|Leu|Glu|Gly|Cys|
|65| | | | |70| | | | |75| | | | |80|
|Asp|Ala|Ser|Val|Leu|Ile|Ala|Thr|Asn|Ser|Phe|Asn|Lys|Ala|Glu|Arg|
| | | | |85| | | | |90| | | | |95| |
|Asp|Asp|Asp|Leu|Asn|Asp|Ser|Leu|Pro|Gly|Asp|Ala|Phe|Asp|Ile|Val|
| | | |100| | | | |105| | | | |110| | |
|Thr|Arg|Ile|Lys|Thr|Ala|Leu|Glu|Leu|Ser|Cys|Pro|Gly|Val|Val|Ser|
| | |115| | | | |120| | | | |125| | | |
|Cys|Ala|Asp|Ile|Leu|Ala|Gln|Ala|Thr|Arg|Asp|Leu|Val|Thr|Met|Val|
| |130| | | | |135| | | | |140| | | | |
|Gly|Gly|Pro|Tyr|Phe|Asp|Val|Lys|Leu|Gly|Arg|Lys|Asp|Gly|Phe|Glu|
|145| | | | |150| | | | |155| | | | |160|
|Ser|Lys|Ala|His|Lys|Val|Arg|Gly|Asn|Val|Pro|Met|Ala|Asn|Gln|Thr|
| | | | |165| | | | |170| | | | |175| |
|Val|Pro|Asp|Ile|His|Gly|Ile|Phe|Lys|Lys|Asn|Gly|Phe|Ser|Leu|Arg|
| | | |180| | | | |185| | | | |190| | |
|Glu|Met|Val|Ala|Leu|Ser|Gly|Ala|His|Thr|Ile|Gly|Phe|Ser|His|Cys|
| | |195| | | | |200| | | | |205| | | |
|Lys|Glu|Phe|Ser|Asp|Arg|Leu|Tyr|Gly|Ser|Arg|Ala|Asp|Lys|Glu|Ile|
| |210| | | | |215| | | | |220| | | | |
|Asn|Pro|Arg|Phe|Ala|Ala|Leu|Lys|Asp|Leu|Cys|Lys|Asn|His|Thr|
|225| | | | |230| | | | |235| | | | |240|
|Val|Asp|Asp|Thr|Ile|Ala|Ala|Phe|Asn|Asp|Val|Met|Thr|Pro|Gly|Lys|
| | | | |245| | | | |250| | | | |255| |
|Phe|Asp|Asn|Met|Tyr|Phe|Lys|Asn|Leu|Lys|Arg|Gly|Leu|Gly|Leu|Leu|
| | | |260| | | | |265| | | | |270| | |
|Ala|Ser|Asp|His|Ile|Leu|Ile|Lys|Asp|Asn|Ser|Thr|Lys|Pro|Phe|Val|
| | |275| | | | |280| | | | |285| | | |
|Asp|Leu|Tyr|Ala|Thr|Asn|Glu|Thr|Ala|Phe|Phe|Glu|Asp|Phe|Ala|Arg|
| |290| | | | |295| | | | |300| | | | |
|Ala|Met|Glu|Lys|Leu|Gly|Thr|Val|Gly|Val|Lys|Gly|Asp|Lys|Asp|Gly|
|305| | | | |310| | | | |315| | | | |320|
|Glu|Val|Arg|Arg|Arg|Cys|Asp|His|Phe|Asn|Asn|Leu|Asn|Val|
| | | | |325| | | | |330| | | | | |

<210> SEQ ID NO 20
<211> LENGTH: 1390
<212> TYPE: DNA
<213> ORGANISM: Arabidopsis thaliana

<400> SEQUENCE: 20

```
ctcttcttag taacctccta agccatgaaa tagtcgcaaa ggccctttct tcgtcttcgt      60
ttctaattgc tttcgacgac aatcgatcgt agagaagtct acctcgtaga catctctctc     120
acaaatccaa ttcaattacc attgtttgtt attatctgat gtcgaatatg caattctctc     180
gtggttttaa tcccttttgtt atcctcttct gtctcgccgt ggttgcacca attatatcgg    240
ctgatgtcgc tatcttgaga acggactatt accaaaaaac atgtcctgat tccacaaaa     300
ttgtgcgtga agccgttaca accaaacaag tccaacaacc aacaactgcg gccgggaccc    360
tccgtctctt tttccatgat tgtttccttg aaggttgtga tgcatctgtc ttgatcgcga    420
ccaactcgtt caacaaagcg gaacgcgatg atgatctcaa tgattccctc ccgggagatg    480
cttttgacat cgtcacccgc atcaagacag ctctcgagtt gtcttgtcct ggtgtagtat    540
catgcgcgga tattctagcg caggctacac gtgaccttgt cacaatggta ggaggacctt    600
actttgacgt aaagcttggt cgtaaagacg gattcgaatc caaagctcat aaagtcagag    660
gaaatgtccc aatggcaaac cagactgttc ctgacatcca cgggatattc aagaaaaacg    720
gttttagtct tcgcgagatg gtagcattaa gcggggctca ccattgga ttctctcact      780
gcaaagagtt ttccgacaga ctctacggat cccgtgctga taagaaatc aacccgcgat     840
tcgcagccgc tctcaaagat cttttgcaaaa accacaccgt ggatgataca atcgccgcgt   900
ttaacgacgt gatgactcca ggaaagttcg acaacatgta cttcaagaac ctaaagcgag    960
ggctagggct tttagcgtct gaccacatcc ttattaaaga caacagcacc aagccgtttg   1020
tggatctata cgcaactaac gagacagcat tctttgagga tttcgctcgt gcgatggaga  1080
aacttggcac ggtcggcgtc aagggcgata agatggaga agtgagacgt aggtgcgacc   1140
acttcaacaa tctcaacgtt taagaagaaa aagaaaacac aaaaccatat aaatataata  1200
ttatttctgt tttatttgcg gaggagttga ggagaagaaa ggtttggttg gtatatatgt  1260
ttaataacta cctattataa gcaagatctt gtaacaattc aagttgggat gtttaatttt  1320
tccatgaaaa ttcaaactgt tgtattgaaa gtatatagat aaaataacat attatatatc  1380
gaacaattgt                                                          1390
```

<210> SEQ ID NO 21
<211> LENGTH: 286
<212> TYPE: PRT
<213> ORGANISM: Artificial sequence
<220> FEATURE:
<223> OTHER INFORMATION: Recombinant construct

<400> SEQUENCE: 21

```
Gln Ser Val Leu Thr Gln Pro Pro Ser Val Ser Gly Ser Pro Gly Gln
1               5                   10                  15

Ser Ile Thr Ile Ser Cys Thr Gly Thr Ser Ser Asp Ile Gly Thr Tyr
            20                  25                  30

Lys Ile Val Ser Trp Tyr Gln Gln His Pro Gly Lys Ala Pro Lys Leu
        35                  40                  45

Met Ile Tyr Asp Val Asn Gln Arg Pro Ser Gly Val Ser Asp Arg Phe
    50                  55                  60
```

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Gly
                85                  90                  95

Ser Thr Leu Val Phe Gly Gly Gly Thr Lys Leu Thr Val Leu Gly Ser
            100                 105                 110

Ser Gly Gly Gly Gly Ser Gly Gly Gly Gly Ser Gly Gly Ser Ala Leu
        115                 120                 125

Gln Val Gln Leu Gln Gln Ser Gly Ala Glu Val Lys Lys Pro Gly Glu
    130                 135                 140

Ser Leu Lys Ile Ser Cys Lys Gly Ser Gly Tyr Ser Phe Thr Ser Tyr
145                 150                 155                 160

Trp Ile Gly Trp Val Arg Gln Met Pro Gly Lys Gly Leu Glu Trp Met
                165                 170                 175

Gly Ile Ile Tyr Pro Gly Asp Ser Asp Thr Arg Tyr Ser Pro Ser Phe
            180                 185                 190

Gln Gly Gln Val Thr Ile Ser Ala Asp Lys Ser Ile Ser Thr Ala Tyr
        195                 200                 205

Leu Gln Trp Ser Ser Leu Lys Ala Ser Asp Thr Ala Met Tyr Tyr Cys
    210                 215                 220

Ala Arg His Arg Ala Ala Ser Gly Ser Pro Asp Ala Cys Asp Tyr Trp
225                 230                 235                 240

Gly Gln Gly Thr Leu Val Thr Val Ser Ser Gly Ser Ala Ser Ala Pro
                245                 250                 255

Thr Leu Phe Pro Ala Ala Ala His His His His His Gly Ala Ala
            260                 265                 270

Glu Gln Lys Leu Ile Ser Glu Glu Asp Leu Asn Gly Ala Ala
        275                 280                 285

<210> SEQ ID NO 22
<211> LENGTH: 861
<212> TYPE: DNA
<213> ORGANISM: Artificial sequence
<220> FEATURE:
<223> OTHER INFORMATION: Recombinant construct

<400> SEQUENCE: 22
cagtctgtgt tgacgcagcc gccctcagtg tctgggtctc ctggacagtc gatcaccatc      60
tcctgcactg gaaccagcag tgatattggg acttataaaa ttgtctcctg gtaccaacag     120
cacccctggc aagcccccaa actcatgatt tatgacgtca atcagcggcc ctcaggggtt     180
tctgatcgct tctctggctc caagtctggc aacacggcct ccctgacaat ctctgggctc     240
caggctgagg acgaggctga ttattactgc agctcatata caagcggcag cactctggta     300
ttcggcgggg ggaccaagct gaccgtccta ggctcgagtg gtggaggcgg ttcaggcgga     360
ggtggctctg gcggtagtgc acttcaggta cagctgcagc agtcaggagc agaggtgaaa     420
aagcccgggg agtctctgaa gatctcctgt aagggttctg gatacagctt taccagctac     480
tggatcggct gggtgcgcca gatgcccggg aaaggcctgg agtggatggg gatcatctat     540
cctggtgact ctgataccag atacagcccg tccttccaag ccaggtcac catctcagcc     600 gacaagtcca tcagcaccgc ctacctgcag tggagcagcc tgaaggcctc ggacaccgcc     660
atgtattact gtgcgagaca tcgggccgct agtgggagcc cggacgcgtg tgactactgg     720
ggccagggaa ccctggtcac cgtctcctca gggagtgcat ccgccccaac ccttttcccc     780
gcggccgcac atcatcatca ccatcacggg gccgcagaac aaaaactcat ctcagaagag     840
gatctgaatg gggccgcata g 861

<210> SEQ ID NO 23
<211> LENGTH: 328
<212> TYPE: PRT
<213> ORGANISM: Clostridium perfringens

<400> SEQUENCE: 23

| | | | | | | | | | | | | | | | |
|---|---|---|---|---|---|---|---|---|---|---|---|---|---|---|---|
| Met | Ser | Val | Lys | Glu | Ser | Val | Leu | Lys | Ile | Leu | Glu | Glu | Asn | Arg | Glu |
| 1 | | | | 5 | | | | | 10 | | | | | 15 | |
| Arg | Ser | Ile | Ser | Gly | Glu | Glu | Leu | Ala | Lys | His | Leu | Ser | Val | Ser | Arg |
| | | | 20 | | | | | 25 | | | | | 30 | | |
| Ala | Ala | Ile | Trp | Lys | Ala | Ile | Lys | Ser | Leu | Arg | Gly | Glu | Gly | Tyr | Asn |
| | | | 35 | | | | 40 | | | | | 45 | | | |
| Ile | Ser | Ala | Val | Thr | Asn | Arg | Gly | Tyr | Gln | Leu | Thr | Lys | Asp | Asn | Asp |
| | 50 | | | | | 55 | | | | | 60 | | | | |
| Leu | Ile | Ser | Ala | Glu | Gly | Ile | Lys | Ile | Phe | Leu | Asn | Pro | Lys | Tyr | Arg |
| 65 | | | | | 70 | | | | | 75 | | | | | 80 |
| Glu | Asn | Tyr | Ile | Arg | Val | Tyr | Lys | Thr | Ile | Asp | Ser | Thr | Asn | Gln | Glu |
| | | | | 85 | | | | | 90 | | | | | 95 | |
| Ala | Lys | Lys | Leu | Leu | Met | Asp | Asn | Asp | Ile | Pro | His | Gly | Thr | Ile | Leu |
| | | | 100 | | | | | 105 | | | | | 110 | | |
| Ile | Ala | Glu | Glu | Gln | Thr | Ala | Gly | Arg | Gly | Arg | Phe | Gln | Arg | Lys | Phe |
| | | | 115 | | | | | 120 | | | | | 125 | | |
| Phe | Ser | Pro | Ser | Asn | Lys | Gly | Ile | Tyr | Met | Ser | Val | Ile | Leu | Arg | Pro |
| | | 130 | | | | | 135 | | | | | 140 | | | |
| Asn | Ile | Glu | Leu | Ser | Lys | Ala | Ile | His | Ile | Thr | Thr | Ser | Ala | Ala | Ile |
| 145 | | | | | 150 | | | | | 155 | | | | | 160 |
| Ser | Val | Cys | Arg | Ala | Ile | Glu | Thr | Leu | Thr | Lys | Lys | Arg | Pro | Lys | Ile |
| | | | | 165 | | | | | 170 | | | | | 175 | |
| Lys | Trp | Val | Asn | Asp | Ile | Phe | Leu | Asp | Asp | Lys | Lys | Ile | Cys | Gly | Ile |
| | | | | 180 | | | | | 185 | | | | | 190 | |
| Leu | Thr | Glu | Ala | Thr | Gly | Asn | Phe | Glu | Ser | Gly | Arg | Val | Glu | Asn | Val |
| | | | 195 | | | | | 200 | | | | | 205 | | |
| Val | Val | Gly | Ile | Gly | Val | Asn | Phe | Lys | Thr | Asp | Ser | Lys | Asp | Phe | Pro |
| | 210 | | | | | 215 | | | | | 220 | | | | |
| Glu | Asp | Ile | Lys | Asn | Ile | Ala | Gly | Ser | Val | Phe | Gly | Gly | Glu | Lys | Pro |
| 225 | | | | | 230 | | | | | 235 | | | | | 240 |
| Thr | Ile | Thr | Arg | Asn | Gln | Leu | Val | Ala | Glu | Ile | Leu | Asn | Glu | Leu | Phe |
| | | | | 245 | | | | | 250 | | | | | 255 | |
| Glu | Leu | Cys | Glu | Asn | Leu | Glu | Asp | Lys | Ser | Ile | Met | Thr | Glu | Tyr | Arg |
| | | | 260 | | | | | 265 | | | | | 270 | | |
| Ile | Leu | Ser | Leu | Val | Leu | Gly | Lys | Glu | Val | Ser | Phe | Leu | Lys | Asn | Asn |
| | | | 275 | | | | | 280 | | | | | 285 | | |
| Lys | Leu | Asn | Lys | Gly | Leu | Ala | Ile | Asp | Ile | Thr | Asp | Glu | Gly | Ala | Leu |
| | | 290 | | | | | 295 | | | | | 300 | | | |
| Val | Val | Lys | Tyr | Glu | Asn | Gly | Glu | Ile | Glu | Tyr | Leu | Asn | Ser | Gly | Glu |
| 305 | | | | | 310 | | | | | 315 | | | | | 320 |
| Val | Ser | Val | Lys | Thr | Leu | Asn | Lys | | | | | | | | |
| | | | | 325 | | | | | | | | | | | |

<210> SEQ ID NO 24
<211> LENGTH: 987
<212> TYPE: DNA
<213> ORGANISM: Clostridium perfringens

<400> SEQUENCE: 24

```
atgtcggtta aagagtcagt acttaagatt ctagaagaaa atagggagag aagtatatca      60
ggagaagaat tggctaaaca tttatcagtt tctagggcag ctatatggaa ggctataaaa     120
tccttaaggg gagagggcta caatatttct gctgttacca atagaggata tcaattaaca     180
aaggataatg acttaatatc agcagaggga ataaaaatat ttttaaatcc taaataccgt     240
gaaaactata aagggtgta taaaactata gattcaacta atcaagaagc taagaagctt      300
ttaatggata atgatatacc acatggaacc atattaattg cagaggaaca aacagcaggt     360
agggggagat ttcaaagaaa gttcttttca ccttctaaca aaggaatata tatgagtgtt     420
attttaagac ctaacataga actttcaaag gccatacata taacaacctc agcagccata     480
tctgtttgta gggcaataga acattaact aaaaaagac ctaaaataaa gtgggttaat       540
gatatatttt tagatgataa aaaaatttgc ggcatattaa cagaggcaac aggaaacttt     600
gagagtggaa gagttgaaaa tgttgttgtt ggaattggag tgaattttaa aactgattca     660
aaagatttcc ctgaagatat aaaaatatt gcaggatcag tatttggagg agaaaagcca      720
actattacta gaaatcagtt agttgctgag attttaaatg aacttttga attatgtgaa      780
aatctagagg ataaaagcat aatgacagag tatagaattt tatctttagt attaggaaaa     840
gaagtaagtt ttttaaagaa taataagctg aataaaggat tggcaattga tattactgat     900
gagggagctt tggttgttaa gtatgaaaat ggtgaaatag aatacttaaa ttcaggtgaa     960
gtatcagtaa aaacattaaa taagtaa                                        987
```

<210> SEQ ID NO 25
<211> LENGTH: 238
<212> TYPE: PRT
<213> ORGANISM: Aequorea macrodactyla

<400> SEQUENCE: 25

```
Met Ser Lys Gly Glu Glu Leu Phe Thr Gly Val Val Pro Ile Leu Val
1               5                   10                  15

Glu Leu Asp Gly Asp Val His Gly His Lys Phe Ser Val Arg Gly Glu
            20                  25                  30

Gly Glu Gly Asp Ala Asp Tyr Gly Lys Leu Glu Ile Lys Phe Ile Cys
        35                  40                  45

Thr Thr Gly Lys Leu Pro Val Pro Trp Pro Thr Leu Val Thr Thr Leu
    50                  55                  60

Gly Tyr Gly Ile Leu Cys Phe Ala Arg Tyr Pro Glu His Met Lys Met
65                  70                  75                  80

Asn Asp Phe Phe Lys Ser Ala Met Pro Glu Gly Tyr Ile Gln Glu Arg
                85                  90                  95

Thr Ile Phe Phe Gln Asp Asp Gly Lys Tyr Lys Thr Arg Gly Glu Val
            100                 105                 110

Lys Phe Glu Gly Asp Thr Leu Val Asn Arg Ile Glu Leu Lys Gly Met
        115                 120                 125

Asp Phe Lys Glu Asp Gly Asn Ile Leu Gly His Lys Leu Glu Tyr Asn
    130                 135                 140

Phe Asn Ser His Asn Val Tyr Ile Met Pro Asp Lys Ala Asn Asn Gly
145                 150                 155                 160

Leu Lys Val Asn Phe Lys Ile Arg His Asn Ile Glu Gly Gly Gly Val
                165                 170                 175

Gln Leu Ala Asp His Tyr Gln Thr Asn Val Pro Leu Gly Asp Gly Pro
```

```
                180             185             190
Val Leu Ile Pro Ile Asn His Tyr Leu Ser Tyr Gln Thr Ala Ile Ser
            195                 200                 205

Lys Asp Arg Asn Glu Thr Arg Asp His Met Val Phe Leu Glu Phe Phe
        210                 215                 220

Ser Ala Cys Gly His Thr His Gly Met Asp Glu Leu Tyr Lys
225                 230                 235

<210> SEQ ID NO 26
<211> LENGTH: 717
<212> TYPE: DNA
<213> ORGANISM: Aequorea macrodactyla

<400> SEQUENCE: 26
atgagtaaag gagaagaact tttcactgga gttgtcccaa ttcttgttga attagatggt      60
gatgtccatg gacataaatt ctctgtcaga ggagaagggg aaggcgatgc agattatgga     120
aaacttgaaa tcaaattcat ttgcactact ggaaagctac cagttccatg gccaacactt     180
gttactacac tgggctatgg catcctatgt ttcgcaagat acccagaaca catgaaaatg     240
aatgacttct tcaagagtgc catgcctgag ggttacattc aagaaagaac catcttttc      300 caagatgatg gaaaatacaa gacacgtggt gaagtcaagt ttgaaggtga tactcttgtt     360
aacagaattg agctcaaagg tatggacttt aaagaagatg caatatcct tggacacaag      420 ttggagtaca attttaactc acataatgta tacattatgc cggacaaagc caataatgga     480
ctcaaagtca atttcaaaat tagacacaat atcgaaggtg gtggtgtcca actcgctgat     540
cattaccaaa caaatgttcc ccttggagac ggtcctgtcc ttataccaat caatcactac     600
ctatcctatc aaacagccat ttcaaaagat cgaaatgaga cgagagatca tatggtgttt     660
ctggaatttt tctcagcttg tggacataca catggcatgg atgaactata caaataa       717

<210> SEQ ID NO 27
<211> LENGTH: 741
<212> TYPE: PRT
<213> ORGANISM: Arabidopsis thaliana

<400> SEQUENCE: 27

Met Asn Arg Val Thr Thr Glu Ser Ile Ala Ser Thr Ala Ile Leu Val
1               5                   10                  15

Val Met Val Phe Leu Phe Ser Trp Arg Ser Ile Glu Ala Ala Asn Val
            20                  25                  30

Ser Tyr Asp His Arg Ser Leu Thr Ile Gly Asn Arg Arg Gln Leu Ile
        35                  40                  45

Ile Ser Ala Ala Ile His Tyr Pro Arg Ser Val Pro Ala Met Trp Pro
    50                  55                  60

Ser Leu Val Gln Thr Ala Lys Glu Gly Gly Cys Asn Ala Ile Glu Ser
65                  70                  75                  80

Tyr Val Phe Trp Asn Gly His Glu Pro Ser Pro Gly Lys Tyr Tyr Phe
                85                  90                  95

Gly Gly Arg Tyr Asn Ile Val Lys Phe Ile Lys Ile Val Gln Gln Ala
            100                 105                 110

Gly Met His Met Ile Leu Arg Ile Gly Pro Phe Val Ala Ala Glu Trp
        115                 120                 125

Asn Tyr Gly Gly Val Pro Val Trp Leu His Tyr Val Pro Gly Thr Val
    130                 135                 140

Phe Arg Ala Asp Asn Glu Pro Trp Lys His Tyr Met Glu Ser Phe Thr
```

-continued

```
            145                 150                 155                 160
        Thr Tyr Ile Val Asn Leu Leu Lys Gln Glu Lys Leu Phe Ala Pro Gln
                        165                 170                 175
        Gly Gly Pro Ile Ile Leu Ser Gln Val Glu Asn Glu Tyr Gly Tyr Tyr
                        180                 185                 190
        Glu Lys Asp Tyr Gly Glu Gly Lys Arg Tyr Ala Gln Trp Ser Ala
                        195                 200                 205
        Ser Met Ala Val Ser Gln Asn Ile Gly Val Pro Trp Met Met Cys Gln
        210                 215                 220
        Gln Trp Asp Ala Pro Thr Val Ile Ser Thr Cys Asn Gly Phe Tyr
        225                 230                 235                 240
        Cys Asp Gln Phe Thr Pro Asn Thr Pro Asp Lys Pro Lys Ile Trp Thr
                        245                 250                 255
        Glu Asn Trp Pro Gly Trp Phe Lys Thr Phe Gly Gly Arg Asp Pro His
                        260                 265                 270
        Arg Pro Ala Glu Asp Val Ala Tyr Ser Val Ala Arg Phe Phe Gly Lys
                        275                 280                 285
        Gly Gly Ser Val His Asn Tyr Tyr Met Tyr His Gly Gly Thr Asn Phe
                        290                 295                 300
        Gly Arg Thr Ser Gly Gly Pro Phe Ile Thr Thr Ser Tyr Asp Tyr Glu
        305                 310                 315                 320
        Ala Pro Ile Asp Glu Tyr Gly Leu Pro Arg Leu Pro Lys Trp Gly His
                        325                 330                 335
        Leu Lys Asp Leu His Lys Ala Ile Met Leu Ser Glu Asn Leu Leu Ile
                        340                 345                 350
        Ser Gly Glu His Gln Asn Phe Thr Leu Gly His Ser Leu Glu Ala Asp
                        355                 360                 365
        Val Tyr Thr Asp Ser Ser Gly Thr Cys Ala Ala Phe Leu Ser Asn Leu
                        370                 375                 380
        Asp Asp Lys Asn Asp Lys Ala Val Met Phe Arg Asn Thr Ser Tyr His
        385                 390                 395                 400
        Leu Pro Ala Trp Ser Val Ser Ile Leu Pro Asp Cys Lys Thr Glu Val
                        405                 410                 415
        Phe Asn Thr Ala Lys Val Thr Ser Lys Ser Ser Lys Val Glu Met Leu
                        420                 425                 430
        Pro Glu Asp Leu Lys Ser Ser Ser Gly Leu Lys Trp Glu Val Phe Ser
                        435                 440                 445
        Glu Lys Pro Gly Ile Trp Gly Ala Ala Asp Phe Val Lys Asn Glu Leu
                        450                 455                 460
        Val Asp His Ile Asn Thr Thr Lys Asp Thr Thr Asp Tyr Leu Trp Tyr
        465                 470                 475                 480
        Thr Thr Ser Ile Thr Val Ser Glu Asn Glu Ala Phe Leu Lys Lys Gly
                        485                 490                 495
        Ser Ser Pro Val Leu Phe Ile Glu Ser Lys Gly His Thr Leu His Val
                        500                 505                 510
        Phe Ile Asn Lys Glu Tyr Leu Gly Thr Ala Thr Gly Asn Gly Thr His
                        515                 520                 525
        Val Pro Phe Lys Leu Lys Lys Pro Val Ala Leu Lys Ala Gly Glu Asn
                        530                 535                 540
        Asn Ile Asp Leu Leu Ser Met Thr Val Gly Leu Ala Asn Ala Gly Ser
        545                 550                 555                 560
        Phe Tyr Glu Trp Val Gly Ala Gly Leu Thr Ser Val Ser Ile Lys Gly
                        565                 570                 575
```

```
Phe Asn Lys Gly Thr Leu Asn Leu Thr Asn Ser Lys Trp Ser Tyr Lys
            580                 585                 590
Leu Gly Val Glu Gly Glu His Leu Glu Leu Phe Lys Pro Gly Asn Ser
        595                 600                 605
Gly Ala Val Lys Trp Thr Val Thr Thr Lys Pro Pro Lys Lys Gln Pro
    610                 615                 620
Leu Thr Trp Tyr Lys Val Val Ile Glu Pro Ser Gly Ser Glu Pro
625                 630                 635                 640
Val Gly Leu Asp Met Ile Ser Met Gly Lys Gly Met Ala Trp Leu Asn
                645                 650                 655
Gly Glu Glu Ile Gly Arg Tyr Trp Pro Arg Ile Ala Arg Lys Asn Ser
            660                 665                 670
Pro Asn Asp Glu Cys Val Lys Glu Cys Asp Tyr Arg Gly Lys Phe Met
        675                 680                 685
Pro Asp Lys Cys Leu Thr Gly Cys Gly Glu Pro Ser Gln Arg Trp Tyr
    690                 695                 700
His Val Pro Arg Ser Trp Phe Lys Ser Ser Gly Asn Glu Leu Val Ile
705                 710                 715                 720
Phe Glu Glu Lys Gly Gly Asn Pro Met Lys Ile Lys Leu Ser Lys Arg
                725                 730                 735
Lys Val Ser Val Val
            740

<210> SEQ ID NO 28
<211> LENGTH: 2226
<212> TYPE: DNA
<213> ORGANISM: Arabidopsis thaliana

<400> SEQUENCE: 28
atgaatcggg ttactactga aagcattgcg tctacggcga tactggtggt gatggtgttt     60
ctcttctcgt ggagatctat cgaggcggcg aatgtatcct acgaccaccg ttctctcacc    120
atcggcaatc gccgtcagct cattatctcc gccgccattc actatcccag aagcgtccct    180
gctatgtggc catctcttgt tcaaacagca aagaaggag gctgcaacgc aatcgagtct    240
tatgtcttct ggaatggcca tgagccatct cctggaaagt attattttgg tggccggtat    300
aatatagtga agtttatcaa gattgttcaa caagctggaa tgcatatgat tctacgaatt    360
ggtcctttg ttgccgccga gtggaattac ggggagtcc cggtttggct gcattacgtg    420
ccaggaacag tcttcagagc ggataatgag ccatggaagc attacatgga gagtttcacg    480
acgtatatag taaacctgtt gaaacaagag aagcttttg cacctcaggg cggtccaata    540
atcttgtctc aggtggaaaa cgagtacggg tattatgaaa aggattacgg agaaggaggg    600
aaaaggtatg ctcaatggtc tgcttctatg gctgtttcac agaatattgg tgttccatgg    660
atgatgtgcc agcaatggga tgctcctccc actgtgatta gtacctgcaa tggcttttac    720
tgtgaccaat tcacacctaa taccagat aaacccaaga tttggactga aactggcct    780
ggatggttta aaacttttgg aggcagagac cctcacagac cagcagagga tgtagcctac    840
tctgttgctc ggttttcgg gaaggtgga agtgttcaca actactacat gtatcacgga    900
ggaactaatt ttggacgtac ttcaggagga ccttttatca ctacaagcta tgactatgaa    960
gctcccatcg atgagtatgg attgcctaga ttaccaaat ggggacacct taaggatctc   1020
cacaaagcta taatgctctc tgaaaacttg ctgataagtg cgagcatca aaattttaca   1080
ttaggccatt cactcgaggc tgatgtgtac acagactctt cggaacttg tgctgcgttt   1140
```

-continued

```
ctgtcaaact tggatgataa aaatgacaag gcggtgatgt ttcgaaacac atcataccac   1200
ttgcctgctt ggtcagttag cattctacct gactgcaaga ccgaggtttt caacacagca   1260
aaggtaactt cgaagtcctc caaggttgaa atgctacctg aagatttgaa atcttcatca   1320
ggtcttaaat gggaagtatt ctcggagaaa ccgggtattt ggggcgcagc agattttgtg   1380
aaaaatgaac ttgttgacca catcaacacc acaaaggaca caactgacta tctttggtac   1440
acaacaagta taacagtcag tgaaaatgaa gcgttcttga agaaaggaag ctccccggtt   1500
ctgtttattg aatcaaaagg gcatactctt catgttttca tcaacaaaga gtacttagga   1560
actgcgacag ggaatgggac tcatgtgcct ttcaaactca agaaaccagt tgctctcaaa   1620
gcgggcgaaa acaatattga tttgcttagc atgactgttg gtctagcgaa tgcaggatcc   1680
ttttacgaat gggttggagc tggacttaca agcgtctcaa tcaaaggttt caacaagggc   1740
acattgaatt tgacaaacag caaatggtcc tacaagctcg gcgtggaagg agagcatcta   1800
gaactgttca agccaggtaa ctccgggggct gtgaaatgga cggtgactac gaaacctccc   1860
aagaaacagc ctctgacttg gtataaggtt gtgatagagc caccttctgg gagtgagccg   1920
gttgggcttg atatgatcag tatggggaaa ggaatggcat ggttaaatgg tgaaagagta   1980
ggaagatatt ggcccaggat tgctagaaag aacagcccga acgacgagtg cgtaaaagaa   2040
tgcgattaca gaggcaaatt catgccggat aaatgcctaa ctggatgtgg agagccatct   2100
cagagatggt atcatgttcc aagatcatgg tttaagtctt ccgggaatga gctggtgatc   2160
ttcgaggaga aaggcggcaa tcccatgaag ataaagttgt ccaaaaggaa agtatcggtg   2220
gtgtaa                                                              2226
```

<210> SEQ ID NO 29
<211> LENGTH: 159
<212> TYPE: PRT
<213> ORGANISM: Artificial sequence
<220> FEATURE:
<223> OTHER INFORMATION: Streptavidin

<400> SEQUENCE: 29

```
Asp Pro Ser Lys Asp Ser Lys Ala Gln Val Ser Ala Ala Glu Ala Gly
1               5                   10                  15

Ile Thr Gly Thr Trp Tyr Asn Gln Leu Gly Ser Thr Phe Ile Val Thr
            20                  25                  30

Ala Gly Ala Asp Gly Ala Leu Thr Gly Thr Tyr Glu Ser Ala Val Gly
        35                  40                  45

Asn Ala Glu Ser Arg Tyr Val Leu Thr Gly Arg Tyr Asp Ser Ala Pro
    50                  55                  60

Ala Thr Asp Gly Ser Gly Thr Ala Leu Gly Trp Thr Val Ala Trp Lys
65                  70                  75                  80

Asn Asn Tyr Arg Asn Ala His Ser Ala Thr Thr Trp Ser Gly Gln Tyr
                85                  90                  95

Val Gly Gly Ala Glu Ala Arg Ile Asn Thr Gln Trp Leu Leu Thr Ser
            100                 105                 110

Gly Thr Thr Glu Ala Asn Ala Trp Lys Ser Thr Leu Val Gly His Asp
        115                 120                 125

Thr Phe Thr Lys Val Lys Pro Ser Ala Ala Ser Ile Asp Ala Ala Lys
    130                 135                 140

Lys Ala Gly Val Asn Asn Gly Asn Pro Leu Asp Ala Val Gln Gln
145                 150                 155
```

-continued

```
<210> SEQ ID NO 30
<211> LENGTH: 480
<212> TYPE: DNA
<213> ORGANISM: Artificial sequence
<220> FEATURE:
<223> OTHER INFORMATION: Streptavidin coding sequence

<400> SEQUENCE: 30
gacccgagca aagattctaa agcacaagta tctgctgcag aagcaggaat tacaggcaca      60
tggtataatc agctgggatc tacatttatt gttacagccg gcgcagatgg agctcttaca    120
ggaacatatg aatctgctgt tggaaatgca gaatctagat acgtgcttac aggaagatat    180
gattctgcac ctgcaacaga tggatccgga acagcacttg gatggacagt tgcatggaaa    240
aacaattata gaaacgcaca tagcgctaca acatggtctg gccaatatgt gggaggtgca    300
gaagcaagaa ttaacacaca atggcttttta acatctggaa caacagaagc aaatgcatgg    360
aaaagtactc ttgttggaca tgatacattt acaaaagtta aacctagcgc agcatctatc    420
gatgcagcga aaaagcagg agttaacaat ggcaatcctt tagatgcagt tcaacaataa    480
```

KITS FOR AND METHODS OF DIFFERENTIAL STAINING OF CERVICAL CANCER CELLS AND/OR TISSUES

REFERENCE TO CO-PENDING APPLICATIONS

Priority is claimed as a U.S. national entry under 35 U.S.C. 371 of PCT/IL2010/000399, filed on May 17, 2010; which claims priority to U.S. provisional patent application Ser. No. 61/213,228, filed on May 19, 2009.

FIELD AND BACKGROUND OF THE INVENTION

The present invention, in some embodiments thereof, relates to kits and methods of differential staining of cervical cancer cells and/or tissues.

Cervical cancer is the second most common cancer in women worldwide and is a leading cause of cancer-related death in women in underdeveloped countries. Worldwide, it is estimated that approximately 473,000 cases of cervical cancer are diagnosed each year, with about 253,500 deaths per year.

Routine cervical cancer screening of the population by cervical vaginal smears has significantly decreased the incidence of cervical cancer in Western countries. In the United States, in 1998, about 12,800 women were diagnosed with cervical cancer and about 4,800 died from the disease. The incidence (7 new cases per 100,000 women per year) and mortality in the US are about half those for the rest of the world.

Epidemiological research conducted in 2003 in the central and western regions of China showed that cervical cancer is becoming a major health hazard for women in the countryside, with nearly 100,000 cases of cervical cancer being diagnosed annually, with approximately 20,000 deaths in 2001.

Cervical cancer develops in the lining of the cervix by gradual abnormal changes of cervix cells. Changes include low, intermediate or high-grade cervical intraepithelial neoplasia (CIN), low or high-grade squamous intraepithelial lesion (SIL), a condition that precedes cervical cancer, carcinoma in situ or invasive carcinoma. Invasive cervical cancer includes about 80% of squamous cell carcinomas (SCC) and about 20% of adenocarcinomas.

Cervical vaginal smears are scrapings from the female reproductive tract aimed at enabling the diagnosis of numerous types of atypia, some of neoplastic nature, others of pre-malignant nature, or other pathological processes. All types of cellular samples must be transferred to a slide, processed and stained in order to enable visualization by means of light microscopy.

At present, diagnostic cytology is typically based on a rather narrow set of staining methods and compositions such as alcohol-fixed Papanicolaou stain and the air-dried May-Grunwald-Giemsa (a version of which is known as Romanowsky) stain, while staining with hematoxylin and eosin, Shorr's staining for endocrine cytology and the Pappenheim method are more rarely used.

The Papanicolaou staining method was initially developed for analysis of vaginal smears [Papanicolaou and Traut, Am. Y. Obst. Gynecol. (1941) 42:193-206; Papanicolaou "Atlas of Exfoliative Cytology" Cambridge, Mass.: Harvard University Press (1954)] and allows the differentiation of cell types of stratified and simple epithelia present in alcohol-fixed smears, with a detailed morphology of the nucleus and cytoplasm in normal and tumor cells. However, the Papanicolaou staining procedure, as well as all other cytological staining procedures, does not reveal any tinctorial selectivity for malignant cells, and the assessment of pathologically relevant traits is performed by means of interpretation of cellular morphology, which usually requires highly qualified and experienced cytopathologists.

The classical cytological techniques are in many cases supplemented by a group of technologies, which are based on compounds of high affinity and specificity, known as immunohistochemistry, immunocytochemistry or in situ hybridization. These technologies are used for detection of tumor markers of prognostic value (e.g., the p16INK4A and p14ARF markers, p16 protein), as well as the detection of other oncogenic expression features and nucleic acid sequences.

PCT Publication No. WO2007/102146 discloses a method of staining or pre-staining cells using an extract of a *Ficus elastica* plant, or active ingredients thereof, for the diagnosis of cancer or metabolic diseases.

SUMMARY OF THE INVENTION

According to an aspect of some embodiments of the present invention there is provided a method of staining a cervical cell sample, the method comprising: (i) contacting the cervical cell sample with a *Ficus elastics* plant extract, (ii) staining the cervical cell sample with New Fuchsin, and (iii) staining the cervical cell sample with Light Green or Fast green, thereby staining the cervical cell sample.

According to an aspect of some embodiments of the present invention there is provided a method diagnosing a pre-malignant or a malignant cervical tumor in a subject, comprising (a) staining a cervical cell sample of the subject according to the method of the invention, to thereby obtain a stained cervical cell sample, and (b) identifying at least one cervical cell of the cervical cell sample having a red cytoplasm above a pre-determined threshold, wherein presence of the at least one cervical cell having the red cytoplasm above the pre-determined threshold is indicative of a non- or less-differentiated cell as compared to a normal cervical cell, thereby diagnosing the pre-malignant or the malignant cervical tumor in the subject.

According to some embodiments of the invention, the method of the invention, further comprising: (c) analyzing a morphology of the at least one cervical cell having the red cytoplasm above the pre-determined threshold, wherein presence of an abnormal morphology in the same cell having the red cytoplasm above the pre-determined threshold as compared to a morphology of a normal cervical cell is indicative of the pre-malignant or malignant cervical tumor.

According to some embodiments of the invention, the method further comprising detecting an expression level of a cervical malignant marker or a cervical pre-malignant marker in at least one cervical cell of the cervical cell sample, wherein an expression level above a pre-determined threshold of the cervical malignant marker or of the cervical pre-malignant marker is indicative that the at least one cervical cell is a malignant or a pre-malignant cell, respectively, thereby identifying the cervical malignant or cervical pre-malignant cell.

According to some embodiments of the invention, the presence of at least one cervical cell which is identified as a non- or less-differentiated cell and presence of at least one cervical cell which exhibits the expression level above the pre-determined threshold of the cervical malignant or of the cervical pre-malignant marker in the same cervical cell sample indicates the positive diagnosis of the pre-malignant or the malignant cervical tumor in the subject.

According to some embodiments of the invention, the presence of at least one cervical cell having the abnormal morphology, presence of at least one cervical cell which is identified as a non- or less-differentiated cell and presence of at least one cervical cell which exhibits the expression level above the pre-determined threshold of the cervical malignant or of the cervical pre-malignant marker in the same cervical cell sample indicates the positive diagnosis of the pre-malignant or the malignant cervical tumor in the subject.

According to an aspect of some embodiments of the present invention there is provided a method of staining a cervical tissue section, the method comprising: (i) contacting the cervical tissue section with a *Ficus elastics* plant extract, (ii) staining the cervical tissue section with New Fuchsin, and (iii) staining the cervical tissue section with Light Green or Fast green, thereby staining the cervical tissue section.

According to an aspect of some embodiments of the present invention there is provided a method of staining a cervical smear, comprising: (i) contacting the cervical smear with a *Ficus elastics* plant extract, and (ii) staining the cervical smear with New Fuchsin, and (iii) staining the cervical smear with Light Green or Fast green, thereby staining the cervical smear.

According to an aspect of some embodiments of the present invention there is provided a method of staining a cervical cell monolayer, comprising: (i) contacting the cervical cell monolayer with a *Ficus elastics* plant extract, (ii) staining the cervical cell monolayer with New Fuchsin, and (iii) staining the cervical cell monolayer with Light Green or Fast green, thereby staining the cervical cell monolayer.

According to an aspect of some embodiments of the present invention there is provided a method of staining a cervical tissue sample, comprising: (a) deparaffinizing the cervical tissue sample in xylene, and subsequently (b) washing the cervical tissue sample in ethanol, and subsequently (c) washing the cervical tissue sample in water, and subsequently (d) staining the cervical tissue sample with Hematoxylin, and subsequently (e) washing the cervical tissue sample in water, and subsequently (f) contacting the cervical tissue sample with a *Ficus elastics* plant extract, and subsequently (g) washing the cervical tissue sample in water, and subsequently (h) staining the cervical tissue sample with New Fuchsin, and subsequently (i) washing the cervical tissue sample in water, and subsequently (j) incubating the cervical tissue sample in an ethanol solution, and subsequently (k) staining the cervical tissue sample with Light Green or Fast green, and subsequently (l) washing the cervical tissue sample with water, thereby staining the cervical tissue sample.

According to an aspect of some embodiments of the present invention there is provided a method of staining a cervical smear, comprising: (a) fixing the cervical smear in a solution of Trichloroacetic acid (TCA), and subsequently (b) washing the cervical smear in water, and subsequently (c) staining the cervical smear with Hematoxylin, and subsequently (d) washing the cervical smear in water, and subsequently (e) contacting the cervical smear with a *Ficus elastics* plant extract, and subsequently (f) washing the cervical smear in water, and subsequently (g) incubating the cervical smear with a New Fuchsin solution, and subsequently (h) washing the cervical smear in water, and subsequently (i) incubating the cervical smear in an ethanol solution, and subsequently (j) washing the cervical smear in water, and subsequently (k) staining the cervical smear with Light Green or Fast Green, and subsequently (l) washing the cervical smear with water, thereby staining the cervical smear.

According to an aspect of some embodiments of the present invention there is provided a method of staining a cervical cell monolayer, comprising: (a) fixing the cervical cell monolayer in a solution of Trichloroacetic acid (TCA), and subsequently (b) washing the cervical cell monolayer in water, and subsequently (c) staining the cervical cell monolayer with Hematoxylin, and subsequently (d) washing the cervical cell monolayer in water, and subsequently (e) contacting the cervical cell monolayer with a *Ficus elastics* plant extract, and subsequently (f) washing the cervical cell monolayer in water, and subsequently (g) staining the cervical cell monolayer with New Fuchsin, and subsequently (h) washing the cervical cell monolayer in water, and subsequently (i) incubating the cervical cell monolayer in an ethanol solution, and subsequently (j) washing the cervical cell monolayer in water, and subsequently (k) staining the cervical cell monolayer with Light Green or Fast Green, and subsequently (l) washing the cervical cell monolayer with water, and subsequently (m) washing the cervical cell monolayer in an ethanol solution, and subsequently (n) washing the cervical cell monolayer with water, thereby staining the cervical cell monolayer.

According to some embodiments of the invention, the method further comprising detecting an expression level of a cervical malignant marker or a cervical pre-malignant marker in at least one cervical cell of the cervical cell sample, the cervical smear, the cervical tissue section or the cervical cell monolayer, wherein an expression level above a pre-determined threshold of the cervical malignant marker or of the cervical pre-malignant marker is indicative that the at least one cervical cell is a malignant or a pre-malignant cell, respectively, thereby identifying the cervical malignant or cervical pre-malignant cell.

According to an aspect of some embodiments of the present invention there is provided a method of diagnosing a pre-malignant or a malignant cervical tumor in a subject, comprising (a) staining a cervical cell sample of the subject according to the method of the invention, to thereby obtain a stained cervical cell sample, (b) identifying at least one cervical cell of the cervical cell sample having a red cytoplasm above a pre-determined threshold, wherein presence of the at least one cervical cell having the red cytoplasm above the pre-determined threshold is indicative of a non- or less-differentiated cell as compared to a normal cervical cell, thereby diagnosing the pre-malignant or the malignant cervical tumor in the subject.

According to some embodiments of the invention, wherein presence of at least one cervical cell which is identified as a non- or less-differentiated cell according to the method of some embodiments of the invention and at least one cervical cell which exhibits the expression level above the pre-determined threshold of the cervical malignant or of the cervical pre-malignant marker according to the method of some embodiments of the invention in the same cervical cell sample indicates the positive diagnosis of the pre-malignant or the malignant cervical tumor in the subject.

According to some embodiments of the invention, wherein presence of at least one cervical cell having the abnormal morphology according to the method of some embodiments of the invention, at least one cervical cell which is identified as a non- or less-differentiated cell according to the method of some embodiments of the invention and at least one cervical cell which exhibits the expression level above the pre-determined threshold of the cervical malignant or of the cervical pre-malignant marker according to the method of some embodiments of the invention in the same cervical cell sample indicates the positive diagnosis of the pre-malignant or the malignant cervical tumor in the subject.

According to some embodiments of the invention, the method further comprising digesting mucin in the cervical cell sample, the cervical smear, the cervical cell monolayer or the cervical tissue section with an enzyme prior to the staining with the New Fuchsin.

According to some embodiments of the invention, the method further comprising staining the cervical cell sample, the cervical smear, the cervical cell monolayer or the cervical tissue section with an agent which differentially stains mucin in a color distinguishable from the color obtained by staining with New Fuchsin, light green and fast green.

According to some embodiments of the invention, the method further comprising mounting the stained cervical cell sample, cervical smear, cervical cell monolayer or cervical tissue section with a mounting medium which comprises an anti-oxidant.

According to an aspect of some embodiments of the present invention there is provided a kit for staining cervical cell sample and/or diagnosing a cervical pre-malignant or malignant tumor, comprising a packaging material packaging a *Ficus elastics* plant extract, New Fuchsin, and Light Green.

According to an aspect of some embodiments of the present invention there is provided a kit for staining cervical cell sample and/or diagnosing a cervical pre-malignant or malignant tumor, comprising a packaging material packaging a *Ficus elastics* plant extract, New Fuchsin, and Fast Green.

According to some embodiments of the invention, the method further comprising staining the cervical cell sample with Hematoxylin.

According to some embodiments of the invention, the method further comprising staining the cervical tissue section with Hematoxylin.

According to some embodiments of the invention, the method further comprising staining the cervical smear with Rematoxylin.

According to some embodiments of the invention, the method further comprising staining the cervical cell monolayer with Hematoxylin.

According to some embodiments of the invention, step (i) is effected prior to step (iii).

According to some embodiments of the invention, step (i) is effected prier to step (ii).

According to some embodiments of the invention, the contacting with the *Ficus elastics* plant extract is effected prior to staining the cervical cell sample with Light Green.

According to some embodiments of the invention, the contacting with the *Ficus elastics* plant extract is effected prior to staining the cervical cell sample with New Fuchsin.

According to some embodiments of the invention, the method further comprising: (c) analyzing a morphology of the at least one cervical cell having the red cytoplasm above the pre-determined threshold, wherein presence of an abnormal morphology in the cell having the red cytoplasm above the pre-determined threshold as compared to a morphology of a normal cervical cell is indicative of the pre-malignant or malignant cervical tumor.

According to some embodiments of the invention, the pre-malignant cervical tumor is selected from the group consisting of an intraepithelial neoplasia (CIN), a squamous intraepithelial lesion (SIL).

According to some embodiments of the invention, the malignant cervical tumor is selected from the group consisting of carcinoma in situ and invasive carcinoma.

According to some embodiments of the invention, the invasive carcinoma is selected from the group consisting of squamous cell carcinomas (SCC) and adenocarcinoma.

According to some embodiments of the invention, the cervical cell sample is selected from the group consisting of a cervical tissue-section, a cervical smear and a cervical cell monolayer.

According to some embodiments of the invention, the staining with the Hematoxylin is effected prior to the contacting with the *Ficus elastics* plant extract.

According to some embodiments of the invention, the method further comprising fixing the cervical sample, cervical smear or cervical cell monolayer prior to the contacting with the *Ficus elastics* plant extract.

According to some embodiments of the invention, the fixing is effected using a fixative selected from the group consisting of Trichloroacetic acid (TCA), ethanol and methanol.

According to some embodiments of the invention, the cervical malignant or cervical pre-malignant marker is selected from the group consisting of ki67 antigen (antigen identified by monoclonal antibody Ki-67), Hypoxia-inducible factor 1-alpha (HIF-1alpha), Id-1 (Inhibitor of differentiation/DNA binding-1), p16$^{INK4a}$ (Cyclin-dependent kinase inhibitor 2A), p21WAF1/CIP1, Tn antigen (Tn-Ag), P53 and proliferating cell nuclear antigen (PCNA).

According to some embodiments of the invention, the cervical monolayer is devoid of blood cells.

According to some embodiments of the invention, the cervical monolayer is a ThinPrep™ sample.

According to some embodiments of the invention, the cervical monolayer is a liquid based cytology sample.

According to some embodiments of the invention, the *Ficus elastics* plant extract is selected from the group consisting of a crude *Ficus elastics* plant extract, $C_{23}H_{44}O_4$ and proanthocyanidins.

According to some embodiments of the invention, the kit further comprising instructions for use in staining cervical cell sample and/or diagnosing a cervical pre-malignant or malignant tumor in a subject.

According to some embodiments of the invention, detecting the expression level of the cervical malignant or the cervical pre-malignant marker is performed using a high affinity agent.

According to some embodiments of the invention, the high affinity agent is an antibody which specifically binds to the cervical malignant or cervical pre-malignant marker.

According to some embodiments of the invention, the high affinity agent is a polynucleotide selected from the group consisting of a polynucleotide which specifically hybridizes to an RNA encoding the cervical malignant or cervical pre-malignant marker and a polynucleotide which specifically amplifies the cervical malignant or cervical pre-malignant marker.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 1A-B are images of normal cervical biopsy histological sections depicting epithelia cells stained by the staining method according to some embodiments of the invention as described in Example 1 (FIG. 1A) or by H&E staining (FIG. 1B). Note the blue/green cytoplasm in FIG. 1A, which is the diagnostic cellular compartment of the staining method of the invention.

FIGS. 2A-B are images of cervical biopsy histological sections depicting cervical intra-epithelial neoplasia (CIN2) stained by the staining method of the invention as described in Example 1 (FIG. 2A) or H&E staining (FIG. 2B).

FIGS. 3A-B are images of cervical biopsy histological sections depicting squamous cell carcinoma of the cervix stained by the staining method of the invention as described in Example 1 (FIG. 3A) or by H&E staining (FIG. 3B).

Figure 4B:
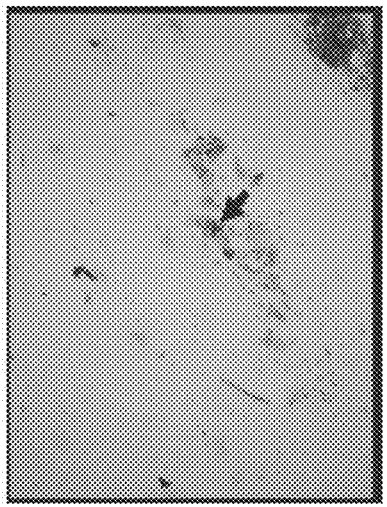
Figure 4D:
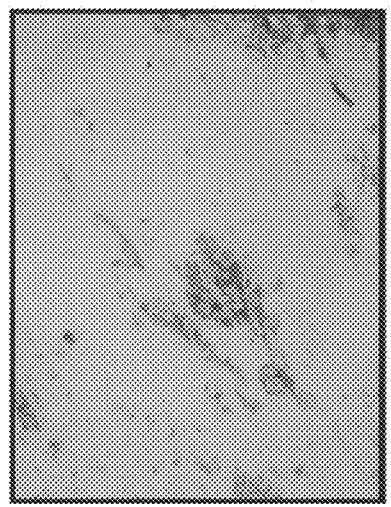
Figure 4A:
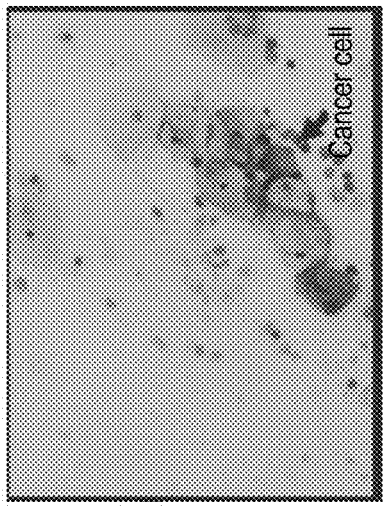
Figure 4C:
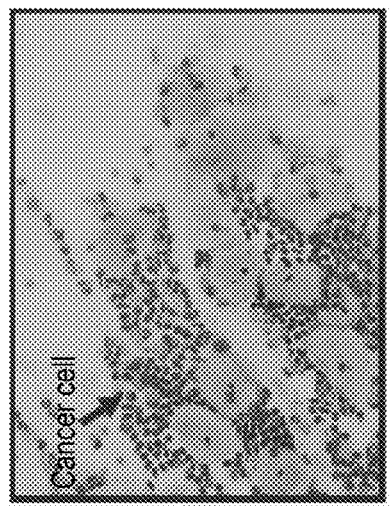

FIGS. 4A-D are images of cervical smears obtained from a patient with cervical cancer and stained by the staining method of the invention as described in Example 2 (FIGS. 4A-B) or by Pap staining (FIGS. 4C-D). FIGS. 4A and C—Objective magnification ×20. FIGS. 4B and D—Objective magnification ×4. It should be noted that in all microscopical images presented herein the ocular magnification was ×10. FIGS. 4A-B, the arrow in each panel points at the squamous cell carcinoma cell (same cell in two different magnifications).

FIGS. 5A-D are images of cervical ThinPrep™ samples obtained from a patient with cervical cancer and stained by the staining method of the invention as described in Example 3 (FIGS. 5A and C) or by Pap staining (FIGS. 5B and D). The cervical cell monolayer preparations contain cells with high-grade squamous intraepithelial lesions (FIGS. 5A, B, see arrows pointing at high-grade SIL (HSIL") as well as low-grade squamous intraepithelial lesions (FIGS. 5C, D, see arrows pointing at low-grade SIL (LSIL). Color of cytoplasm in cells in Pap preparation is variable and does not correlate with cytomorphology. In samples stained by the method of the invention the cytoplasm of normal cells stains green, whereas atypical cells have reddish cytoplasm.

Figure 6A:
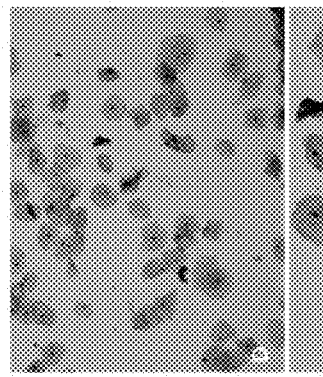
Figure 6B:
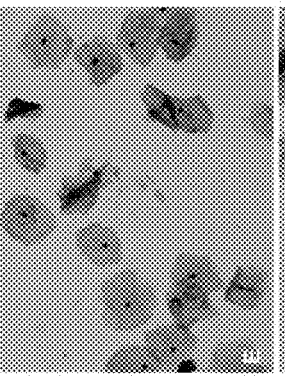
Figure 6C:
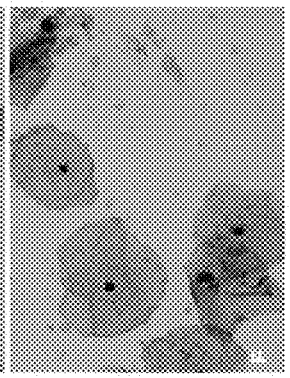
Figure 6D:
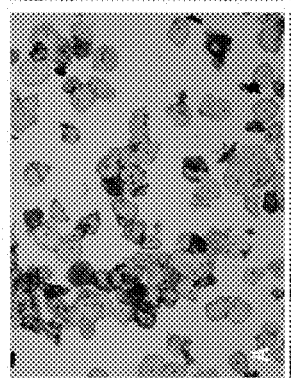
Figure 6E:
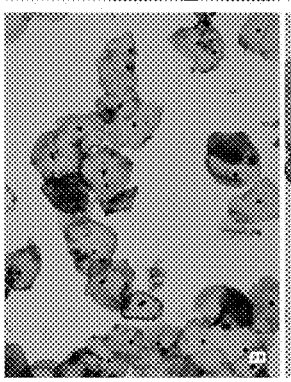
Figure 6F:
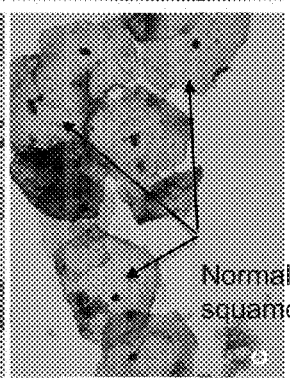

FIGS. 6A-F are images of cervical ThinPrep™ samples obtained from a healthy (normal control) subject and stained by the staining method of the invention as described in Example 3 (FIGS. 6A, B, C) or by Pap staining (FIGS. 6D, E, F). FIGS. 6A and D—Objective magnification ×4; FIGS. 6B and E—Objective magnification ×20; FIGS. 6C and F—Objective magnification ×40. The cervical cell monolayer preparation contains only normal cells. Color of cytoplasm in Pap preparation is variable as seen in the various magnifications. In the samples stained according to the staining method of the invention the cytoplasm of normal cells stains green, with a uniform pattern as seen in the different magnifications. Arrows in FIG. 6C point at normal superficial squamous cells.

FIGS. 7A-F are images of cervical ThinPrep™ samples depicting low grade squamous intraepithelial lesions stained by the staining method of some embodiments of the invention as described in Example 3 (FIGS. 7A, B, C; Arrows in FIGS. 7B and 7C point low grade squamous intraepithelial lesions cells) or by Pap staining (FIGS. 7D, E, F; Arrows in FIGS. 7E and 7F point low grade squamous intraepithelial lesions cells). FIGS. 7A and D—Objective magnification ×4; FIGS. 7B and E—Objective magnification ×20; FIGS. 7C and F—Objective magnification ×40. Color of cytoplasm in cells stained by Pap staining is variable and does not correlate with cytomorphology. Identification of atypical cells in the Pap stained slide is possible only at high (×20) Objective magnification. In samples stained according to the staining method of the invention the cytoplasm of normal cells stains green, whereas atypical cells have reddish cytoplasm. Moreover, as normal cells stain typically green, identification of suspected red stained cells is available even at low (×4) Objective magnification, and is confirmed by morphological analysis at a higher magnification. Note how easily the low grade squamous intraepithelial lesions cells are visible and detected in a cervical cell monolayer stained according to the staining method of some embodiments of the invention.

FIGS. 8A-D are images of normal cervical biopsy histological sections stained according to the staining method of some embodiments of the invention as described in Example 1 (FIGS. 8A and B) or by H&E staining (FIGS. 8C and D). Slides stained according to the staining method of some embodiments of the invention exhibit homogeneous green staining of normal cervical epithelia as seen at low Objective magnification (×10; FIG. 8A) and high Objective magnification (×40; FIG. 8B). High magnification shows clear morphological features, comparable to H&E staining (FIG. 8C, ×10 Objective magnification; FIG. 8D, ×40 Objective magnification).

FIGS. 9A-D are images of cervical biopsy histological sections depicting SCC stained by the staining method of the invention as described in Example 1 (FIGS. 9A and B; note squamous cell carcinoma cells marked by black arrows in FIG. 9B) or by H&E staining (FIGS. 9C and D). Note that in slides stained according to the staining method of the invention the entire invading epithelium containing red stained cells is seen at low Objective magnification (×4, FIG. 9A) with clear morphological features at high Objective magnification (×40, FIG. 9B). The parallel H&E stained slide (FIG. 9C, ×4 Objective magnification; and FIG. 9D, ×40 Objective magnification) confirms correct diagnosis.

FIGS. 10A-D are images of cervical biopsy histological sections depicting high-grade CIN3 dysplasia stained by the staining method of the invention as described in Example 1 (FIGS. 10A and B) or by H&E staining (FIGS. 10C and D). Slides stained according to the method of the invention show entire epithelium containing red stained cells at low Objective magnification (×10 Objective magnification, FIG. 10A) with clear morphological features at high Objective magnification (×40 Objective magnification, FIG. 10B; note dysplastic cells of CIN3 shown by black arrows in FIG. 10b). The parallel H&E stained slide (FIG. 10C, ×10 Objective magnification; FIG. 10D, ×40 Objective magnification) confirms correct diagnosis.

Figure 11C:
Figure 11D:
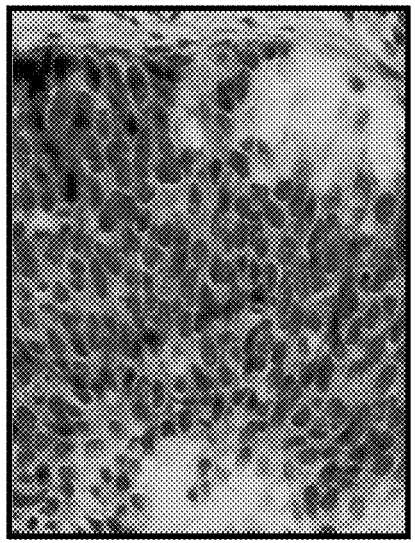
Figure 11A:
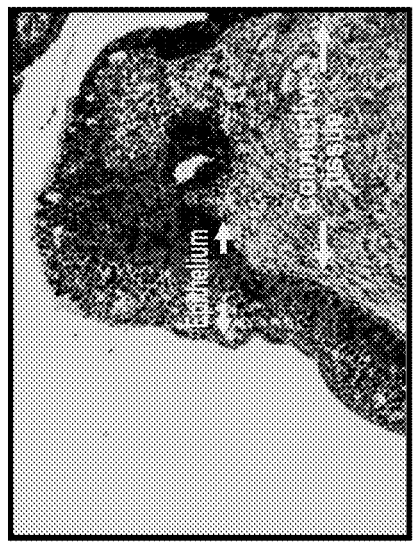
Figure 11B:
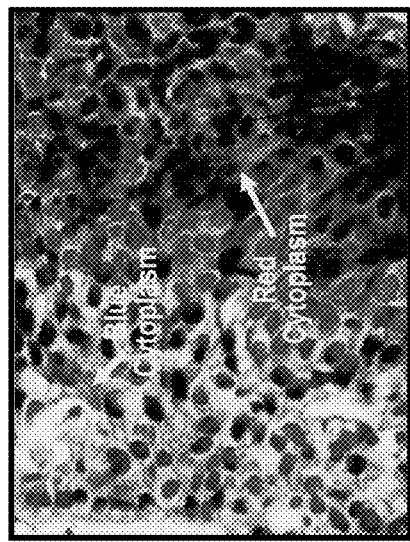

FIGS. 11A-D are images of cervical biopsy histological sections depicting middle-grade CIN2 dysplasia region stained according to the staining method of the invention as described in Example 1 (FIGS. 11A and B) or by H&E staining (FIGS. 11C and D). Slides stained according to the staining method of the invention show red cells predominating the epithelial region at low magnification (×10 Objective magnification, FIG. 11A). A clear transition from red (abnormal) to blue (normal) cytoplasmic cell staining is seen at the outer layer of the epithelium using high magnification (×40 Objective magnification, FIG. 11B; note dysplastic cells of CIN2 shown by a black arrow), enabling correct grading.

Parallel H&E stained slide (FIG. 11C, ×10 Objective magnification; and FIG. 11D, ×40 Objective magnification) confirms correct diagnosis.

Figure 12C:
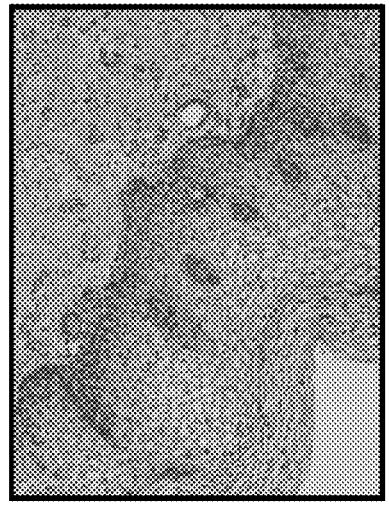
Figure 12D:
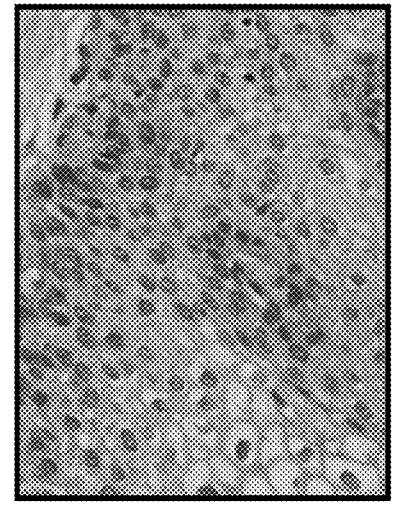

FIGS. 12A-D are images of cervical biopsy histological sections depicting low-grade CIN1 dysplasia stained according to the staining method of some embodiments of the invention as described in Example 1 (FIGS. 12A and B) or by H&E staining (FIGS. 12C and D). Slides stained according to the staining method of the invention show red staining of cells extending the basal region, evident at low Objective magnification (×10, FIG. 12A) and high Objective magnification (×40, FIG. 12B; note dysplastic cells as opposed to normal squamous cells in FIG. 12B). Transition from Red (abnormal) to blue (normal) cells enables correct grading. Parallel H&E stained slide (FIG. 12C, ×10 Objective magnification; and FIG. 12D, ×40 Objective magnification) confirms correct diagnosis.

Figure 13C:
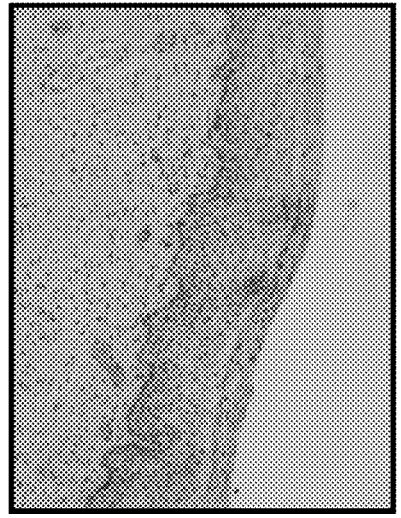
Figure 13D:
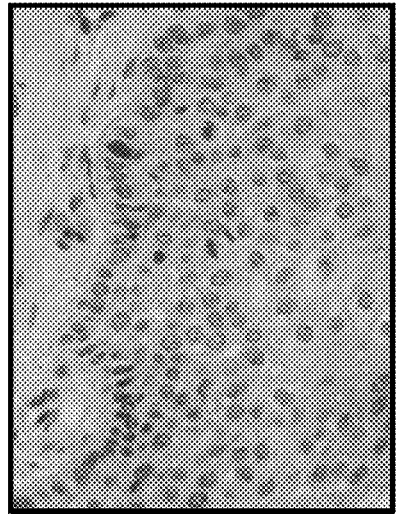

FIGS. 13A-D are images of cervical biopsy histological sections depicting low-grade CIN1 dysplasia stained according to the staining method of the invention as described in Example 1 (FIGS. 13A and B) or by H&E staining (FIGS. 13C and D). Slides stained according to the staining method of the invention show red staining of cells extending the basal region, evident at low Objective magnification (×10, FIG. 13A) and high Objective magnification (×40, FIG. 13B; note dysplastic cells as opposed to normal squamous cells in FIG. 13B). Transition from Red (abnormal) to blue (normal) cells enables correct grading. In the parallel H&E stained region (FIG. 13C, ×10 Objective magnification; and FIG. 13D, ×40 Objective magnification), these subtle changes are not easily detected and can be frequently misdiagnosed.

Figure 14:
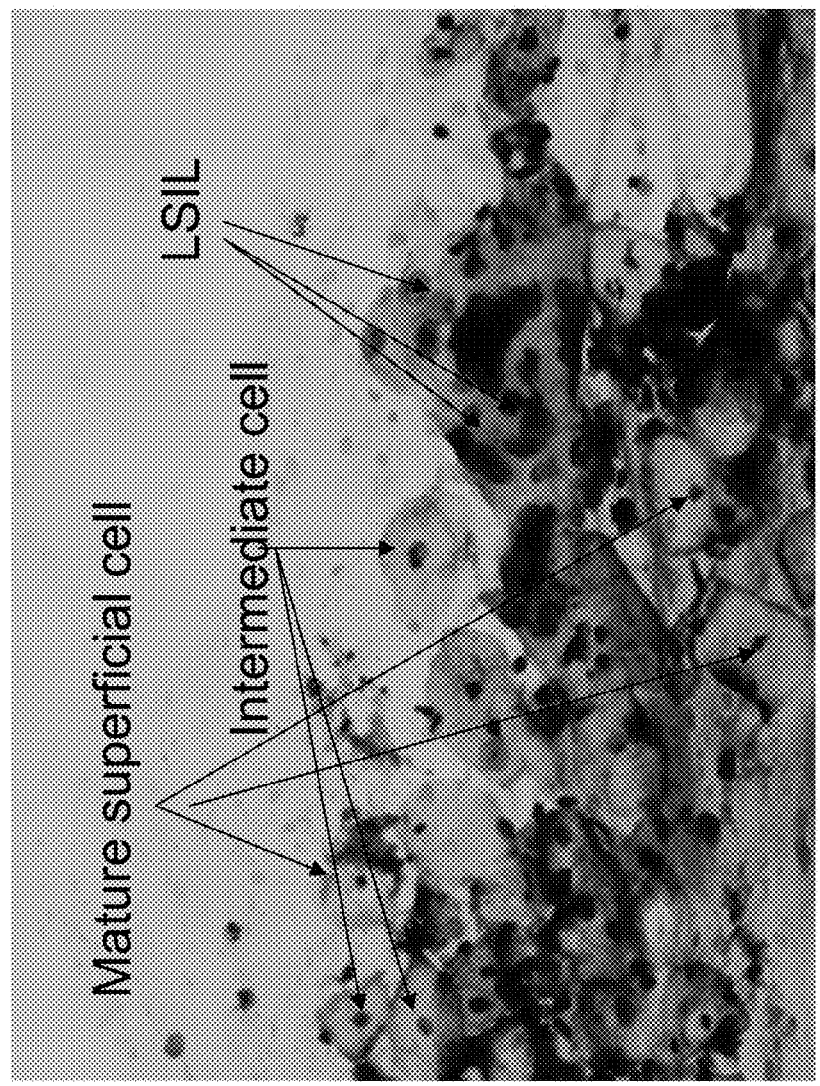

FIG. 14 is an image of a conventional cervical smear stained according to the method described in Example 4 of the Examples section which follows. Note that normal superficial cervical cells are stained in green color. Cluster of low grade dysplasia cells (LSIL) also present. LSIL cells have red nuclear color, and pink cytoplasm. Objective magnification ×20.

Figure 15:
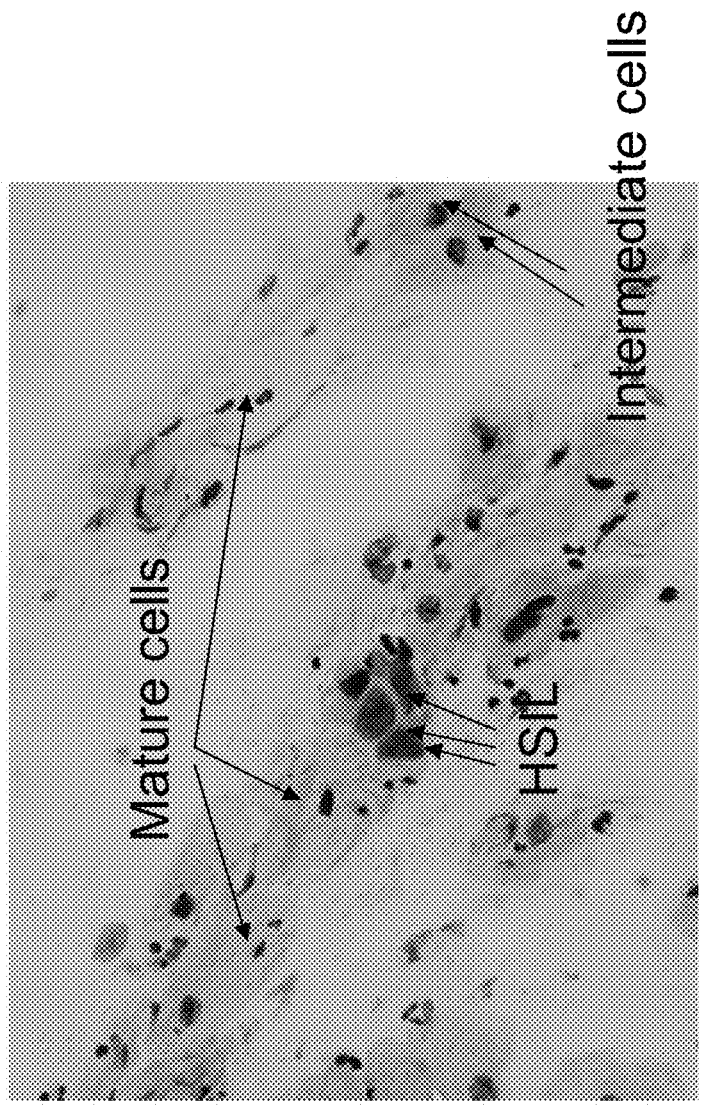

FIG. 15 is an image of a conventional cervical smear stained according to the method described in Example 4 of the Examples section which follows. Note that normal superficial cervical cells are stained in green color. Cluster of high grade dysplasia cells (HSIL) also present. HSIL cells have red nuclear color, and pink cytoplasm. Objective magnification ×20.

Figure 16:
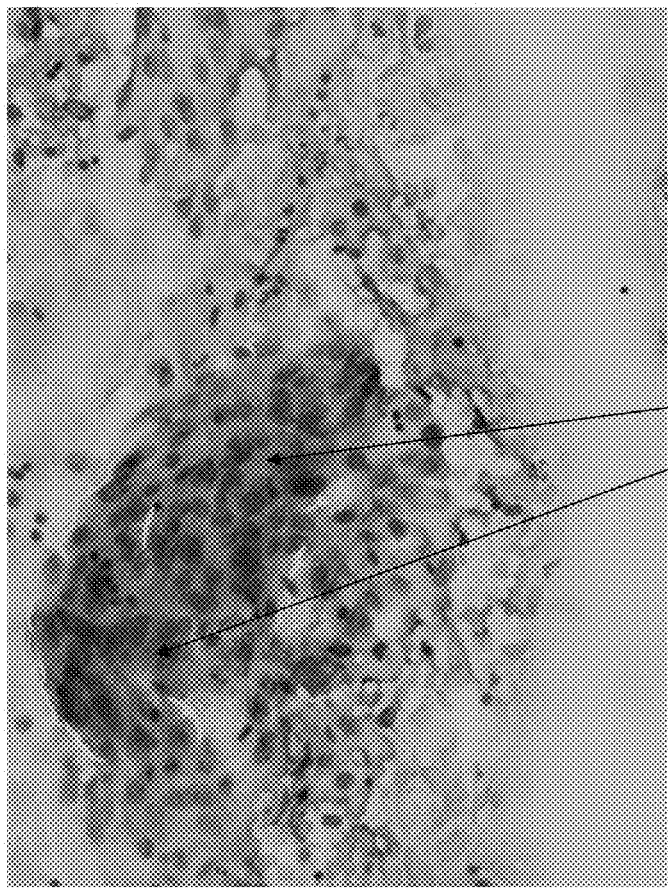

FIG. 16 is an image of a conventional cervical smear stained according to the method described in Example 4 of the Examples section which follows. Note the cluster of squamous cell carcinoma (SCC) cells present in the smear. Cells of SCC have red nuclear color, and pink cytoplasm. Objective magnification ×20.

Figure 17:
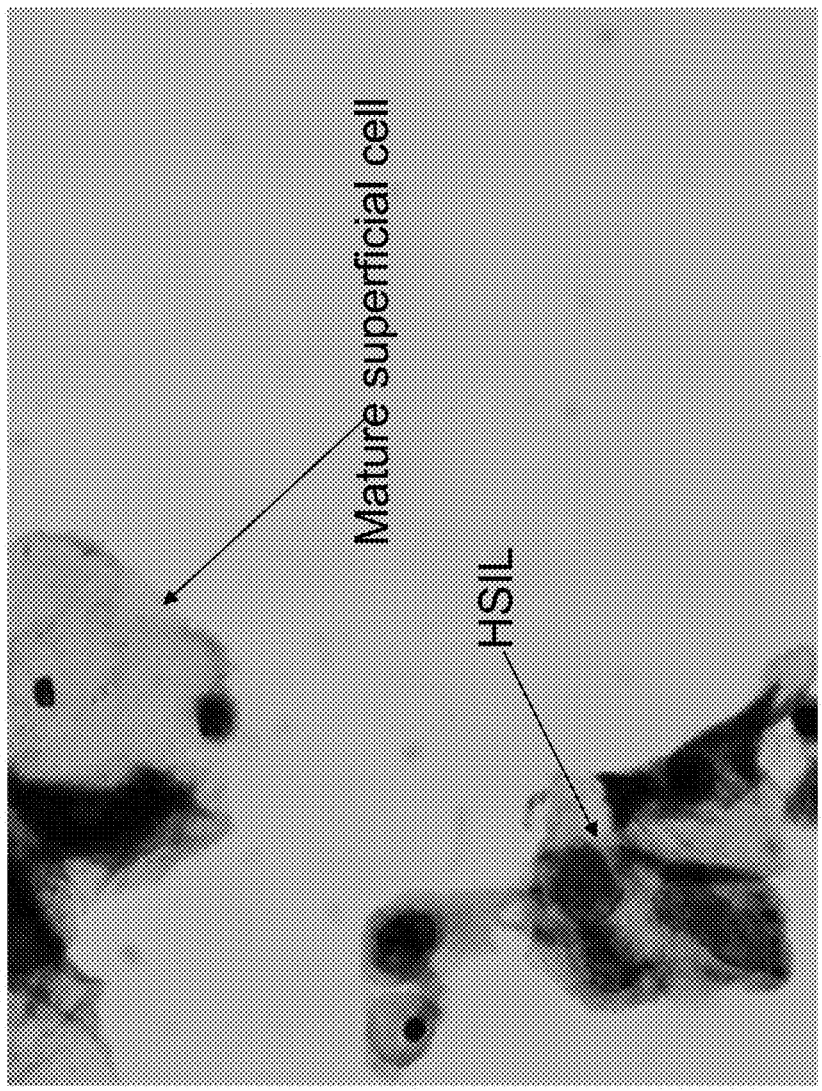

FIG. 17 is an image of a liquid-base cervical monolayer cell sample (ThinPrep™) stained according to the method described in Example 5 of the Examples section which follows in which Fast green is used instead of light green. Note the cluster of high grade dysplasia cells (HSIL) present in the sample. The HSIL cells have red nuclear color, and pink cytoplasm. Objective magnification ×40.

Figure 18:
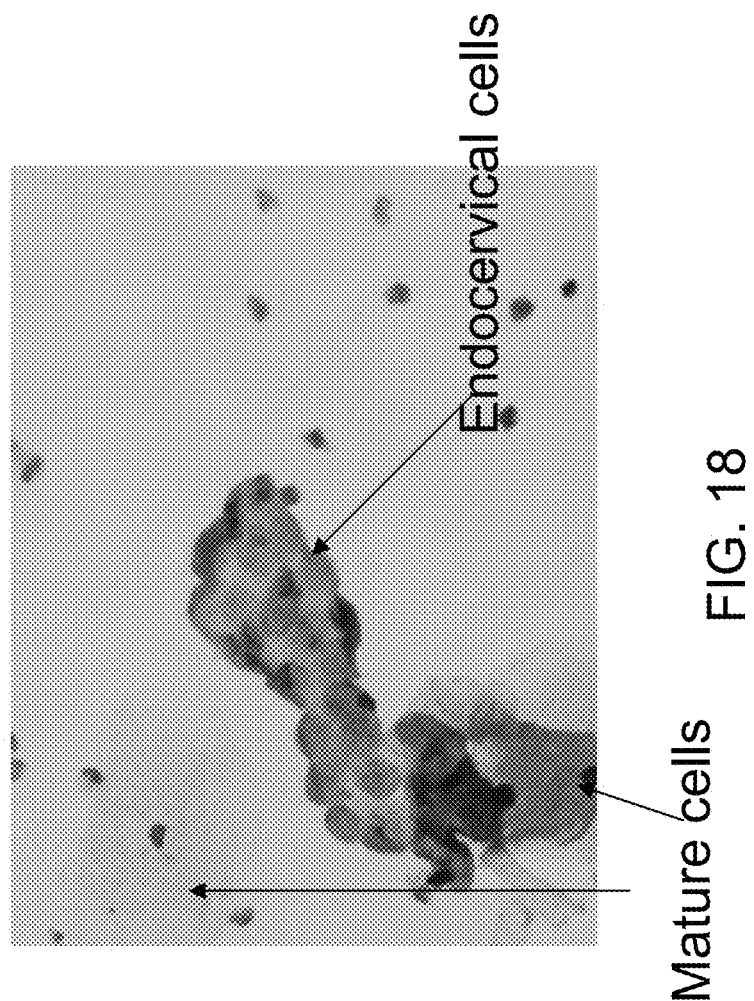

FIG. 18 is an image of endocervical cells obtained from a ThinPrep™ slide and stained according to the method of some embodiments of the invention. Note the typical morphological characteristics of endocervical cells. Objective magnification ×40.

Figure 19:
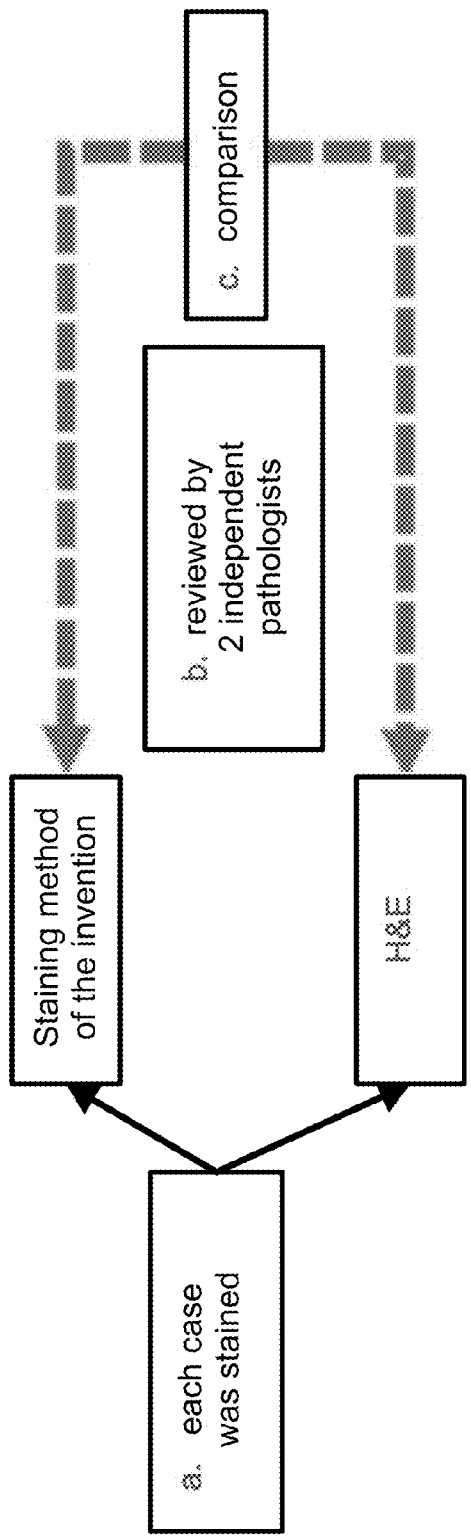

FIG. 19 is a diagram schematically illustrating the study described in Example 1 of the Examples section which follows. Cervical tissue section samples were subject to histological evaluation using the H&E staining and the staining method according to some embodiments of the invention. Each stained slide was reviewed by two independent expert pathologists and then the diagnosis by both methods was compared.

Figure 20:
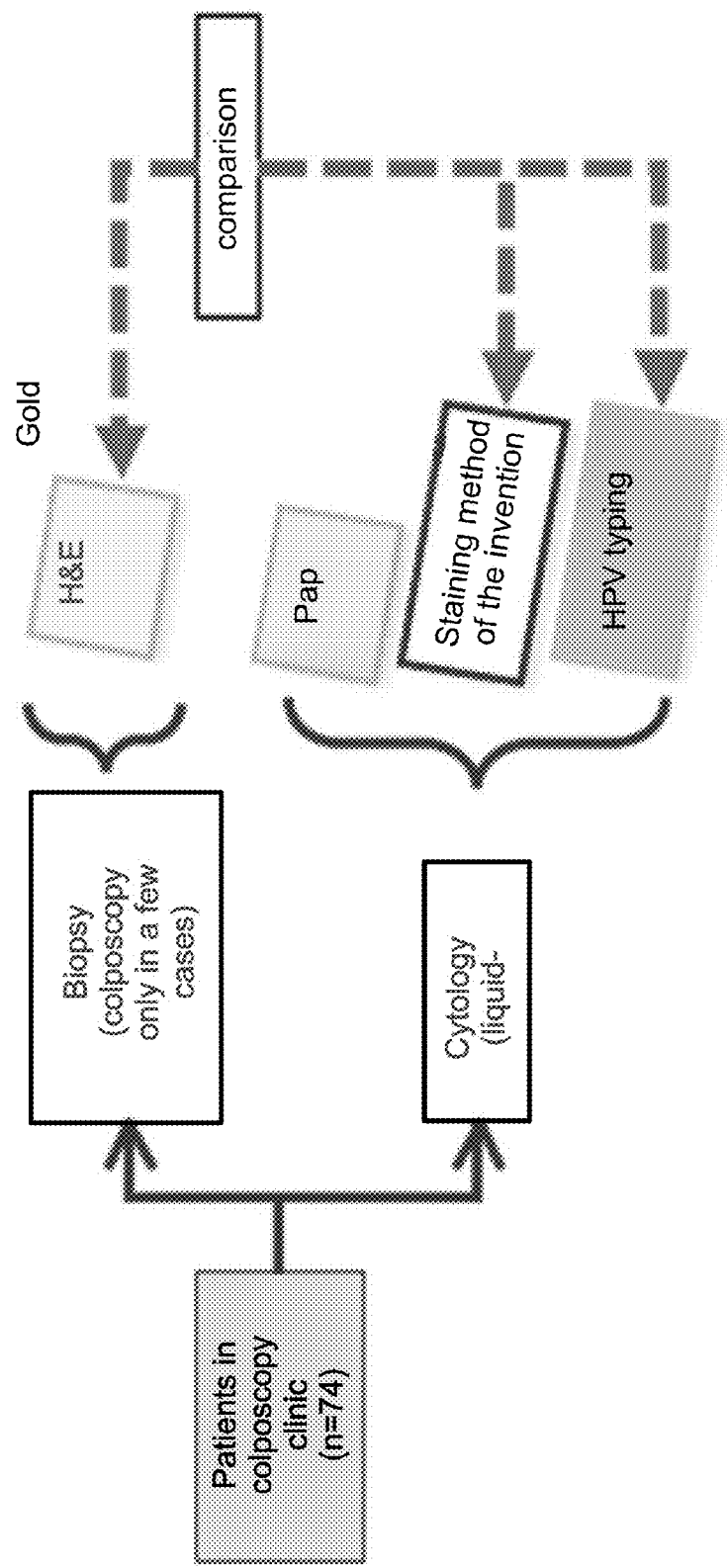

FIG. 20 is a diagram schematically depicting the study described in Example 3 of the Examples section which follows. Patients were invited to the colposcopy clinic to follow up on a suspicious Pap test. From each patient a tissue biopsy was retrieved for the preparation of a histological slide (stained with H&E) and a liquid base cervical sample was retrieved for the preparation of ThinPrep™ slides and for HPV test (in liquid). The ThinPrep™ slides were subject to staining according to the staining method of some embodiments of the invention and to staining according to Papanicolaou stain. The results of all tests was then compared.

Figure 21:

FIG. 21 is a prior art photograph showing endocervical cells stained with Papanicolaou stain (Diane Solomon, Ritu Nayar, Eds: The Bethesda System for Reporting Cervical Cytology. Definitions, criteria and explanatory notes; Second Edition. 2004, Page 12).

Figure 22:

FIG. 22 is a prior art photograph showing ASC-US cells [conventional smear preparation (CP)] stained with Papanicolaou stain (Diane Solomon, Ritu Nayar, Eds: The Bethesda System for Reporting Cervical Cytology. Definitions, criteria and explanatory notes; Second Edition. 2004, Page 70).

Figure 23:
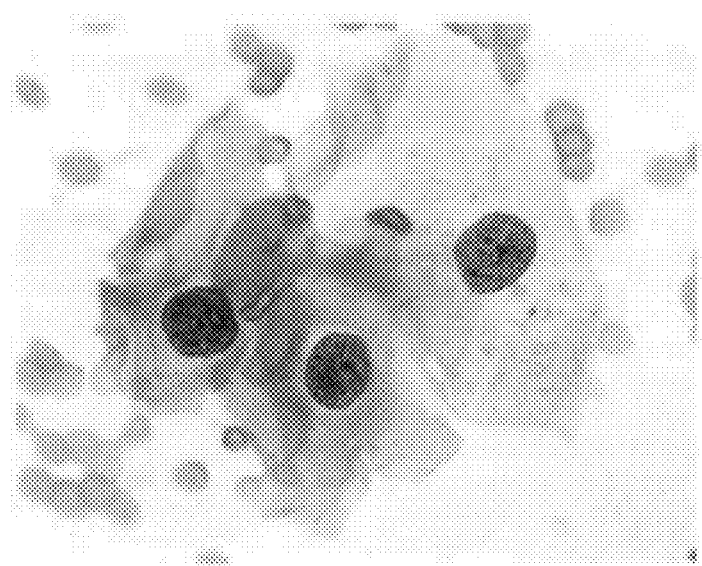

FIG. 23 is a prior art photograph showing low-grade squamous intraepithelial lesion [LSIL, conventional preparation (CP)] stained with Papanicolaou stain (Diane Solomon, Ritu Nayar, Eds: The Bethesda System for Reporting Cervical Cytology. Definitions, criteria and explanatory notes; Second Edition. 2004, Page 92).

Figure 24:
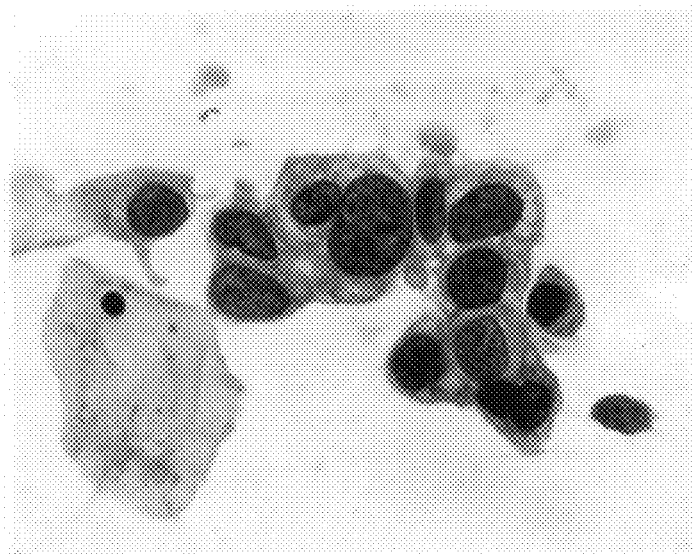

FIG. 24 is a prior art photograph showing high-grade squamous intraepithelial lesion (LSIL, CP, conventional preparation) stained with Papanicolaou stain (Diane Solomon, Ritu Nayar, Eds: The Bethesda System for Reporting Cervical Cytology. Definitions, criteria and explanatory notes; Second Edition. 2004, Page 101).

Figure 25:
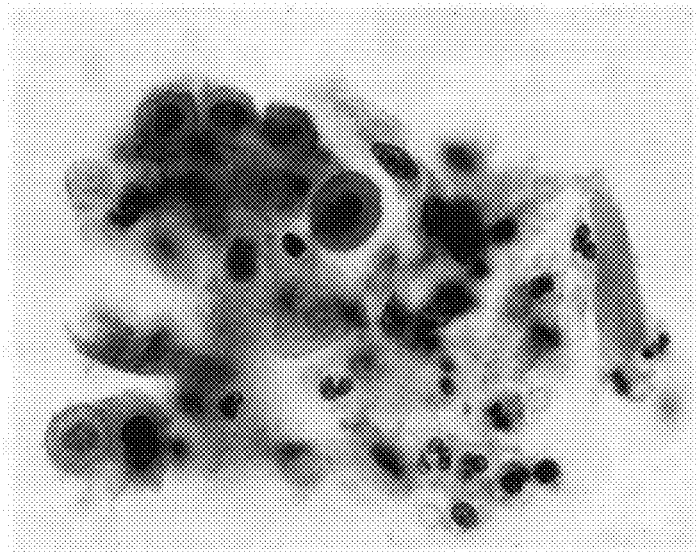

FIG. 25 is a prior art photograph showing squamous cell carcinoma keratinizing cells [Liquid-base preparation (LBP)] stained with Papanicolaou stain (Diane Solomon, Ritu Nayar, Eds: The Bethesda System for Reporting Cervical Cytology. Definitions, criteria and explanatory notes; Second Edition. 2004, Page 117).

Figure 26:
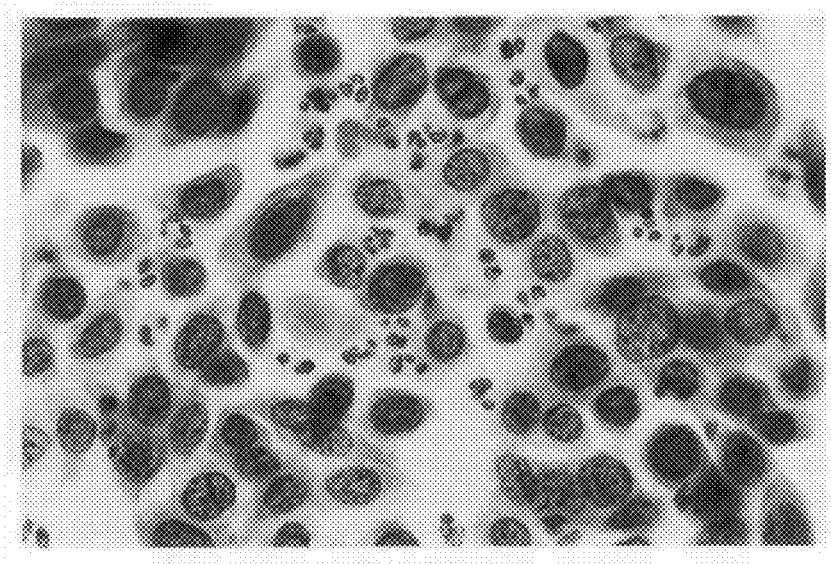

FIG. 26 is a prior art photograph showing squamous cell carcinoma non-keratinizing cells [conventional smear preparation (CP)] stained with Papanicolaou stain (Diane Solomon, Ritu Nayar, Eds: The Bethesda System for Reporting Cervical Cytology. Definitions, criteria and explanatory notes; Second Edition. 2004, Page 117).

Figure 27:
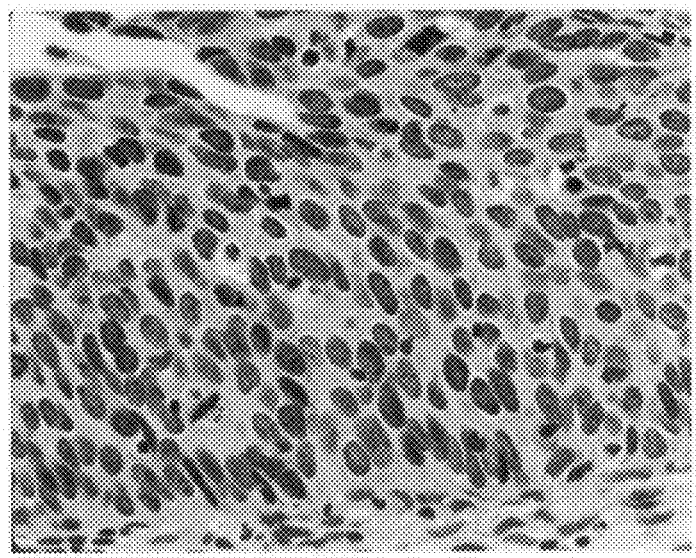

FIG. 27 is a prior art photograph showing CIN3 cells stained with Hematoxylin-Eosine (H&E) stain (histology, tissue section) (Diane Solomon, Ritu Nayar, Eds: The Bethesda System for Reporting Cervical Cytology. Definitions, criteria and explanatory notes; Second Edition. 2004, Page 101).

Figure 28:
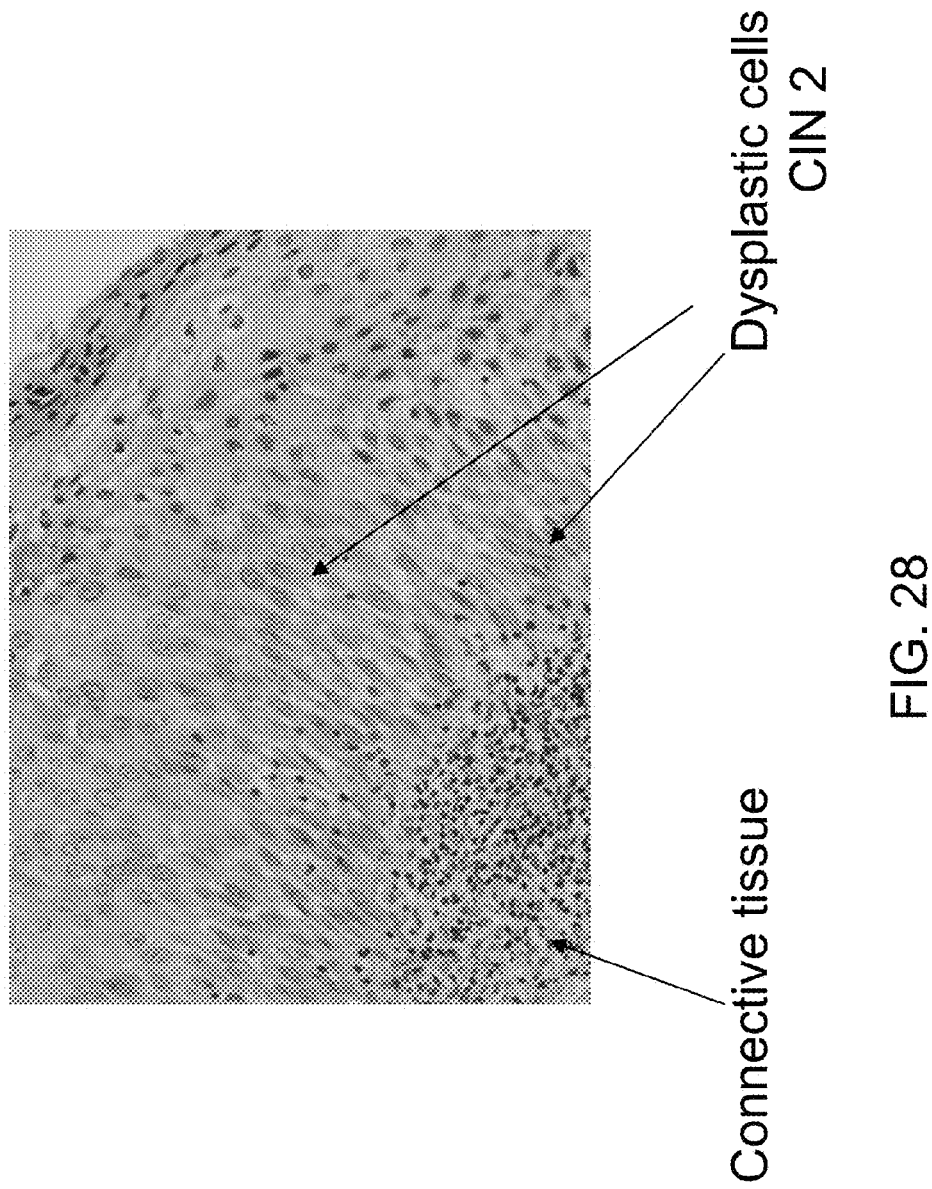

FIG. 28 is a photograph of a histological tissue section stained by H&E and demonstrating presence of CIN2 dysplastic cells.

FIG. 29 is a photograph of a histological tissue section stained by H&E and demonstrating presence of non-keratinizing SCC (squamous cell carcinoma) cells.

DESCRIPTION OF SPECIFIC EMBODIMENTS OF THE INVENTION

The present invention, in some embodiments thereof, relates to methods and kits for differential staining of cervical cancer cells and use thereof in diagnosing cervical cancer.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

The present inventors have uncovered a novel method of differentially staining cervical cancerous or pre-cancerous cells.

Figure 12A:
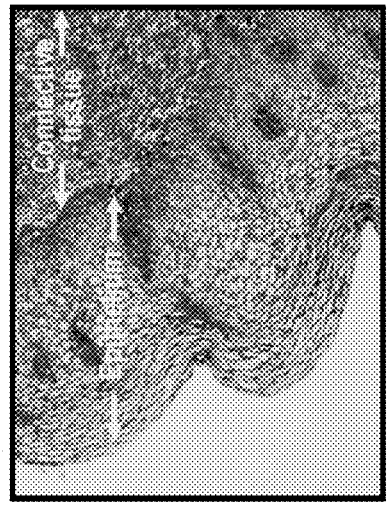
Figure 12B:
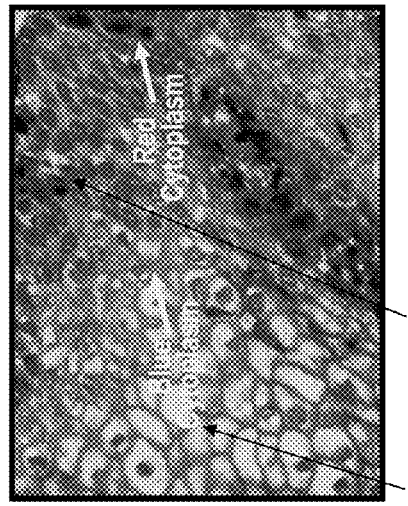

As shown in the Examples section which follows, using the novel method of the invention cancerous or pre-cancerous cells are differentially stained in cervical biological samples such as cervical tissue sections (Example 1, FIGS. 1A-B, 2A-B, 3A-B, 8A-D, 9A-D, 10A-D, 11A-D, 12A-D, 13A-D and 19, and Tables 3, 4, 5 and 6), conventional cervical smears (Example 2, FIGS. 4A-D and Tables 7 and 8) or liquid-based, cell monolayer cervical samples (e.g., ThinPrep™ slides; FIGS. 20, 5A-D, 6A-F, 7A-F and Tables 9 and 10). For example, while the cytoplasm of pre-malignant cervical intra-epithelial neoplasia at grade 1 (CIN1; FIGS. 12A-B), 2 (CIN2l FIGS. 11A-B) or 3 (CIN3; FIGS. 10A-B), or of SCC (FIGS. 9A-B) are stained in red, the cytoplasm of normal cervical cells are stained in green (FIGS. 1A-B). Moreover, since the novel staining method of some embodiments of the invention preserves the characteristics morphology of the cells in the sample, it enables correct grading of the cancerous or pre-cancerous cells (FIGS. 11A-D). In addition, the method of the invention was found to be superior over the conventional Pap staining in screening of cervical smears since it enables detection of cancerous cells even at low magnification (e.g., using an Objective magnification of ×4), which does not allow any distinction between cancerous cells in conventional Pap stained cervical smears (Example 2, FIGS. 4A-D) and it exhibits an increased sensitivity as compared to Papanicolaou staining and an increased specificity as compared to HPV testing (Table 10; Example 3). Furthermore, as is shown in Example 3 of the Examples section which follows, using the novel method of some embodiments of the invention, the present inventors have correctly diagnosed low-grade (FIGS. 7A-F) or high-grade (FIGS. 5A-B) squamous intraepithelial lesions in liquid-based ThinPrep™ samples, demonstrating the robust screening power of the method of the invention in diagnosing and staging cervical cancer using non-invasive methods. In addition, as described in Example 4 and shown in FIGS. 14-16, the present inventors were capable of identifying low grade dysplasia cells (LSIL), high grade dysplasia cells (HSIL) and squamous cell carcinoma (SCC) using conventional cervical smears stained according to the novel staining method of some embodiments of the invention. Moreover, as shown in FIG. 17 and described in Example 5, using the novel combination of staining with *Ficus* extract, New Fuchsin and Fast Green the present inventors were capable of identifying high grade dysplasia cells (HSIL) in a liquid-based cervical monolayer sample.

Thus, according to an aspect of some embodiments of the invention, there is provided a method of staining a cervical cell sample. The method is effected by (i) contacting the cervical cell sample with a *Ficus elastics* plant extract, (ii) staining the cervical cell sample with New Fuchsin, and (iii) staining the cervical cell sample with Light Green or Fast green, thereby staining the cervical cell sample.

As used herein the phrase "cervical cell" refers to a single cell or a plurality of cells isolated from the cervix. Single cells or aggregates can be used.

The cervical cell sample can be any biological sample which comprises cervical cells, cervical cell-lines, primary cultures of cervical cells or uncultured cellular samples which are obtained from a tissue biopsy (an incisional biopsy, an excisional biopsy or a complete resection), or using semi- or non-invasive sampling methods such as retrieving cells from the cervix, external part of the cervix and/or from endocervical canal using a collection device such as a brush, a cervical wash or lavage.

According to some embodiments of the invention the cervical cell sample comprises a cervical epithelial cell.

Non-limiting examples of cervical epithelial cells include squamous, glandular, and metaplastic epithelial cells. The squamous cells are derived from ectocervix and the vagina; the glandular cells are derived from the endocervix; metaplastic cells are derived from the transformation zone of the cervix.

It should be noted that the cervical cell sample may also comprise endocervical cells.

According to some embodiments of the invention identification and/or classification of the cells (to the different cell types) present in the cervical cell sample is performed by morphological evaluation of the cells based on known morphological characteristics, which are further described hereinbelow.

According to some embodiments of the invention, the cervical cell sample is a cervical tissue section (e.g., a paraffin tissue section, a frozen tissue, a cryosection obtained from a cervical tissue biopsy), a cervical smear or a cervical cell monolayer (e.g., liquid-based sample such as the ThinPrep™ sample).

As used herein the phrase "cervical tissue section" refers to a section of a cervical tissue having a thickness of about 1-200 microns.

According to some embodiments of the invention, the tissue section has a thickness of about 2 microns to about 50 microns, e.g., from about 2 microns to about 20 microns, e.g., about 2 microns to about 10 microns, e.g., about 4-5 microns, e.g., 4 microns.

As used herein the phrase "cervical smear" refers to a crude cell sample of the cervix which is pasted on a microscopic slide without any purification.

As used herein the phrase "cervical cell monolayer" refers to a cell sample of the cervix which forms a single layer of cervical cells on a microscopic-slide.

According to specific embodiments of the invention, the cervical cell monolayer does not comprise immune cells.

According to some embodiments of the invention, the cervical monolayer is devoid of red blood cells.

According to some embodiments of the invention, the cervical monolayer is devoid of any blood cell.

According to some embodiments of the invention, the cervical monolayer comprises cervical cells which do not overlap on each other when placed on a slide, thus each cell has clear cell boundaries and a clear microscopic view of each cell is obtained.

The cervical cell sample can include homogeneous or heterogeneous populations of cells (e.g., cells of different differentiation states). Typically, the cervical cell sample comprises heterogeneous populations of cells.

For example, cervical cell sample may comprise malignant or pre-malignant cells as well as normal healthy cells. Alternatively, cervical cell sample may comprise metabolically normal and metabolically impaired cells. Additionally or alternatively, cervical cell sample may comprise inflammatory cells, pre-malignant, malignant and/or normal, healthy cells.

According to presently preferred configurations, the cervical cell sample is placed on a microscopic slide. Methods of attaching cells to microscopic slides are well known in the art, and include, for example, layering cells of the microscopic slides, centrifuging the cells on the slide (e.g., using a cytospin), mounting tissue sections on the slides (e.g., using paraffin-embedded sections), or smearing cells over a microscopic slide. The microscopic slides which include the cervical cell sample can be used per-se or can be pre-coated with agents which increase the adhesiveness of the cells to the slide (e.g., poly-L-lysine or silane). The slides can be heated, frozen or subjected to certain wave-length (e.g., U.V.) in order to increase adhesiveness of the cells to the slide.

It should be noted that depending on the sample used, the cervical cell sample can be fixed with a fixative prior to staining. Methods of fixing cells are well known in the art, and include the used of fixatives such as paraformaldehyde, glutaraldehyde, acetic acid, trichloroacetic acid, and the like.

As used herein the term "staining" refers to visually highlighting cells or subcellular structures thereof.

According to some embodiments of the invention, staining of the cervical cell sample is performed using staining agents and conditions which enable differential staining of pre-malignant or malignant cervical cancer cells as opposed to normal (healthy) or inflammatory cells.

As used herein the phrase "differential staining" refers to staining a specific cell compartment (e.g., cytoplasm) of the cancerous or pre-cancerous cervical cell with a certain color, while leaving the same cell compartment of other (e.g., normal or inflammatory cells) cervical cells in the sample unstained.

As mentioned, for staining the cervical cell sample, the sample is contacted with a *Ficus elastics* plant extract.

As used herein the phrase "*Ficus elastics* plant extract" refers to at least the active ingredients of the plant [e.g., flavinoids in an oligomeric form (which may comprise 2-10 mers, e.g., $C_{26}H_{32}O_{15}$) or a polymeric form, $C_{23}H_{44}O_4$ or proanthocyanidins], or a crude plant extract, as long as its characteristic staining abilities are maintained.

The *Ficus elastics* plant extract may be prepared from various portions of the plant e.g., leaves. Guidelines for extract preparation from leaves are provided in the experimental details section of Example 1 of the Examples section which follows.

According to some embodiments of the invention, the *Ficus elastics* plant extract of the invention is a crude ethanol extract of the *Ficus elastics* plant. The ethanol extract of the *Ficus elastics* plant can include about 10% (v/v ethanol in water), about 20%, about 30%, about 40%, about 50% ethanol, about 60% ethanol, about 70% ethanol, about 80% ethanol about 90% ethanol or about 100% ethanol. Measures should be taken however not to over dilute the extract, as this may affect the subsequent staining.

Contacting the cervical cell sample with the *Ficus elastics* plant extract can be performed by applying the *Ficus elastics* plant extract on the cervical cell sample, or by dipping, soaking and/or incubating the cervical cell sample in a vessel containing same.

According to some embodiments of the invention, contacting the cervical cell sample with the *Ficus elastics* plant extract is effected for a time period which enables pre-conditioning of cancerous or pre-cancerous cervical cells such that will be differentially stained by the subsequent staining with New Fuchsin.

According to some embodiments of the invention, contacting the cervical cell sample with the *Ficus elastics* plant extract is performed for at least about 1 minute, e.g., for about 2 minutes, e.g., for about 2-20 minutes, e.g., for about 2-10 minutes, e.g., for about 2-6 minutes, e.g., for about 2-4 minutes.

As mentioned, the method according to this aspect of the invention comprises staining the cervical cell sample with the basic dye New Fuchsin.

According to some embodiments of the invention, the New Fuchsin stains the cancerous or pre-cancerous cervical cells (undifferentiated cells), which were pre-conditioned with the *Ficus elastics* plant extract, with a red color, while leaving the other cells (normal, differentiated cells) unstained.

According to some embodiments of the invention, the New Fuchsin stains the cancerous or pre-cancerous cervical cells (undifferentiated cells), which were pre-conditioned with the *Ficus elastics* plant extract and stained with Fast or Light Green, with a red color, while leaving the other cells (normal, differentiated cells) unstained.

According to some embodiments of the invention, New Fuchsin stains the cytoplasm of the cancerous or pre-cancerous cervical cells (undifferentiated cells), which were pre-conditioned with the *Ficus elastics* plant extract, with a red color, while leaving the cytoplasms in the other cells (normal, differentiated cells) unstained in red.

According to some embodiments of the invention, New Fuchsin stains the cytoplasm of the cancerous or pre-cancerous cervical cells (undifferentiated cells), which were pre-conditioned with the *Ficus elastics* plant extract and stained with Fast or Light Green, with a red color, while leaving the cytoplasms in the other cells (normal, differentiated cells) unstained in red.

According to some embodiments of the invention, New Fuchsin stains the nucleus of the cancerous or pre-cancerous cervical cells (undifferentiated cells), which were pre-conditioned with the *Ficus elastics* plant extract, with a red color.

According to some embodiments of the invention, the New Fuchsin stains the nucleus of the cancerous or pre-cancerous cervical cells (undifferentiated cells), which were pre-conditioned with the *Ficus elastics* plant extract, with a red color, while leaving the nucleus of the other cells (normal, differentiated cells) unstained in red (e.g., stained in a color other than red).

According to some embodiments of the invention, presence of a red nucleus-indicates that the cell is suspicious of being cancerous or pre-malignant. In such cases, the subsequent morphological evaluation of the cell may confirm the identification of the cell and assists in the diagnosis of the cancer or the pre-malignant lesion in the subject.

According to some embodiments of the invention, staining with New Fuchsin is performed subsequently to contacting the cervical cell sample with the *Ficus elastics* plant extract.

New Fuchsin is available as powder from various manufacturers such as Sigma (Cat. No. N0638), Fluka (Cat. No. 72200) or Merck (Cat. No. 1052260100).

New Fuchsin can be used at a concentration of at least about 0.05% [weight per volume (w/v)], at least about 0.1% (w/v), at least about 0.2% (w/v), at least about 0.3% (w/v), at least about 0.4% (w/v), e.g., about 0.5% (w/v), e.g., about 0.6% (w/v), e.g., about 0.7% (w/v).

The New Fuchsin solution can be based on an ethanol solution such as about 5% ethanol, about 10% ethanol, about 15% ethanol, about 20% ethanol, about 25% ethanol, about 30% ethanol, about 35% ethanol, about 40% ethanol, about 50% ethanol.

According to some embodiments of the invention, the concentration of the New Fuchsin used by some embodiments of the invention is about 0.5% (w/v) in a solution of 20% [volume per volume (v/v)] Ethanol in water.

Staining the cervical cell sample with New Fuchsin can be performed by applying the New Fuchsin on the cervical cell sample, or by dipping, soaking and/or incubating the cervical cell sample in a vessel containing same.

According to some embodiments of the invention, staining the cervical cell sample with New Fuchsin is effected for a time period which enables differential staining of cancerous or pre-cancerous cervical cells by New Fuchsin.

According to some embodiments of the invention, staining the cervical cell sample with New Fuchsin is performed for at least 5 seconds, e.g., at least about 10 seconds, e.g., at least about 1 minute, e.g., about 1-10 minutes.

According to some embodiments of the invention, the method further comprising digesting the mucin in the cervical cell sample (e.g., the cervical smear, the cervical cell monolayer or the cervical tissue section) with an enzyme prior to staining with the New Fuchsin.

According to some embodiments of the invention, the enzyme which digests mucin is selected from the group consisting of neuroaminidase ($\alpha(2\rightarrow3,6)$ Neuraminidase; Sigma Catalogue number N5521, Sigma-Aldrich Israel Ltd. REHOVOT ISRAEL), mucinase and sialidase (Howe, L., International Journal of STD & AIDS, Volume 10, Number 7, Pp. 442-447, which is incorporated herein by reference in its entirety).

According to some embodiments of the invention, digesting mucin can be performed prior to fixing the cells in the sample.

According to some embodiments of the invention, the method further comprising staining the cervical cell sample (e.g., the cervical smear, the cervical cell monolayer or the cervical tissue section) with an agent which differentially stains mucin in a color which is distinguishable from the color obtained by staining with New Fuchsin, Light green and Fast green.

According to some embodiments of the invention, the agent is a positively charged molecule which can bind to a negatively charged mucin. Such an agent can be, for example, Alcian blue binds to acid mucopolysaccharides. It should be noted that at an acid pH (e.g., pH of 2.5), Alcian blue stains both sulfated (sulphomucins) and carboxylated (sialomucins) mucopolysacchrides.

It should be noted that in cases where the cervical cell sample contains aggregates of cells, e.g., cell clumping of more than 10 cells, e.g., clumps of about 10-20 cells, the dyes used in the staining method are washed less efficiently.

As mentioned, the method according to this aspect of the invention comprises staining the cervical cell sample with Light Green or Fast green.

Light Green is an acidic dye which stains the cytoplasm of differentiated cells (e.g., normal cells) with green.

Fast green is an acidic dye which stains the cytoplasm of differentiated cells (e.g., normal cells) with green. The advantage of using Fast green is that the dye is more stable and does not fade out.

According to some embodiments of the invention, staining with Light Green or Fast Green is performed subsequently to staining with New Fuchsin.

Light Green is available in a powder from various manufacturers such as Merck (C.I. 42095) or Sigma (Cat. No. 62110). Fast green is available from Sigma-Aldrich (F7258) in a form of a powder.

Light Green can be used at a concentration of at least about 0.05% (w/v), at least about 0.1% (w/v), at least about 0.2% (w/v), at least about 0.4% (w/v), at least about 0.8% (w/v), at least about 1% (w/v), at least about 2% (w/v), at least about 3% (w/v), at least about 4% (w/v), at least about 5% (w/v), at least about 6% (w/v), at least about 7% (w/v), at least about 8% (w/v), at least about 9% (w/v), at least about 10% (w/v), at least about 11% (w/v), at least about 12% (w/v), at least about 13% (w/v), at least about 14% (w/v), at least about 15% (w/v), at least about 16% (w/v), at least about 17% (w/v), at least about 18% (w/v), at least about 19% (w/v), at least about 20% (w/v). The Light Green solution can be based on water or an ethanol solution such as from about 0.01% ethanol, about 5% ethanol, about 10% ethanol, about 15% ethanol, about 20% ethanol, about 25% ethanol, about 30% ethanol, about 35% ethanol, about 40% ethanol, about 50% ethanol, about 70% ethanol.

According to some embodiments of the invention, the Light Green which is used by the method of the invention is about 4% (w/v) in 20% Ethanol.

Fast Green can be used at a concentration of at least about 0.05% (w/v), at least about 0.1% (w/v), at least about 0.2% (w/v), at least about 0.4% (w/v), at least about 0.8% (w/v), at least about 1% (w/v), at least about 2% (w/v), at least about 3% (w/v), at least about 4% (w/v), at least about 5% (w/v), at least about 6% (w/v), at least about 7% (w/v), at least about 8% (w/v), at least about 9% (w/v), at least about 10% (w/v), at least about 11% (w/v), at least about 12% (w/v), at least about 13% (w/v), at least about 14% (w/v), at least about 15% (w/v), at least about 16% (w/v), at least about 17% (w/v), at least about 18% (w/v), at least about 19% (w/v), at least about 20% (w/v). The Fast Green solution can be based on water or an ethanol solution such as from about 0.01% ethanol, about 5% ethanol, about 10% ethanol, about 15% ethanol, about 20% ethanol, about 25% ethanol, about 30% ethanol, about 35% ethanol, about 40% ethanol, about 50% ethanol, about 70% ethanol.

According to some embodiments of the invention, the Fast Green which is used by the method of the invention is about 1% (w/v) in 20% Ethanol.

Staining the cervical cell sample with Light Green or Fast green can be performed by applying the Light Green or the Fast green on the cervical cell sample, or by dipping, soaking and/or incubating the cervical cell sample in a vessel containing same.

According to some embodiments of the invention, staining the cervical cell sample with Light Green or Fast green is effected for a time period which enables differential staining of normal cervical cells (differentiated cells) in green.

According to some embodiments of the invention, staining the cervical cell sample with Light Green or Fast green is performed for at least 10 seconds, e.g., at least about 30 seconds, e.g., at least about 1 minute, e.g., about 30 seconds to 10 minutes.

According to some embodiments of the invention, the method of an aspect of some embodiments of the invention further comprising staining the cervical cell sample with Hematoxylin.

Staining the cervical cell sample with Hematoxylin is performed in order to counterstain the nucleic of the cervical cells in the sample. It should be noted that counterstaining of the cell nucleic with a blue increases the contrast of the cytoplasmic stain in the cells, thus facilitates with the detection of the differential staining of the cancerous or pre-cancerous cervical cells.

Various Hematoxylin dyes can be used along with the method of the invention, these include, but are not limited to Hematoxylin Harris solution and Hematoxyline Gill III. Hematoxylin is available from various manufacturers such as Merck and Sigma.

According to some embodiments of the invention, contacting the cervical cell sample with the *Ficus elastics* plant extract is performed prior to staining cervical cell sample with Light Green or Fast green.

According to some embodiments of the invention, contacting the cervical cell sample with the *Ficus elastics* plant extract is performed prior to staining cervical cell sample with New Fuchsin.

According to some embodiments of the invention, prior to staining, the cervical cell sample (e.g., cervical smear or cervical cell monolayer) is fixed using a fixative.

Various fixative solutions can be used to fix the cervical cell sample. For example, the fixative can be an ethanol solution, a methanol solution, a Trichloroacetic acid (TCA) solution, paraformaldehyde solution, formalin solution and/or any combination thereof. For example, a combination of methanol and ethanol; a combination of ethanol and TCA; a combination of methanol and TCA; a combination of paraformaldehyde and TCA; a combination of formalin and TCA; a combination of paraformaldehyde and ethanol; a combination of paraformaldehyde and methanol; any combination of three of the abovementioned fixatives; any combination of four of the abovementioned fixatives; and all five fixatives. It should be noted that in each combination of fixative, at least 1% of each fixative is included, e.g., at least 2-5%, e.g., at least 1-10% of each fixative is included.

According to some embodiments of the invention, the method further comprising mounting the stained cervical cell sample (e.g., the cervical smear, cervical cell monolayer or cervical tissue section) with a mounting medium which comprises an anti-oxidant. It should be noted that the use of an anti-oxidant improves the stability of the stain, and prevents fading out of the dye in the stained cells.

Various known anti-oxidants can be added to the mounting medium. These include but are not limited to, anti-oxidants obtained from an extract of an apple, a wheat, a pomegranate, and the like. Other known anti-oxidants which can be used include Uric acid, Tannic acid, Glutathione, Butylated hydroxytoluene (BHT, (Butylated hydroxylanisole (BHA, (Sodium bisulfite, Propyl gallate (PG, (Vitamin C and Vitamin E. The antioxidant can be in a form of a powder, a solution, an extract and/or liquid which is added to the mounting medium.

Entellan is a non-limiting example of a mounting medium formulation which includes an anti-oxidant (e.g., available from ScienceLab.Com Inc. Houston, Tex., Catalog code: SLM31142; Entellan new, Rapid mounting medium for microscopy, Merck, Product number: 1079610100).

As mentioned above, the cervical cell sample can be a cervical tissue sample (e.g., a paraffin-embedded or frozen cervical tissue section on a microscopic slide).

Following is a non-limiting example of a staining method of a cervical tissue sample:

(a) deparaffinizing the cervical tissue sample in xylene, and subsequently (b) washing the cervical tissue sample in ethanol, and subsequently (c) washing the cervical tissue sample in water, and subsequently (d) staining the cervical tissue sample with Hematoxylin, and subsequently (e) washing the cervical tissue sample in water, and subsequently (f) contacting the cervical tissue sample with a *Ficus elastics* plant extract, and subsequently (g) washing the cervical tissue sample in water, and subsequently (h) staining the cervical tissue sample with New Fuchsin, and subsequently (i) washing the cervical tissue sample in water, and subsequently (j) incubating the cervical tissue sample in an ethanol solution, and subsequently (k) staining the cervical tissue sample with Light Green or Fast green, and subsequently (l) washing the cervical tissue sample with water, thereby staining the cervical tissue sample.

When a paraffin embedded cervical tissue section is used, the first step before staining is removing the paraffin from the issue section, which is usually performed using xylene. In case a frozen section is used, there is no need to use xylene. However, if the frozen section is not fixed (prior to being frozen), then a fixation step is preferably included prior to subjecting the cells to the staining method of some embodiments of the invention.

According to some embodiments of the invention, deparaffinizing the cervical tissue sample can be performed by heating the cervical tissue section slide at a temperature which melts the paraffin, which yet does not harm the morphology of the cells in the tissue section, followed by dissolving of the paraffin in a suitable solvent such as xylene. For example, as described in Example 1 of the Examples section which follows, deparaffinization of the cervical tissue section slide can be performed by heating the slide at 70° C. for about 15 minutes, followed by dipping the cervical tissue section slide in several vessels containing xylene (e.g., 100% xylene), for a few minutes in each vessel (e.g., 1-15 minutes, e.g., about 1-10 minutes, e.g., about 1-5 minutes, e.g., about 3 minutes).

According to some embodiments of the invention, following incubation with the xylene solution, the cervical tissue section slide is washed in an ethanol solution, which removes the excess of xylem from the tissue section. For example, the cervical tissue section slide can be washed in a vessel containing 100% Ethanol, e.g., by dipping the slide in the ethanol solution several times, e.g., 1-30 times, e.g., about 20 times, e.g., about 5-10 times, each time for a short period (e.g., a few seconds, e.g., about 1-5 seconds, e.g., for 1 second).

According to some embodiments of the invention, the cervical tissue section slide is then washed in a solution of ethanol and water, such as 96% ethanol in water, for several times, such as 1-30 dips in 96% ethanol, e.g., about 1-20 dips, e.g., about 1-10 dips, e.g., 10 dips, each for a few seconds (e.g., about 1-5 seconds, e.g., for 1 second).

According to some embodiments of the invention, to remove excess ethanol from the cervical tissue section slide, the slide is washed in water, e.g., in running distillate water for a short period, such as from about 10 seconds to about 5 minutes, e.g., for about 1-2 minutes, e.g., for about 1 minute.

According to some embodiments of the invention, to counterstain the cervical cell nuclei, the cervical tissue section slide is stained with Hematoxylin (e.g., Hematoxylin Harris solution) for a staining period of about 10 seconds to about 5 minutes, depending on the quality of the tissue section and its thickness. According to some embodiments of the invention, staining with the Hematoxylin solution is effected for about one minute.

According to some embodiments of the invention, following staining with Hematoxylin, the cervical tissue section slide is washed in water, e.g., in running distillate water, in order to remove unbound Hematoxylin dye from the tissue section. According to some embodiments of the invention, the cervical tissue section slide is washed for about 1 second to about 5 minutes with running water, e.g., for about 1 second to about 1 minute, e.g., for about 1 second to 30 seconds, e.g., for about 1 second to 10 seconds, e.g., for about 10 seconds.

According to some embodiments of the invention, in order to precondition the cervical tissue section slide for the subsequent differential staining of cancerous or pre-cancerous cervical cells, the cervical tissue section slide is contacted with the *Ficus elastics* plant extract solution. Contacting with the *Ficus elastics* plant extract can be effected for at least 1 minute, e.g., for a period of about 1 minute to about 10 minutes, for a period of about 2 minutes to about 8 minutes, e.g., for a period of about 4 minutes to about 6 minutes, e.g., for about 4 minutes.

According to some embodiments of the invention, following incubation with the *Ficus elastics* plant extract, the cervical tissue section slide is washed in water, e.g., in running DDW, in order to remove the excess of the *Ficus elastics* plant extract from the tissue section. The wash in water can be a short wash, such as for about 1-30 seconds, e.g., for about 1-20 seconds, e.g., for about 5-10 seconds, e.g., for about 10 seconds.

According to some embodiments of the invention, the cervical tissue section slide is then stained with New Fuchsin by incubating the slides in the New Fuchsin solution for a period of about 1-10 minutes, e.g., for about 2-8 minutes, e.g., for about 2-5 minutes, e.g., for about 2 minutes.

According to some embodiments of the invention, the cervical tissue section slide is then washed with water, e.g., with running DDW, in order to remove excess of New Fuchsin dye. Such a wash can be for about 1-20 seconds, e.g., for about 2-15 seconds, e.g., for about 5-10 seconds, e.g., for about 10 seconds.

According to some embodiments of the invention, following the wash in water, the cervical tissue section slide is washed in an ethanol solution, e.g., a solution of about 20-80% ethanol in water, e.g., a solution of about 30-60% ethanol in water, e.g., a solution of about 40-60% ethanol in water, e.g., in about 50% ethanol in water, for a period of about 10 seconds to about 2 minutes, e.g., for a period of 30-90 seconds, e.g., for about 75 seconds.

According to some embodiments of the invention, the cervical tissue section slide is then washed with water, e.g., running DDW, in order to remove excess of ethanol from the cervical tissue section. Washing in water is performed for a short period (e.g., about 1-60 seconds, e.g., about 10-30 seconds, e.g., about 10 seconds).

According to some embodiments of the invention, the cervical tissue section slide is then stained with Light Green. Staining with Light Green can be performed by incubating the cervical tissue section slides in the Light Green solution for about 30-120 seconds, e.g., for about 30-60 seconds, e.g., for about 50 seconds.

According to some embodiments of the invention, following Light Green staining, the cervical tissue section slide is washed in water, in order to remove excess of the Light Green dye from the tissue section. Washing in water can be performed in running water (e.g., running DDW) for a short period, such as for about 1-30 seconds, e.g., for about 5-20 seconds, e.g., for about 10 seconds. Once stained and washed, the cervical tissue section slides are dried, e.g., by air drying, although other modes of drying are also possible (e.g., drying in an incubator or over a hot plate). Air drying of the slides can last for about 10-60 minutes, e.g., for about 30 minutes.

According to some embodiments of the invention, prior to microscopical evaluation, the cervical tissue section slide is closed with cover slips by adding a mounting medium such as Entellan.

As mentioned above, the cervical cell sample can be a cervical smear (e.g., a conventional cervical smear used to date for detecting cervical cancer).

Following is a non-limiting example of a method of staining the cervical smear:

(a) fixing the cervical cell monolayer in a solution of Trichloroacetic acid (TCA), and subsequently (b) washing the cervical smear in water, and subsequently (c) staining the cervical smear with Hematoxylin, and subsequently (d) washing the cervical smear in water, and subsequently (e) contacting the cervical smear with a *Ficus elastics* plant extract, and subsequently (f) washing the cervical smear in water, and subsequently (g) incubating the cervical smear with a New Fuchsin solution, and subsequently (h) washing the cervical smear in water, and subsequently (i) incubating the cervical smear in an ethanol solution, and subsequently (j) washing the cervical smear in water, and subsequently (k) staining the cervical smear with Light Green, and subsequently (l) washing the cervical smear with water, thereby staining the cervical smear.

According to some embodiments of the invention, fixing the cervical cells comprised in the cervical smear slide is performed by incubating the slide in a solution containing TCA at a concentration in the range of about 5% to about 20%, e.g., at least about 6% and no more than about 20%, e.g., at least about 7% and no more than about 20%, e.g., at least about 8% and no more than about 20%, e.g., at least about 9% and no more than about 20%, e.g., at least about 10% and no more than about 20%, e.g., at least about 6% and no more than about 18%, e.g., at least about 8% and no more than about 16%, e.g., at least about 8% and no more than about 12%, e.g., at least about 10% TCA.

The incubation time with the TCA fixative can vary from about 10 minutes to about 2 hours, e.g., from about 20 minutes to about 90 minutes, e.g., from about 30 minutes to about 90 minutes, e.g., from about 45 minutes to about 75 minutes, e.g., about 60 minutes.

Alternatively, fixing the cervical smear slide can be performed in an ethanol or methanol fixative solution. The ethanol fixative solution may comprise from about 70% [volume/volume (v/v)] ethanol to about 100% ethanol, e.g., between about 75-100% ethanol, e.g., between about 80-100% ethanol, e.g., between about 90-100% ethanol, e.g., 100% Ethanol. The methanol fixative solution may comprise about 100% methanol. For fixation of cervical cells, the slide is incubated in the methanol or ethanol fixative solution for a period such as from about 1-30 minutes, e.g., from about 10-25 minutes, e.g., for about 15-20 minutes, e.g., for about 20 minutes.

According to some embodiments of the invention, to remove the excess of fixative (e.g., TCA, methanol or ethanol) from the cervical smear slide, the slide is washed in water, e.g., in running distillate water, running double distilled water (DDW), or deionized water for a short period, such as from about 1 second to about 5 minutes, e.g., from about 5 seconds to about 3 minutes, e.g., from about 10 seconds to about 5 minutes, e.g., for about 1-2 minutes, e.g., for about 1 minute, e.g., about 10 seconds.

According to some embodiments of the invention, to counterstain the cervical cell nuclei, the cervical smear slide is stained with Hematoxylin (e.g., Hematoxylin Harris solution, or a modified Hematoxylin solution according to Gill III for microscopy (Merck HX945424 (C.I. 75290)) for a staining period of about 10 seconds to about 20 minutes, e.g., from about 1 minute to about 15 minutes, e.g., for about 9 minutes, depending on the quality of the cervical smear slide. According to some embodiments of the invention, staining with the Hematoxylin solution is effected for about 9 minutes.

According to some embodiments of the invention, following staining with Hematoxylin, the cervical smear slide is washed in water, e.g., in running Tap water, in order to remove unbound Hematoxylin dye from the cervical smear slide. According to some embodiments of the invention, the cervical smear slide is washed for about 10 second to about 5 minutes with running Tap water, e.g., for about 20 second to about 4 minute, e.g., for about 1-2 minutes, e.g., for about 2 minutes, e.g., for about 1 minute. According to some embodiments of the invention, the cervical smear slide is further washed for about 10 seconds in running DDW, DW or deionized water.

According to some embodiments of the invention, in order to precondition the cervical smear slide for the subsequent differential staining of cancerous or pre-cancerous cervical cells, the cervical smear slide is contacted with the *Ficus elastics* plant extract solution. Contacting with the *Ficus elastics* plant extract can be effected for at least 1 minute, e.g., for a period of about 1 minute to about 10 minutes, e.g., for a period of about 2 minutes to about 8 minutes, e.g., for a period of about 4 minutes to about 6 minutes, e.g., for about 4 minutes.

According to some embodiments of the invention, following incubation with the *Ficus elastics* plant extract, the cervical smear slide is washed in water, e.g., in running DDW, DW or deionized water, in order to remove the excess of the *Ficus elastics* plant extract from the tissue section. The wash in water can be a short wash, such as for about 1-30 seconds, e.g., for about 1-20 seconds, e.g., for about 5-10 seconds, e.g., for about 10 seconds.

According to some embodiments of the invention, the cervical smear slide is then stained with New Fuchsin by incubating the slide in a New Fuchsin solution (in ethanol) for a period of about 1-10 minutes, e.g., for about 1-8 minutes, e.g., for about 1-6 minutes, e.g., for about 4 minutes, e.g., for about 1 minute. The concentration of the New Fuchsin in the ethanol solution can be from about 0.1-5% (weight per volume (w/v)) New Fuchsin an ethanol solution of about 5-70% ethanol in water (v/v).

According to some embodiments of the invention, the cervical smear slide is then washed with water, e.g., with running DDW, DW or deionized water in order to remove excess of New Fuchsin dye. Such a wash can be for about 1-20 seconds, e.g., for about 2-15 seconds, e.g., for about 5-10 seconds, e.g., for about 10 seconds.

According to some embodiments of the invention, following the wash in water, the cervical smear slide is washed in an ethanol solution, e.g., a solution of about 5-80% ethanol in water, a solution of about 5-70% ethanol in water, e.g. from about 20-80% ethanol in water, e.g., a solution of about 30-60% ethanol in water, e.g., a solution of about 40-60% ethanol in water, e.g., in about 50% ethanol in water. The wash in the ethanol solution can be performed by incubating in the ethanol solution of by several short dips in the ethanol solution, e.g., about 5-30 dips, e.g., about 10-30 dips, e.g. about 5-20 dips, e.g., about 20 dips, e.g., about 10 times, wherein each dip last for about 1-3 seconds, e.g., for 1 second.

According to some embodiments of the invention, the cervical smear slide is then washed with water, e.g., running DDW, DW or deionized water in order to remove excess of ethanol from the cervical smear. Washing in water is performed for a short period (e.g., about 1-60 seconds, e.g., about 10-30 seconds, e.g., about 10 seconds).

According to some embodiments of the invention, the cervical smear slide is then stained with Light Green. The light green solution can be in the range of about 0.1-4% (w/v) light green in an ethanol solution of about 0.1-70% ethanol in water (v/v), for example a solution of 0.2% light green in 1% ethanol, e.g., a solution of 4% Light Green in 20% ethanol. Staining with Light Green can be performed by incubating the cervical smear slide in the Light Green solution for about 1-10 minutes, e.g., for about 2-8 minutes, for about 5-6 minutes, e.g., for about 5.5 minutes.

According to some embodiments of the invention, following Light Green staining, the cervical smear slide is washed in water, in order to remove excess of the Light Green dye from the cervical smear. Washing in water can be performed in running water (e.g., running DDW, DW or deionized water) for a short period, such as for about 1-30 seconds, e.g., for about 5-20 seconds, e.g., for about 10 seconds.

According to some embodiments of the invention, following the wash in running water, the slides are further washed in an ethanol solution (e.g., a solution in the range of about 5% to about 70%, e.g., about 40% ethanol in water) by several dips, e.g., for about 5 to 20 dips, e.g., about 7 dips) and subsequently washed in running DDW, DW or deionized water for about 1-20 seconds, e.g., 10 seconds.

Once stained and washed, the cervical smear slide is dried, e.g., by air drying, for about 10-60 minutes, e.g., for about 30 minutes, mounted with a mounting medium such as Eukitt or Entellan, and covered with cover slips. It should be noted, that before mounting in Entellan, the slides are optionally dipped in 100% xylene (e.g., 1-2 dips) and then covered with Entellan and a coverslip.

As mentioned above, the cervical cell sample can be a cervical cell monolayer such as a liquid-based cervical monolayer. Methods of preparing liquid-base cervical monolayers include, but are not limited to, the ThinPrep™ method [Hologic] or the SURE PATH™ [Becton Dickinson (BD) 1 Becton Drive, Franklin Lakes, N.J., USA] method.

Following is a non-limiting example of a method of staining the cervical cell monolayer:

(a) fixing the cervical cell monolayer in a solution of Trichloroacetic acid (TCA), and subsequently (b) washing the cervical cell monolayer in water, and subsequently (c) staining the cervical cell monolayer with Hematoxylin, and subsequently (d) washing the cervical cell monolayer in water, and subsequently (e) contacting the cervical cell monolayer with a *Ficus elastics* plant extract, and subsequently (f) washing the cervical cell monolayer in water, and subsequently (g) staining the cervical cell monolayer with New Fuchsin, and subsequently (h) washing the cervical cell monolayer in water, and subsequently (i) optionally, incubating the cervical cell monolayer in an ethanol solution, and subsequently (j) optionally, washing the cervical cell monolayer in water, and subsequently (k) staining the cervical cell monolayer with Light Green or Fast green, and subsequently (l) washing the cervical cell monolayer with water, and subsequently (m) washing the cervical cell monolayer in an ethanol solution, and subsequently (n) washing the cervical cell monolayer with water, thereby staining the cervical cell monolayer.

According to some embodiments of the invention, prior to staining, the cervical cell monolayer slide is fixed using a fixative such as Trichloroacetic acid (TCA), e.g., in a solution comprising about 1-20% TCA, e.g., about 5-20% TCA, e.g., about 5-15% TCA, e.g., about 10% TCA. Fixing the cervical cell monolayer slide is effected for about 10 minutes to about 2 hours, e.g., from about 20 minutes to about 2 hours, e.g., for about 1 hour. Following fixation, the cervical cell monolayer slide is washed in water (DDW, DW or deionized water) in order to remove excess of fixative from the cervical cell monolayer sample. The washes (e.g., 2-6 washes, e.g., 4 washes) can be in running deionized water (from both sides of the slide), each for about 2-10 seconds each. The back of the slide can be then dried on paper towel.

According to some embodiments of the invention, to counterstain the cervical cell nuclei, the cervical cell monolayer slide is stained with Hematoxylin (e.g., Hematoxylin Gill III solution for microscopy, or Hematoxylin Harris) for a staining period of about 1-20 minutes, e.g., about 1-15 minutes, depending on the quality of the cervical cell monolayer slide. According to some embodiments of the invention, staining with the Hematoxylin solution is effected for about 5-15 minutes, e.g., for about 5-10 minutes, e.g., for about 9 minutes.

According to some embodiments of the invention, in order to remove unbound Hematoxylin dye from the cervical cell monolayer slide, the slide is washed in water, e.g., by incubating the slide in Tap water for about 1 minute, and then by running DDW, DW or deionized water for 10 seconds [or by dipping 3-6 times (e.g., 4 times, each for about 2 seconds) in running deionized water].

According to some embodiments of the invention, in order to precondition the cervical cell monolayer slide for the subsequent differential staining of cancerous or pre-cancerous cervical cells, the cervical cell monolayer slide is contacted with the *Ficus elastics* plant extract solution. Contacting with the *Ficus elastics* plant extract can be effected for at least 1 minute, e.g., for a period of about 1 minute to about 10 minutes, e.g., for a period of about 2 minutes to about 8 minutes, e.g., for a period of about 2 minutes, e.g., for 4 minutes.

According to some embodiments of the invention, in order to remove the excess of the *Ficus elastics* plant extract from the cervical cell monolayer, the slide is washed in running DDW, DW or deionized water for 10 seconds, or by dipping in DDW, DW or deionized water 4 times, each for about 2 seconds.

According to some embodiments of the invention, the cervical cell monolayer slide is then stained with New Fuchsin solution by incubating the slide in the New Fuchsin solution for a period of about 10 seconds to about 5 minutes, e.g., from about 10 seconds to about 3 minutes, e.g., for about 30 seconds to 3 minutes, e.g., for about 1 minute. The New Fuchsin solution can be from about 0.1% to about 5% New Fuchsin (w/v) in an ethanol solution of about 5% to 70% ethanol in water (v/v). According to some embodiments of the invention, the New Fuchsin solution is of 0.5% New Fuchsin in 20% Ethanol.

According to some embodiments of the invention, the cervical cell monolayer slide is then washed by running DDW, DW or deionized water for about 10 seconds, or dipped for several times (e.g., 3-6 times, e.g., 4 times) with water, e.g., with running deionized water, DDW or DW, in order to remove excess of New Fuchsin dye. Each wash can be for about 1-20 seconds, e.g., for about 2-15 seconds, e.g., for about 5-10 seconds, e.g., for about 10 seconds.

The cervical cell monolayer slides can be then stained with Fast green or Light green.

According to some embodiments of the invention, when light green is used, the slides are further washed in an ethanol solution and then in water. According to some embodiments of the invention, when Fast green is used, the slides can be directly subjected to Fast green staining as described below.

According to some embodiments of the invention, following the wash in water, the cervical cell monolayer slide is washed in an ethanol solution, e.g., a solution of about 20-80% ethanol in water, e.g., a solution of about 30-60% ethanol in water, e.g., a solution of about 40-60% ethanol in water, e.g., in about 50% ethanol in water. The wash in the ethanol solution can be performed by incubating in the ethanol solution of by several short dips in the ethanol solution, e.g., about 10-50 dips, e.g., about 30-40 dips, e.g., 35 dips, wherein each dip last for about 1-3 seconds, e.g., for 2 seconds.

According to some embodiments of the invention, the cervical cell monolayer slide is then washed several times (e.g., 3-6 times, e.g., 4 times) with water, e.g., running deionized water, in order to remove excess of ethanol from the cervical cell monolayer. Each wash in water is performed for a short period (e.g., about 1-60 seconds, e.g., about 10-30 seconds, e.g., about 10 seconds).

According to some embodiments of the invention, the cervical cell monolayer slide is then stained with Light Green. Staining with Light Green can be performed by incubating the cervical cell monolayer slides in the Light Green solution (e.g., 4% Light Green in 20% ethanol) for about 0.5-10 minutes, e.g., for about 1-5 minutes, for about 2-3 minutes, e.g., for about 2 minutes.

According to some embodiments of the invention, the cervical cell monolayer slide is then stained with Fast Green. Staining with Fast Green can be performed by incubating the cervical cell monolayer slides in the Fast Green solution for about 5 seconds to about 2 minutes, e.g., for about 10 seconds to about 2 minutes, e.g., for about 20 seconds to about 1 minute, e.g., for about 40-50 seconds, e.g., 45 seconds. The Fast green solution can be a solution of Fast green in an ethanol solution such as a solution which comprises about 0.1% to about 5% of Fast Green in an ethanol solution of about 5% to about 70% ethanol in water (v/v). For example, the Fast green solution can include about 1% Fast green in a 20% ethanol/water solution.

According to some embodiments of the invention, following Light Green or Fast Green staining, the cervical cell monolayer slide is washed in water (e.g., running DDW, DW or deionized water), in order to remove unbound Light Green or Fast Green dye from the cervical cell monolayer. Washing in water can be performed by several washes (e.g., 3-6 times, e.g., 4 times) for a short period, such as for about 1-30 seconds, e.g., for about 5-20 seconds, e.g., for about 10 seconds.

According to some embodiments of the invention, the cervical cell monolayer slide is then washed in ethanol, e.g., by dipping (short dips, each of about 1-2 seconds) in an ethanol solution in the range of about 5% to about 70% ethanol in water, e.g., about 40% ethanol in water, for several times, such as 5-15 times (e.g., 10 times), followed by washing the cervical cell monolayer in water, e.g., running deionized water, for about 4 times, each wash for about 1-60 seconds (e.g., 2 seconds). Following the wash in ethanol, the slides can be washed by running DDW, DW, or deionized water for 10 seconds.

According to some embodiments of the invention, once stained and washed, the cervical cell monolayer slide is dried, e.g., by air drying, for about 10-60 minutes, e.g., for about 30 minutes, mounted with a mounting medium such as Eukitt or Entellan, and covered with cover slips.

It should be noted that any of the staining protocols described hereinabove with respect to a liquid base sample can be also implemented for a conventional cervical smear and/or for a tissue biopsy (e.g., a paraffin-embedded or a frozen section).

Once stained by the method of some embodiments of the invention, the cervical cell sample is further evaluated using a microscope and/or an image analysis system (e.g., an automated image analysis device) for the presence of at least one cervical cell having a red cytoplasm in the sample. The intensity of the red staining can be quantified (e.g., by pixels) and compared to a pre-determined threshold. A cell having a cytoplasm with a red intensity which is above a pre-determined threshold is considered to be differentially stained.

According to some embodiments of the invention cells which are differentially stained by the method of some embodiments of the invention (e.g., with a red cytoplasm) are undifferentiated cells such as pre-malignant or malignant cervical cancer cells.

According to some embodiments of the invention, a cell having a green cytoplasm after being stained with the staining method of some embodiments of the invention is considered a normal cervical cell.

According to some embodiments of the invention the cells which are differentially stained by the method of some embodiments of the invention are further evaluated by their morphological characteristics in order to classify them according to accepted histological guidelines and determine cancerous or pre-cancerous staging.

Following is a non-limiting description of morphological characteristics of cancerous or pre-cancerous cells which can be present in the cervical cell sample (cytology sample) of some embodiments of the invention (description obtained from Diane Solomon, Ritu Nayar, Eds: The Bethesda System for Reporting Cervical Cytology. Definitions, criteria and explanatory notes; Second Edition. 2004; which is fully incorporated by reference in its entirety).

Neoplastic Cells

Atypical Squamous Cells of Undetermined Significance (ASC-US)—

Nuclei area is approximately 2-3 times of the area of the nucleus of normal intermediate squamous cell (nuclei area of AC-US is approximately 35 μm$^2$). Slightly increased ratio of nuclear to cytoplasmic area. Minimal nuclear hyperchromasia and irregularity in chromatin distribution or nuclear shape. Typical ASC-US cells have the size and shape of superficial or intermediate squamous cells (See for example, FIG. 22).

Low-Grade Squamous Intraepithelial Lesion (LSIL)—

Cells occur singly (i.e., as single cells which do not touch or overlap each other) or in clusters. Overall cell size is large, with fairly abundant "mature" well-defined cytoplasm. Nuclear enlargement more than three times the area of normal intermediate nuclei results in a slightly increased nuclear to cytoplasmic ratio. Variable degrees of nuclear hyperchromasia are accompanied by variations in nuclear size, number, and shape. Binucleation and multinucleation are common but single nucleus is also present in some cells. Chromatin is often uniformly distributed, but coarsely granular; alternatively the chromatin may appear smudged. Nucleoli are generally absent or inconspicuous if present. Contour of nuclear membranes is often slightly irregular, but may be smooth. Cells have distinct cytoplasmic borders. Non-limiting examples of LSIL cells are shown in FIG. 23).

High-Grade Squamous Intraepithelial Lesion (HSIL)—

Cells occur singly, in clusters, or syncytial-like aggregates. Overall cell size is variable, and ranges from cells that are similar in size to those observed in LSIL to quite small basal-type cells. Nuclear hyperchromasia is accompanied by variations in nuclear size and shape. Degree of nuclear enlargement is more variable than that seen in LSIL. Some HSIL cells have the same degree of nuclear enlargement as in LSIL, but the cytoplasmic area is decreased, leading to marked increase in the nuclear/cytoplasmic ratio. Other cells have very high nuclear/cytoplasmic ratios, but the actual size of the nuclei may be considerably smaller than that of LSIL. Chromatin may be fine or coarsely granular and evenly distributed. Contour of the nuclear membrane is quite irregular and frequently demonstrates prominent indentations or grooves. Nucleoli are generally absent, but may occasionally be seen, particularly when HSIL extends into endocervical gland spaces. Non-limiting examples of HSIL cells are shown in FIG. 24).

Squamous Cell Carcinoma

Keratinizing Squamous Cell Carcinoma—

Relatively few cells may be present; often as isolated single cells and less commonly in aggregates. Marked variation in cellular size and shape is typical, with caudate and spindle cells. Nuclei also vary markedly in size, nuclear membranes may be irregular in configuration, and numerous dense opaque nuclei are often present. Chromatin pattern, when discernible, is coarsely granular and irregularly distributed with parachromatin clearing. Macronucleoli may be seen but are less common than in nonkeratinizing SCC. Non-limiting examples of keratinizing SCC are shown in FIG. 25).

Nonkeratinizing Squamous Cell Carcinoma—

Cells occur singly or in syncytial aggregates with poorly defined cell borders. Cells are frequently somewhat smaller than those of many HSIL, but display most of the features of HSIL. Nuclei demonstrate markedly irregular distribution of coarsely clumped chromatin. May show prominent macronucleoli. Non-limiting examples of non-keratinizing SCC are shown in FIG. 26).

Following is a non-limiting description of morphological characteristics of normal superficial squamous cells (basal, intermediate and mature) and normal endocervical cells which can be present in the cervical cell sample (cytology sample) of some embodiments of the invention (description obtained from Diane Solomon, Ritu Nayar, Eds: The Bethesda System for Reporting Cervical Cytology. Definitions, criteria and explanatory notes; Second Edition. 2004; which is fully incorporated by reference in its entirety).

Basal Squamous Cell—

Nuclear/cytoplasmic ratio: Increased; Cell size: Variable; Nuclear membrane: Smooth; Nuclear content: Chromatin uniformly distributed; Number of nuclei: One; Cell shape: Oval.

Intermediate Squamous Cell—

Nuclear/cytoplasmic ratio: Slightly increased as compared to a mature squamous cell. Cell size: Variable; Nuclear membrane: Smooth; Nuclear content: Chromatin uniformly distributed; Number of nuclei: One; Cell shape: Polygonal or oval.

Mature Squamous Cell—

Nuclear/cytoplasmic ratio: Small (pyknotic) nucleus Nuclear membrane: Smooth; Nuclear content: Chromatin: uniformly distributed; Nucleoli: usually absent; Number of nuclei: One; Cell shape: Polygonal Normal Endocervical Cells—

Cells usually present in clusters. Distinct cytoplasmic borders in the clusters giving "honeycomb" appearance. In addition, the endocervical cells are easily identified by their typical-eccentric nucleus. Additionally, focusing up and down through the cluster reveals normal spacing of cells, distinct cytoplasmic borders, and bland nuclear chromatin. Nuclear membrane is smooth. In contrast to endocervical cells, dysplastic/neoplastic clusters show more crowding (even within a single layer of cells), nuclear enlargement, nuclear membrane irregularity, and abnormal chromatin pattern. Non-limiting examples of endocervical cells are shown in FIG. 21.

Following is a non-limiting description of morphological characteristics of neoplasia in cervical biopsies (histology sample) according to some embodiments of the invention (description obtained from Diagnostic Histopathology of Tumors third edition volume 1. 2007. Christopher D. M Fletcher; which is fully incorporated by reference in its entirety).

Squamous Intraepithelial Neoplasia [Squamous Intraepithelial Lesions; Cervical Intraepithelial Neoplasia (CIN)]—

High-grade squamous intraepithelial lesions are characterized by nuclear atypia in all levels of the epithelium with a variable degree of surface maturation. Lesions that exhibit surface koilocytotic change and epithelial maturation correspond to CIN2, whereas those with little to no maturation correspond to CIN3. These lesions are distinguished from low-grade squamous intraepithelial lesions by: (1) the presence of nuclear atypia in the lower layers; (2) increased mitotic index with mitoses in the upper half of the epithelium; (3) loss of cell polarity; (4) abnormal mitotic figures and, in some cases, (5) the presence of markedly atypical, bizarre cells. Non-limiting examples of CIN3 is shown in FIG. 27; and non-limiting examples of CIN2 is shown in FIG. 28.

Invasive Squamous Cell Carcinoma

Keratinizing—

This tumor type shows conspicuous evidence of Keratinization in the form of Keratin pearls, keratohyline granules, individual keratinized cells, and nests of squamous cells with central Keratinization. These tumors are usually classified as well differentiated and often have a pushing border of invasion.

Non-Keratinizing—

This tumor is composed of histologically recognizable squamous cells, which are large and polygonal with eosinophilic cytoplasm and cellular bridges, but which lack keratin pearl formation, keratohyaline granules, or nests of squamous cells with central Keratinization. A greater degree of nuclear pleomorphism and an infiltrative border with associated inflammation are often present and most tumors are usually classified as moderately differentiated. Non-limiting examples of non-keratinizing SCC is shown in FIG. 29.

According to some embodiments of the invention, the method further comprising detecting an expression level above a pre-determined threshold of a cervical malignant or a cervical pre-malignant marker, wherein the expression level above the pre-determined threshold of the cervical malignant or of the cervical pre-malignant marker is indicative that the cervical cell is a malignant or a pre-malignant cell, thereby identifying the cervical malignant or cervical pre-malignant cell.

As used herein the phrase "an expression level above a predetermined threshold" refers to a fold increase (e.g., degree of upregulation) which is higher than a predetermined threshold such as at least twice, at least three times, at least four time, at least five times, at least six times, at least seven times, at least eight times, at least nine times, at least 20 times, at least 50 times, at least 100 times, at least 200 times, at least 500 times, at least 1000 times higher than a reference expression level.

As used herein the phrase "reference expression level" refers to the expression level of a gene product (e.g., the cervical cancer marker or the cervical pre-cancerous marker) in a cell of a control, healthy subject, e.g., not affected by the disease, or a non-affected cell. It should be noted that the reference expression level can be obtained from the literature, or can be determined in cells of control subjects (e.g., from the same tissue type, cervical cells).

According to some embodiments of the invention, the reference expression data is obtained from at least one control, healthy subject, e.g., from at least 2, from at least 3, from at least 4, from at least 5, from at least 6, from at least 7, from at least 8, from at least 9, from at least 10, from at least 20, from at least 30, from at least 40, from at least 50, from at least 100 or more control, healthy subjects.

It should be noted that when more than one reference subjects is used, the reference expression data may comprise an average of the expression level of several or all subjects, and those of skills in the art are capable of averaging expression levels from 2 or more subject, using e.g., normalized expression values.

According to some embodiments of the invention, the reference expression level is absence of the cancerous or pre-malignant cancerous marker. In some embodiments of the invention, presence of the cancerous or pre-malignant cancerous marker as compared to absence of the marker in a control subject or control cell (e.g., reference expression level is zero) is indicative of a cancerous or a pre-cancerous cell (depending on the marker which is detected).

Following is a non-limiting list of cancerous/premalignant markers which detection thereof in cervical cells indicates that the cervical cell is a malignant or a pre-malignant cell.

TABLE 1

| Marker | Marker amino acid sequence (SEQ ID NO) | Marker nucleic acid sequence (SEQ ID NO) | Method | Indication of cancer |
|---|---|---|---|---|
| HPV (human papillomavirus) | | | digene HC2 HPV DNA Test (by Qiagen), detects for presence of a variety of HPV strains | |
| Hypoxia-inducible factor 1-alpha (HIF-1alpha) | 2 | 1 | Immunohistochemistry (Birner P, et al., Cancer Res. 2000; 60: 4693-6) | Cervical cancer, but can be use in many different kinds of cancer |

TABLE 1-continued

| Marker amino acid sequence (SEQ ID NO) | Marker nucleic acid sequence (SEQ ID NO) | Method | Indication of cancer |
|---|---|---|---|
| Id-1 (Inhibitor of differentiation/DNA binding) | 4 | 3 | Immunohistochemistry (Schindl M, et al., Cancer Res. 2001; 61: 5703-6) | Cervical cancer |
| $p16^{INK4a}$ | 6 | 5 | Immunohistochemistry (Tsoumpou I., et al., Cancer Treatment Reviews 35: 210-220, 2009; Negri G, et al., Am J Surg Pathol. 2003, 27: 187-93) | Cervical cancer |
| p21WAF1/CIP1 [p21waf1/cip1 encodes a cyclin-dependent kinase inhibitor that is transcriptionally activated by the p53 tumor suppressor gene, transforming growth factor beta 1] | 8 | 7 | Immunohistochemistry (Lu-X, et al., Cancer. 1998; 82: 2409-17) | Cervical cancer |
| Tn antigen (Tn-Ag) | Tn antigen carbohydrate (GalNac α(1-O)-Ser/Thr) | | Tn-Ag can be measured by the avidin-biotin-peroxidase (ABC) method with peanut (*Arachis hypogaea*) lectin (PNA) and Vicia villosa agglutinin (VVA) (Hirao T, et al., Cancer. 1993, 72: 154-9) | Cervical cancer |
| P53 | 10 | 9 | Immunohistochemistry (Kaserer K., et al., J Pathol. 2000, 190: 450-6) | |
| Proliferation markers | | | | |
| PCNA (proliferating cell nuclear antigen (PCNA) | 14 | 13 | Immunohistochemistry (Raucci F, et al., J Chem Neuroanat. 2006 Dec; 32(2-4): 127-42) | Proliferation marker can be used for diagnosis of cervical cancer |
| Ki-67 protein | 12 | 11 | Immunohistochemistry (Scholzen T, Gerdes J; J Cell Physiol. 2000 Mar; 182(3): 311-22) | Proliferation marker can be used for diagnosis of cervical cancer |
| BrdU | | | Immunohistochemistry (using an anti BrDu antibody; BD Bioscience, Cat No. 550803; Cat No. 551321) | Proliferation marker can be used for diagnosis of cervical cancer |

Each of the cited references for the staining protocols is incorporated herein by references in its entirety.

The expression level of the cervical malignant or a cervical pre-malignant marker can be detected using a high affinity agent capable of binding to the cervical malignant or pre-malignant marker.

According to some embodiments the high affinity agent is an antibody which specifically binds to the cervical malignant or cervical pre-malignant marker.

The term "antibody" as used in this invention includes intact molecules as well as functional fragments thereof, such as Fab, F(ab')$_2$, and Fv that are capable of binding to macrophages. These functional antibody fragments are defined as follows: (1) Fab, the fragment which contains a monovalent antigen-binding fragment of an antibody molecule, can be produced by digestion of whole antibody with the enzyme papain to yield an intact light chain and a portion of one heavy chain; (2) Fab', the fragment of an antibody molecule that can be obtained by treating whole antibody with pepsin, followed by reduction, to yield an intact light chain and a portion of the heavy chain; two Fab' fragments are obtained per antibody molecule; (3) (Fab')2, the fragment of the antibody that can be obtained by treating whole antibody with the enzyme pepsin without subsequent reduction; F(ab')2 is a dimer of two Fab' fragments held together by two disulfide bonds; (4) Fv, defined as a genetically engineered fragment containing the variable region of the light chain and the variable region of the heavy chain expressed as two chains; and (5) Single chain antibody ("SCA"), a genetically engineered molecule containing the variable region of the light chain and the variable region of the heavy chain, linked by a suitable polypeptide linker as a genetically fused single chain molecule.

Methods of producing polyclonal and monoclonal antibodies as well as fragments thereof are well known in the art (See for example, Harlow and Lane, Antibodies: A Laboratory Manual, Cold Spring Harbor Laboratory, New York, 1988, incorporated herein by reference).

Antibody fragments according to the present invention can be prepared by proteolytic hydrolysis of the antibody or by expression in E. coli or mammalian cells (e.g. Chinese hamster ovary cell culture or other protein expression systems) of DNA encoding the fragment. Antibody fragments can be obtained by pepsin or papain digestion of whole antibodies by conventional methods. For example, antibody fragments can be produced by enzymatic cleavage of antibodies with pepsin to provide a 5S fragment denoted F(ab')2. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly. These methods are described, for example, by Goldenberg, U.S. Pat. Nos. 4,036,945 and 4,331,647, and references contained therein, which patents are hereby incorporated by reference in their entirety. See also Porter, R. R. [Biochem. J. 73: 119-126 (1959)]. Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

Fv fragments comprise an association of VH and VL chains. This association may be noncovalent, as described in Inbar et al. [Proc. Nat'l Acad. Sci. USA 69:2659-62 (19720]. Alternatively, the variable chains can be linked by an intermolecular disulfide bond or cross-linked by chemicals such as glutaraldehyde. Preferably, the Fv fragments comprise VH and VL chains connected by a peptide linker. These single-chain antigen binding proteins (sFv) are prepared by constructing a structural gene comprising DNA sequences encoding the VH and VL domains connected by an oligonucleotide. The structural gene is inserted into an expression vector, which is subsequently introduced into a host cell such as E. coli. The recombinant host cells synthesize a single polypeptide chain with a linker peptide bridging the two V domains. Methods for producing sFvs are described, for example, by [Whitlow and Filpula, Methods 2: 97-105 (1991); Bird et al., Science 242:423-426 (1988); Pack et al., Bio/Technology 11:1271-77 (1993); and U.S. Pat. No. 4,946,778, which is hereby incorporated by reference in its entirety.

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See, for example, Larrick and Fry [Methods, 2: 106-10 (1991)].

According to some embodiments of the invention the antibody is conjugated to an identifiable or detectable moiety. The identifiable moiety can be a label which is directly visualized (e.g., a fluorescent molecule, a radioactive molecule) or a member of a binding (affinity) pair, which is identifiable via its interaction with an additional member of the binding pair (e.g., antibody-antigen pairs, enzyme-substrate pairs). Table 2, hereinbelow, provides examples of sequences of identifiable moieties.

TABLE 2

| Identifiable Moiety | Amino Acid sequence (Genbank Accession No.) | Amino acid SEQ ID NO: | Nucleic Acid sequence (Genbank Accession No.) | Nucleic acid SEQ ID NO: |
|---|---|---|---|---|
| Green Fluorescent protein | AAL33912 | 15 | AF435427 | 16 |
| Alkaline phosphatase | AAK73766 | 17 | AY042185 | 18 |
| Peroxidase | NP_568674 | 19 | NM_124071 | 20 |
| Histidine tag | Amino acid coordinates 264-269 of Genbank Accession No. AAK09208 | 21 | Nucleic acid coordinates 790-807 of Genbank Accession No. AF329457 | 22 |
| Myc tag | Amino acid coordinates 273-283 of Genbank Accession No. AAK09208 | 21 | Nucleic acid coordinates 817-849 of Genbank Accession No. AF329457 | 22 |
| Biotin lygase tag | NP_561589 | 23 | NC_003366 | 24 |
| orange fluorescent protein | AAL33917 | 25 | AF435432 | 26 |
| Beta galactosidase | NP_201186 | 27 | NM_125776 | 28 |
| Fluorescein isothiocyanate | — | — | — | — |
| Streptavidin | AAM49066 | 29 | AF283893 | 30 |

According to some embodiments of the invention, the identifiable moiety is conjugated by translationally fusing the polynucleotide encoding the antibody of the invention with the nucleic acid sequence encoding the identifiable moiety.

Additionally or alternatively, the identifiable moiety can be chemically conjugated (coupled) to the antibody of the invention, using any conjugation method known to one skilled in the art. For example, a peptide can be conjugated to an antibody of interest, using a 3-(2-pyridyldithio)propionic acid N-hydroxysuccinimide ester (also called N-succinimidyl 3-(2pyridyldithio) propionate) ("SDPD") (Sigma, Cat. No. P-3415; see e.g., Cumber et al. 1985, Methods of Enzymology 112: 207-224), a glutaraldehyde conjugation procedure (see e.g., G. T. Hermanson 1996, "Antibody Modification and Conjugation, in Bioconjugate Techniques, Academic Press, San Diego) or a carbodiimide conjugation procedure [see e.g., J. March, Advanced Organic Chemistry: Reaction's, Mechanism, and Structure, pp. 349-50 & 372-74 (3d ed.), 1985; B. Neises et al. 1978, Angew Chem., Int. Ed. Engl. 17:522; A. Hassner et al. 1978, Tetrahedron Lett. 4475; E. P. Boden et al. 1986, J. Org. Chem. 50:2394 and L. J. Mathias 1979, Synthesis 561].

The antibody can be used in a variety of known methods such as immunohistochemistry, immunofluorescence and radio-immunolabeling in situ (using a radio-labeled antibody).

Following is a non-limiting example of an immunohistochemical analysis. This method involves detection of a substrate in situ in fixed cells by substrate specific antibodies. The substrate specific antibodies may be enzyme linked or linked to fluorophores. Detection is by microscopy and subjective or automatic evaluation. If enzyme linked antibodies are employed, a colorimetric reaction may be required. It will be appreciated that immunohistochemistry is often followed by counterstaining of the cell nuclei using for example Hematoxylin or Giemsa stain. For immunofluorescence, the antibody can be directly or indirectly (e.g., via a secondary antibody) to a fluorescent moiety.

According to some embodiments of the invention the level of expression of the cervical malignant or pre-malignant cancer is detected using a high affinity substrate, e.g., in an in situ activity assay. According to this method, a chromogenic substrate is applied on the cells containing an active enzyme and the enzyme catalyzes a reaction in which the substrate is decomposed to produce a chromogenic product visible by a light or a fluorescent microscope.

According to some embodiments of the invention the high affinity agent is a polynucleotide which specifically hybridizes to an mRNA transcript encoding the cervical malignant or cervical pre-malignant marker. Non-limiting examples of polynucleotides which can hybridize to mRNA include DNA or RNA probes which are used for in situ hybridization, DNA or RNA oligonucleotides which can be used for in situ RT-PCR (reverse transcription coupled with polymerase chain reaction).

According to some embodiments of the invention the high affinity agent is a polynucleotide which specifically hybridizes to a specific DNA sequence that is used as a marker for cervical cancer (e.g., DNA of various HPV strains, a specific cancer-associated mutation, duplication, inversion, deletion, insertion, translocation and the like). Such a polynucleotide can be a DNA or RNA probe or PCR primer(s) which can detect a specific DNA sequence (e.g., foreign DNA sequence, non-human sequence, such as viral sequence), as well as a mutation in an endogenous DNA sequence (for amplification of specific markers in situ, such as duplications, deletions, inversions), using for example, in situ PCR.

Various methods can be used to label the polynucleotide of the invention. These include fluorescent labeling with a fluorophore conjugated via a linker or a chemical bond to at least one nucleotide, or the use of a covalently conjugated enzyme (e.g., Horse Radish Peroxidase) and a covalently conjugated substrate (e.g., o-phenylenediamine) which upon interaction therebetween yield a colorimetric or fluorescent color. Alternatively, the polynucleotide can be radiolabeled.

As used herein the term "fluorophore" refers to any entity which can be excited by light to emit fluorescence. Such a fluorphore can be an artificial or a naturally occurring molecule (e.g., fluorescein, Texas Red, rhodamine), or a quantum dot. Quantum dots are coated nanocrystals fabricated from semiconductor materials in which the emission spectrum is controlled by the nanocrystal size. Quantum dots have a wide absorption spectrum, allowing simultaneous emission of fluorescence of various colors with a single excitation source. Quantum dots can be modified with large number of small molecules and linker groups such as conjugation of amino (PEG) or carboxyl quantum dots to streptavidin (Quantum Dot Corporation, Hayward, Calif., USA).

The polynucleotide can be used in a variety of in situ detection methods such as in situ hybridization and in situ RT-PCR, which are well known in the art.

Following is a non-limiting example of performing in situ hybridization.

RNA In Situ Hybridization Stain:

In this method DNA or RNA probes are attached to the RNA molecules present in the cells. Generally, the cells are first fixed to microscopic slides to preserve the cellular structure and to prevent the RNA molecules from being degraded and then are subjected to hybridization buffer containing the labeled probe. The hybridization buffer includes reagents such as formamide and salts (e.g., sodium chloride and sodium citrate) which enable specific hybridization of the DNA or RNA probes with their target mRNA molecules in situ while avoiding non-specific binding of probe. Those of skills in the art are capable of adjusting the hybridization conditions (i.e., temperature, concentration of salts and formamide and the like) to specific probes and types of cells. Following hybridization, any unbound probe is washed off and the bound probe is detected using known methods. For example, if a radio-labeled probe is used, then the slide is subjected to a photographic emulsion which reveals signals generated using radio-labeled probes; if the probe was labeled with an enzyme then the enzyme-specific substrate is added for the formation of a colorimetric reaction; if the probe is labeled using a fluorescent label, then the bound probe is revealed using a fluorescent microscope; if the probe is labeled using a tag (e.g., digoxigenin, biotin, and the like) then the bound probe can be detected following interaction with a tag-specific antibody which can be detected using known methods.

In Situ RT-PCR Stain:

This method is described in Nuovo G J, et al. [Intracellular localization of polymerase chain reaction (PCR)-amplified hepatitis C cDNA. Am J Surg Pathol. 1993, 17: 683-90] and Komminoth P, et al. [Evaluation of methods for hepatitis C virus detection in archival liver biopsies. Comparison of histology, immunohistochemistry, in situ hybridization, reverse transcriptase polymerase chain reaction (RT-PCR) and in situ RT-PCR. Pathol Res Pract. 1994, 190: 1017-25]. Briefly, the RT-PCR reaction is performed on fixed cells by incorporating labeled nucleotides to the PCR reaction. The reaction is carried on using a specific in situ RT-PCR apparatus such as the laser-capture microdissection PixCell I LCM system available from Arcturus Engineering (Mountainview, Calif.).

According to some embodiments of the invention, presence of at least one cervical cell which is identified as a non- or less-differentiated cell according to the method of some embodiments of the invention (e.g., which uses Ficus elastics plant extract, New Fuchsin, Light or Fast green) and at least one cervical cell which exhibits an expression level above a pre-determined threshold of a cervical malignant or of a cervical pre-malignant marker according to the method of some embodiments of the invention (e.g., using an antibody or a polynucleotide probe) in the same cervical cell sample indicates the positive diagnosis of the pre-malignant or the malignant cervical tumor in the subject.

According to some embodiments of the invention, presence of at least one cervical cell having the abnormal morphology according to the method of some embodiments of the invention, at least one cervical cell which is identified as a non- or less-differentiated cell according to the method of some embodiments of the invention (e.g., which uses *Ficus elastics* plant extract, New Fuchsin, Light or Fast green) and at least one cervical cell which exhibits the expression level above the pre-determined threshold of the cervical malignant or of the cervical pre-malignant marker in the same cervical cell sample indicates the positive diagnosis of the pre-malignant or the malignant cervical tumor in the subject.

It should be noted that detecting the expression level of the malignant or pre-malignant cervical cancer marker can be performed on the same cervical cell(s) which are subjected to staining method of the invention (which uses *Ficus elastics* plant extract, New Fuchsin, Light or Fast green), i.e., co-staining.

It should be noted that for co-staining the conditions used for one staining method should be adjusted such that they do not interfere with the staining of the other method. In addition, the dyes used in the two or more staining methods should be selected such that they do not interfere with each other.

Additionally or alternatively, the results of the first staining method can be recorded using an apparatus suitable for dual imaging such as the BioView Duet™ (Bio View, Rehovot, Israel), following which the dye(s) of the first staining method can be removed (using for example, 70% ethanol solution) prior to employing the second staining method on the same cervical cells. It should be noted that such an apparatus enables the user to view staining results of two different staining methods/dyes on the same single cell.

According to some embodiments of the invention, presence of an expression level above the pre-determined threshold of the cervical malignant or of the cervical pre-malignant marker in the same cervical cell which is identified as having a non- or less-differentiated cell based on a red cytoplasm above the pre-determined threshold indicates that the same cell is a cancerous or a pre-malignant cell and thus the positive diagnosis of the pre-malignant or the malignant cervical tumor in the subject.

Additionally or alternatively, detecting the expression level of the malignant or pre-malignant cervical cancer marker can be performed on a parallel cervical cell sample obtained from the same subject, preferably at the same time as the first sample, i.e., parallel staining. The parallel cervical cell sample can be a duplicate slide, obtained at the same time of biopsying the original cervical sample. For example, in case of a cervical smear, the duplicate slide can be prepared from the same brush used to collect the cervical cells of the first slide; in case of a liquid-base sample, the duplicate slide can be obtained from the same aliquot of centrifuged cells; in case of a tissue section, the duplicate slide can be the next slice of tissue (which is only about 5-20 microns apart from the first slice).

According to some embodiments of the invention, viewing and analyzing the staining results (including co-staining, parallel staining or a single staining) is performed using an automated image analysis apparatus with the appropriate analysis software.

Thus, the staining methods of the invention can detect cancerous or pre-cancerous cells in a cervical cell sample and therefore are useful in diagnosing cervical cancer in a subject in need thereof.

As used herein the term "diagnosing" refers to classifying a pathology (e.g., a cervical cancer or a pre-malignant cervical cancer lesion) or a symptom, determining a severity of the pathology (grade or stage), monitoring pathology progression (i.e., without treatment and/or following or during treatment), forecasting an outcome of a pathology and/or prospects of recovery.

According to some embodiments of the invention the method of the invention is used to assist in the diagnosis of cervical cancer, the determination of grading and/or staging of cervical cancer, the monitoring of disease progression, and/or the monitoring and/or evaluation of efficacy of therapy.

As used herein the phrase "subject in need thereof" refers to a female human subject having a routine screening for cervical cancer, as well as to a subject who is at risk of having cervical cancer due to infection with human papilloma virus (HPV), medical and/or family history of cancer, exposure to carcinogens, occupational hazard, environmental hazard, and/or a subject who exhibits suspicious clinical signs of cancer [e.g., vaginal bleeding in menopause females, unexplained pain, sweating, unexplained fever, unexplained loss of weight up to anorexia, anemia and/or general weakness].

Thus, according to an aspect of some embodiments of the invention, there is provided a method of diagnosing a pre-malignant or a malignant cervical tumor in a subject. The method is effected by (a) staining a cervical cell sample of the subject according to the method of the invention, to thereby obtain a stained cervical cell sample, (b) identifying at least one cervical cell of the cervical cell sample having a red cytoplasm above a pre-determined threshold, wherein presence of the at least one cervical cell having the red cytoplasm above the pre-determined threshold is indicative of a non- or less-differentiated cell as compared to a normal cervical cell, thereby diagnosing the pre-malignant or the malignant cervical tumor in the subject.

According to some embodiments of the invention, presence of a non- or less-differentiated cell in the cervical sample is indicative of the diagnosis of a cervical cancer or a pre-malignant cancer in the subject from which the cervical sample was obtained.

As used herein the phrase "pre-malignant cervical tumor" refers to an abnormal growth of cervical cells, which leads to a malignant cervical tumor.

According to some embodiments of the invention, the pre-malignant cervical tumor is grade 1, 2 or 3 of intraepithelial neoplasia (CIN; e.g., CIN1, CIN2 or CIN3), or low, middle or high grade of squamous intraepithelial lesion (SIL; e.g., SIL1, SIL2 or SIL3).

As used herein the phrase "malignant cervical tumor" refers to cancerous tumor of the cervix.

According to some embodiments of the invention, the malignant cervical tumor is carcinoma in situ (which is usually localized to the cervix) or invasive carcinoma (which penetrates to adjacent or distal tissues).

According to some embodiments of the invention, the invasive carcinoma is squamous cell carcinomas (SCC) or adenocarcinoma.

As mentioned, the diagnosis of the cervical cancer or the pre-malignant cervical tumor is performed by analyzing the cervical cell sample which is stained by the staining method of the invention. Such analysis is performed using a microscope (even at low magnification of ×4 for the objective magnification), or a microscope-assisted image analysis system, and is based on the identification of a red color above a pre-determined threshold in the cytoplasm of at least one cervical cell, wherein a presence of at least one cell having a red cytoplasm above a pre-determined threshold is indicative of a non- or less-differentiated cell as compared to a normal cervical cell, whereas presence of non- or less-differentiated cervical cells in the cervical cell sample is indicative of the diagnosis of the pre-malignant or the malignant cervical tumor in the subject.

According to some embodiments of the invention, the diagnosis of the cervical pre-malignant or malignant tumor according to some embodiments of the invention is based on the combination of the differential staining method of the invention and the morphology of the cells which are differentially stained by the method of some embodiments of the invention in the sample. Such a morphological analysis assists and/or enables the determination of staging of the cervical tumor.

Thus, according to some embodiments of the invention, the method of diagnosing the cervical pre-malignant or malignant tumor further comprising analyzing a morphology of the at least one cervical cell having the red cytoplasm above the pre-determined threshold, wherein presence of an abnormal morphology in the same cell having the red cytoplasm above the pre-determined threshold as compared to a morphology of a normal cervical cell is indicative of the pre-malignant or malignant cervical tumor.

Those of skills in the art are capable of determining the staging of the cervical tumors based on the morphological characteristics of the cervical cells.

It should be noted that the combined staining method, i.e., the differential staining method, which uses *Ficus elastics* plant extract, New Fuchsin and Light or Fast green as described above, and which results in identification of non- or less-differentiated cells; and the staining method which identifies expression of cancerous markers on cervical cells can be used to diagnose cervical cancer or cervical pre-malignant cells in the cell sample.

Thus, according to some embodiments of the invention, the method further comprising identifying at least one cervical cell which is identified as being the non- or less-differentiated cell and which also exhibits an expression level above a pre-determined threshold of a cervical malignant or of a cervical pre-malignant marker (i.e., staining of the same cell by the two different staining methods), wherein the at least one cervical cell is a malignant or a pre-malignant cell, thereby diagnosing the pre-malignant or the malignant cervical tumor in the subject.

It should be noted that the combination of staining method as described above, along with analysis of morphologically abnormal cells as described above can be also used in the identification of cervical malignant or pre-malignant cells in the cervical sample.

Thus, according to some embodiments of the invention, the method further comprising identifying at least one cervical cell having the abnormal morphology, which is identified as the non- or less-differentiated cell and which exhibits an expression level above a pre-determined threshold of the cervical malignant or of the cervical pre-malignant marker, wherein the at least one cervical cell is a malignant or a pre-malignant cell, thereby diagnosing the pre-malignant or the malignant cervical tumor in the subject.

According to some embodiments of the invention, presence of an abnormal morphology, an expression level above the pre-determined threshold of the cervical malignant or of the cervical pre-malignant marker and a red cytoplasm above the pre-determined threshold in the same cervical cell indicates the positive diagnosis of the pre-malignant or the malignant cervical tumor in the subject.

Thus, the teachings of the invention can be used to detect cancerous or pre-cancerous cervical cancer cells in a biological sample of the subject and thus be used in diagnosing pre-malignant and/or malignant cervical cancer in a subject.

Once diagnosed with a pre-malignant or a malignant cervical cancer the subject is informed of the possible treatment options, depending on the diagnosis, staging and type of cancer.

According to some embodiments of the invention, the method of diagnosing the cervical pre-malignant or malignant tumor further comprising informing the diagnosis of cervical cancer or a cervical pre-malignant cancer.

It should be noted that the teachings of the invention can be also used to monitor progression of the cervical cancer (e.g., from a localized form to an invasive carcinoma) or the conversion of the pre-malignant cervical cancer to the malignant form.

In addition, the teachings of the invention can be also used to determine a treatment regimen (e.g., whether to treat or not to treat a subject; treat by a surgical resection of tumor, or therapeutic drugs such as chemotherapy) based on the precise diagnosis and staging of the cancer or the pre-malignant cervical tumor.

According to an aspect of some embodiments of the invention there is provided a method of treating a subject having cervical cancer, the method comprising diagnosing the cervical cancer according to the method of some embodiments of the invention and treating the subject based on such diagnosis and/or staging of cervical cancer.

As mentioned, the method of diagnosing a cervical tumor or a pre-malignant cervical tumor can be combined with other known methods of diagnosing cervical cancer such as histological staining (e.g., Papapanicolaou stained cervical smears) and/or molecular techniques [e.g., immunohistochemistry, immunofluorescence or in situ hybridization, such as chromosomal assays (FISH, fluorescent in situ hybridization) or RNA-based in situ hybridization] and thus result in superior diagnostic power and precise staging of the pre-cancerous or cancerous cervical tumors.

The agents of the present invention which are described hereinabove for staining cervical cell samples and/or diagnosing and staging cervical pre-malignant or malignant tumor may be included in a diagnostic kit/article of manufacture preferably along with appropriate instructions for use and labels indicating FDA approval for use in staining cervical cell samples and/or diagnosing and staging cervical pre-malignant or malignant tumor.

Such a kit can include, for example, at least three containers, each including at least one of the above described staining or pre-staining agents (*Ficus elastics* plant extract, New Fuchsin, and Light Green). The kit may also include appropriate buffers and preservatives for improving the shelf-life of the kit.

According to some embodiments of the invention, the kit comprises the *Ficus elastics* plant extract, New Fuchsin, and Light Green.

According to some embodiments of the invention, the kit comprises the *Ficus elastics* plant extract, New Fuchsin, and Fast Green.

The kit further comprising a packaging material for packaging the *Ficus elastics* plant extract, New Fuchsin, and Fast or Light Green.

According to some embodiments of the invention, the kit further comprising instructions for use in staining cervical cell sample and/or diagnosing a cervical pre-malignant or malignant tumor in a subject.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub combination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

Diagnosing Cervical Cancer by Cervical Histology

To establish the feasibility of the staining method according to some embodiments of the invention in detecting cervical cancer in cervical biopsies, optimize staining procedure, establish a correlation of atypical cell morphology with the presence of red color in those atypical cells, optimize and validate the ability of the staining method of some embodiments of the invention to detect cervical cancer and determine the sensitivity of the staining method of some embodiments of the invention to detect cervical cancer, the present inventors have conducted a single center open labeled study. The study was conducted at the Meir Medical Center, Kfar Saba, Israel, and included up to 60 cervical biopsies.

Study Outline

Biopsy samples with known diagnosis were received from Meir medical center pathology department, and transferred to a pathology laboratory to prepare multiple slides from each biopsy. The study is an open label learning and calibration study of cervical biopsies with known pathology, intended for the optimization of the staining procedure and testing its feasibility in detecting cervical cancer.

Procedural Protocol and Sample Processing

The following steps followed for cervical biopsies:

Up to sixty (60) eligible cervical biopsies (archived paraffin blocks) were received (Table 3 below). The diagnosis of each biopsy sample was taken from the subject's file. All biopsy samples were without any identifying information.

Each paraffin block was processed by a pathological laboratory for the preparation of slides for staining.

The slides were stained according to the staining protocol for cervical histological staining as described hereinbelow.

Certain slides were stained according to the current clinical practice of the H&E staining method, when required by study sponsor or study principle investigator to enable a direct comparison to the staining method of the invention.

Staining results were compared to the previously known pathologic results of the samples.

Study Measures

Each slide stained by the staining method of the invention was analyzed as follows:

Cell color—presence of green/blue colored cells (normal cells), red colored cells (potentially cancer cells) or both.

Morphological analysis of the cells in the sample was performed. As noted, an important feature of the staining method of the some embodiments of the invention is that it enables morphological analysis for presence/absence of abnormal cells. Sample was designated as absent of-, or suspected to, contain abnormal or cancer cells.

Alignment of color and cell morphology was performed and recorded to establish a correlation between cell morphology and cell color.

Study endpoints—Correlation of analysis of slides stained by the staining method according to some embodiments of the invention with pathological evaluation as obtained from the stained slides.

Correlation of atypical cell morphology in slides stained by the staining method according to some embodiments of the invention with the presence of the red color in those atypical cells.

In order to determine the correlation of analysis of slides stained by the staining method according to some embodiments of the invention with the pathological evaluation, each sample was defined as 'accurate' or 'non-accurate' by comparing the diagnosis obtained in the staining method according to some embodiments of the invention with the pre-diagnosis of the same sample. The correlation rate is the percent of accurate diagnoses out of the total number of samples.

Materials and Experimental Methods

Equipment—

50 ml plastic tubes, microscope.

Materials—

Cervical histology samples slides and cover slips.

Solutions

Plant extract solution—*Ficus elastics* plant extract in 70% Ethanol [ethanol in water, volume per volume (v/v)].

Light Green solution 4% [weight per volume (w/v)] in 20% Ethanol.

New Fuchsin solution—0.5% (w/v) in 20% Ethanol (v/v).

Hematoxylin Gill III solution—a ready for use solution (Merck, Catalogue No. HX690821).

Ethanol 100% (J. T. Baker, Cat. No. 8006);

Ethanol 96% [96% Ethanol (J. T. Baker, Cat. No. 8006) in double distilled water (DDW)]

Ethanol 50% [50% Ethanol (J. T. Baker, Cat. No. 8006) in double distilled water (DDW)].

Xylen (Bio lab, Cat No 24250505)

Double distillate water (DDW)

Tap water

Eukitt (Sigma Cat No. 03989)

Preparation of *Ficus* Plant Extract:

Selection of Optimized Leaves for the Staining Method—

Optimal leaves for the process are those exhibiting a weight between about 15 and about 25 grams per leaf and a length which is about 18-30 centimeter per leaf as measured from the base of the leaf until the edge. Leaves that were below these specifications (e.g., less than 15 gram per leaf and/or less than 18 centimeter in length) tend to have a red pigment and tend to be over-active from the inhibition point of view, while leaves that are above these criteria (e.g., more than 25 grams per leaf and/or above 30 centimeters in length) are characterized by very strong green pigment and tend to show very little activity.

1 Kg of leaves were cut into 1-2 cm pieces. The cut leaves were mixed with 3 liter of 70% ethanol (EtOH) and were kept for 10 days (room temperature) in a sealed container. Thereafter, the liquid was separated from the solids and kept for further use in room temperature. For optimal purification yields, the liquid was allowed to age in the container for at least 10 days and up to one month at room temperature.

Alternative Preparation of Plant (*Ficus Elastica*) Extract:

Leaves were cut into 1-2 cm pieces. The cut pieces were dried in an oven at 65° C. for 24 hours (hrs). At the beginning, wet content was 80%, while at the end it should have been 4%.

The material was blended into a powder (700-1000 micron). The powder was used in extraction in a reflux system: 1 hour (hr) per extraction, solvent: 70% ethanol, 40° C. Three sequential extractions were performed, each time the powder was re-extracted. Quantity of 70% ethanol in each extraction: first—1:5; second—1:4; third—1:3. The three resulting extracts were mixed, filtered in vacuum filter, paper No. 40. The mixed, filtered extract was evaporated in a rotor evaporator under vacuum at 60° C. until a steady weight was obtained.

The resulting powder (final humidity was 3%) was blended further in a grinder. The powder extract was reconstituted for use as a staining reagent. The powder was taken up in 70% ethanol at a final concentration of 1.3% w/v, pH 7.4. Shelf life of powdered extract: humidity 1%, after six months at room temperature in transparent glass—activity was equivalent to the initial level.

Staining Procedure for Cervical Histological Sections—

Each slide was heated at 70° C. for 15 minutes and then introduced into three containers of 100% Xylen (each filled with about 300 ml) for a 3 minute-incubation in each container. The slides were then transferred into two containers of 100% Ethanol (each filled with about 300 ml) and washed therein by performing about 10 dips (each dip lasts for 1 seconds), followed by a wash (10 dips, each dip lasts for 1 second) in a container filled with 96% Ethanol (ready for use solution). The slides were washed in running distillate water and further incubated for one minute in a Hematoxylin Harris solution (filled within a 50 ml plastic tube), washed with running tap water for 1 minute, followed by a wash in running distillate water for 10 seconds. The slides were then incubated for 4 minutes in the *Ficus elastics* plant extract solution, which was filled within a 50 ml plastic tube. The slides were then washed with running DDW for 10 seconds and further incubated for 2 minutes within New Fuchsin (filled within a 50 ml plastic tube). The slides were washed with running DDW for 10 seconds and incubated for 75 seconds with 50% Ethanol (filled in a 50 ml plastic tube). The slides were then washed with running DDW for 10 seconds and then incubated for 50 seconds with Light Green (filled in a 50 ml plastic tube). The slides were washed with running DDW for 10 seconds and then air-dried for 30 minutes. For microscopical evaluation, the slides were closed with cover slips by the addition of one drop of Eukitt in the middle of sample.

Analysis of Staining—

Cytoplasm of normal cells should be green/blue. Cytoplasm of malignant cells should be red/violet Summary of Proceedings A total of 60 cases, received from the pathology department of Meir MC hospital, were eligible and included in the trial.

All biopsies were processed according to the planned proceedings above. For each case, one slide was stained by Hematoxylin and Eosin (H&E). Multiple slides from each case were prepared to facilitate calibration and optimization of the staining protocol. 6-10 cases were used in the protocol calibration part of the study. This part included a matrix process, by which each step in the protocol was carefully examined and optimized. The purpose of this part was to develop a robust protocol that enables both differential staining and good morphological analysis capabilities. The optimized protocol was then subjected to robust analysis using a few control cases. The following parameters were examined:

Multiple slides processing from the same case on the same day;

Multiple slides processing from the same case on different days;

Independent operators;

The analysis confirmed that the staining protocol according to some embodiments of the invention provides highly repetitive results. Thus, the staining protocol was determined as "sufficient for the clinical trial", and the exact protocol was converted to a Standard Operating Procedure (SOP) format, and thereafter used to stain all samples in the clinical trial.

Procedure of Results Analysis

A detailed analysis report for each case was prepared. The protocol was devised to provide both a detailed description of the professional analysis performed, as well as conclusions of the analysis and comparison to both historical diagnosis and to the parallel stained H&E slide.

Each case [both "H&E stained slide" and "Zetiq stained slide" (a slide stained according to the staining method of some embodiments of the invention)] was first analyzed by Zetiq professional pathologist (Pathologist 1). Following completion of analysis and written report, the slides were transferred to a second, independent, review and analysis, performed by an external expert pathologist (Pathologist 2).

All reports were thoroughly reviewed by Zetiq. The data within the reports were used to compile the results of the clinical trial. A Meta analysis excel table was prepared, and used to analyze the results.

Experimental Results and Analysis of the Clinical Trial

Case Analysis

Table 3, hereinbelow, categorizes the cases into the disease groups as depicted in the clinical protocol.

TABLE 3

Cases categorized according to clinical diagnosis groups

| Historical diagnosis | Number of cases |
| --- | --- |
| Normal | 22 |
| CIN - ⅔ [dysplasia] | 18 |
| SCC [Cancer] | 20 |

Description of samples. CIN = cervical intraepithelial neoplasia; SCC—squamous cell carcinoma. Numbers which follow the "CIN" or "SCC" historical diagnosis represent grading of cancer. Historical diagnosis was based on a biopsy slide stained with H & E.

Table 4, hereinbelow, compiles the data comparing diagnosis of the cervical smear slides based on the results of the staining method of the invention as described herein as compared with the historical diagnosis, which is based on H&E staining.

TABLE 4

Analysis of the staining method of the invention in comparison to historical diagnosis

| Historical diagnosis | % of match (analysis of pathologist 1) | % of match (analysis of Pathologist 2) |
| --- | --- | --- |
| Normal | 95.45[1] | 100 |
| CIN | 100 | 100 |
| SCC | 100 | 80[2] |

Presented are the percentages of success of the staining method of the invention as compared to the historical diagnosis of each case.
[1]In one case, in which the historical diagnosis was normal, the cervical tissue sections was diagnosed as CIN1 by Pathologist 1 after examination of both H&E slide and slide stained according to the staining method of the invention.
[2]Four cases, in which the historical diagnoses were SCC, were diagnosed as CIN3 by Pathologist 2 after examination of both H&E slide and slide stained by the staining method of the invention.

Table 5, hereinbelow, compiles the data comparing diagnostic results of the staining method of the invention to the parallel H&E staining.

TABLE 5

Analysis of the staining method of the invention in comparison to H&E slide diagnosis

| Historical diagnosis | % of success (analysis of pathologist 1) | % of success (analysis of pathologist 2) |
| --- | --- | --- |
| Normal | 100 | 100 |
| CIN | 100 | 100 |
| SCC | 100 | 100 |

From the analysis presented in Table 5 above, it seems that the staining method of some embodiments of the invention is at least as accurate as the currently practiced H&E staining method in diagnosing cervical cancer from tissue biopsies.

Figure 13A:
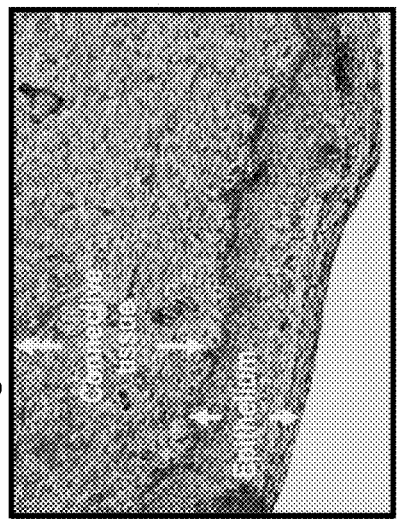
Figure 13B:
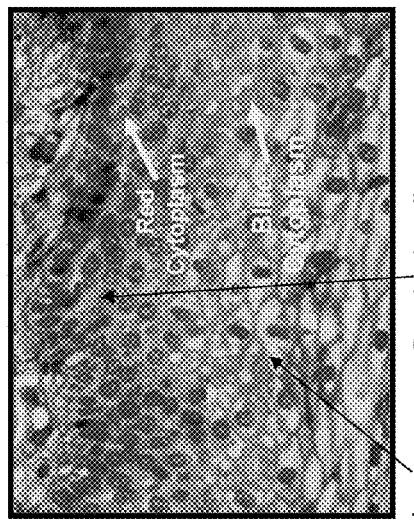

Representative histological sections of this study are shown in FIGS. 1A-B and 8A-D (normal cervix); 12A-D and 13A-D (low-grade CIN1 dysplasia); 2A-B and 11A-D [middle-grade cervical intra-epithelial neoplasia (CIN2)]; 10A-D (high-grade CIN3 dysplasia); and 3A-B and 9A-D [squamous cell carcinoma of cervix]. Thus, while in normal cervix the epithelia cells which are stained according to the staining method of some embodiments of the invention exhibit blue/green cytoplasm (see e.g., FIG. 1A), the neoplastic cells of the cervix neoplasma have reddish-purple cytoplasm in sections stained according to the staining method of the invention (see e.g., FIG. 2A). In contrast, the H&E staining fails to tinctorially distinguish normal from CIN cells (FIG. 2B). Moreover, as shown in FIGS. 13A-B the transition from red (abnormal) to blue (normal) cells enables correct grading of CIN1 dysplasia, which is not easily detected by the H&E staining (FIGS. 13C and D) and can be frequently misdiagnosed. In addition, the malignant cells of the squamous cell carcinoma have uniform reddish cytoplasm in the preparations stained according to the staining method of the invention (FIG. 3A).

Region Analysis

In addition to the analysis of cases, the present inventors have performed analysis of regions. This was made possible, as in most cases there was more than one distinct region for analysis. The analysis was performed by Pathologist 1. In each report, Pathologist 1 carefully marked and analyzed each region, comparing the morphological diagnosis of the region to the color diagnosis. Table 6, hereinbelow, shows the result of this analysis.

TABLE 6

Analysis of slides stained by the method of the invention according to regions

| Morphological Diagnosis | Number of regions | Regions showing normal cells with green cytoplasm (%) | Regions showing normal cells with red cytoplasm (%) | Regions showing atypical cells with green cytoplasm (%) | Regions showing atypical cells with red cytoplasm (%) |
|---|---|---|---|---|---|
| Normal | 47 | 100% | 0% | no cells | no cells |
| CIN 1 | 6 | 100% | 0% | 0% | 100% |
| CIN 2 | 17 | 100% | 0% | 0% | 100% |
| CIN 3 | 23 | no cells | no cells | 0% | 100% |
| SCC | 37 | no cells | no cells | 0% | 100% |

Total number of regions: 130.

Analysis of Match Between Morphology and Color—

The above Tables depict an almost perfect match between the diagnosis of the staining method of the invention to both historical diagnosis as well as the parallel H&E slides. This diagnosis is achieved by combined morphological and color analyses. In a few cases, certain regions showed staining that did not conform with the morphology, as follows:

In certain SCC regions, some cells or sub-regions are stained blue. These cells and sub-regions appear to be well differentiated. This observation does not interfere with the correct diagnosis. In fact, this observation adds credibility to the stain in such that the staining differentiates cells according to their "phenotype".

In 7 regions (of 130 total regions), certain regions or sub regions contained color cell analysis that did not conform to the morphological analysis of these cells/regions. These few (~5% of total regions) observed regions did not alter the overall analysis of the slide, as each region was correctly diagnosed based on morphology, and overall combination of color and morphology in all regions of the case enabled correct diagnosis. There are a few explanations for these observations:

In a few normal regions, the basal layer of the epithelial region is dense. These basal cells have enlarged nuclei that are colored dark red. As little cytoplasm is present in these cells, and as cytoplasm is used to analyze cell color, the region can be classified as red, when in fact the cytoplasm staining is blue. In such instances, careful high magnification analysis is recommended.

Regions located at the edge of the biopsy can be rugged and not well preserved. It seems that in such regions the cells tend to over stain red.

One normal case showing parakeratosis as much red staining occurred due to the large amount of keratin. Keratin is stained bright red by staining method of the invention, and this color can be usually distinguished from the darker red positive staining.

In two CIN2 regions, the "normal" layer above the atypical cell layer was stained red. This could be due to partial over staining, or to the need to conduct high magnification analysis of these regions to locate normal cells stained green, as many times these cells are flattened at the outer layer.

Inter-Observatory Analysis

In one case historical diagnosis was normal. Pathologist 1 diagnosed this case as CIN1, while Pathologist 2 diagnosed this case as normal.

One case historical diagnosis was normal. The staining method of the invention resulted with red staining, which was noted as parakeratosis, as Keratin is mostly stained bright red and can be confused as not normal staining.

Four cases historically diagnosed as SCC, were diagnosed based on the staining method of the invention as CIN3 or SCC.

Conclusions

The study was designed to validate the staining method of some embodiments of the invention and the kit of some embodiments of the invention as an adjunct to the diagnosis of cervical neoplastic processes in cervical biopsies, and show non inferiority compared with conventional staining techniques.

Morphological analysis of cervical biopsy slides stained according to the staining method of the invention is excellent, comparable to H&E staining.

Diagnosis of slides stained according to the staining method of the invention gives exceptional results. When comparing to historical diagnosis there is a 0-4.5% false positives and no false negatives.

A very good (>95%) positive match between color and morphology was found. A few regions showing over red staining in normal cells were described. This over staining can mostly be explained by technical reasons. In all the cases containing these regions, the red staining did not cause misdiagnosis.

Low inter-observatory differences were found. In all but one case, these are attributed to differences between historical and current diagnosis, and are unrelated to the staining method of the invention (i.e., same diagnosis in H&E slide).

SCC regions contain many times cells and regions that alter to a differentiated phenotype. These can be stained blue, and actually lend support to the mechanism of action, correlating the staining method of the invention with the phenotype of the cell.

Correct diagnosis by the staining method of the invention is well achieved, as the stain enables positive diagnosis of borderline cases, and also enables correct differentiation between CIN grades.

In summary, this study clearly shows that diagnosis based on the staining method of the invention as described herein reaches the identical diagnosis made by the current gold standard of staining, while enabling a clear view of morphological features and correct grading of neoplasia.

These results demonstrate that the novel staining method of the invention has an exceptionally high specificity and sensitivity; it offers true dual analysis of color and morphology (offers a clear view of morphological features) for precise diagnosis of cervical cancer; and is superior to currently practiced methods in offering a precise grading method for cervical dysplasia (atypia, but not cancer) and neoplasia (including cancer) based on color discrimination.

The first part of the study entailed calibration and optimization of the staining process towards cervical biopsies, including reproducibility tests. Following completion of this part, a Standard Operating Procedure (SOP) was written and used throughout the remainder of the study.

The main part of the study included staining of all cases using the staining method of the invention and comparison to the current method in use (H&E stain for histological biopsies) according to the diagram depicted in FIG. 19. The study results show 100% concordance of staining method according to some embodiments of the invention based diagnosis with H&E based diagnosis, and a high level of agreement (95-100%) between the pathologists in assigning diagnoses based on the staining method according to some embodiments of the invention. The additional utility parameters of staining method according to some embodiments of the invention resulting from this study are:

Clear morphological visualization;
High degree of matching (correlation) between the color discrimination and morphological based diagnosis;
Ease in identifying regions of early dysplasia (CIN1); and
Precise establishment of grade of dysplasia and simple color differentiation between CIN2 and CIN3 dysplasia.

These important traits are well exemplified in the study slides. Whereas H&E Staining relies solely on morphological visualization using high magnification, staining method according to some embodiments of the invention enables detection, diagnosis & grading of dysplasia (CIN) by following the laminar vertical extent of red/purple cells through the depth of the epithelium, in addition to the classical morpho-cytological criteria.

Example 2

Diagnosis of Cervical Cancer by Staining Conventional Cervical Smears

The study was designed to optimize and validate the ability of staining method of the invention to detect cervical cancer using a cervical smear. The study is an open label learning and calibration study of cervical smears with known pathology, intended for the optimization of the staining procedure and testing its feasibility in detecting cervical cancer.

Materials and Experimental Methods
Cervical smears on microscopical slides.
Protocol of Staining Conventional Cervical Smears:
Slides were washed in 100% Ethanol (EtOH) for 20 minutes, followed by a wash in double distilled water (DDW). Slides were then stained with Hematoxylin (ready for use solution) for 1 minute, rinsed under running Tap water for 2 minutes and washed in DDW for 10 seconds. Slides were then incubated with the *Ficus elastics* plant extract for 4 minutes, washed in DDW and incubated with 0.5% NF (New Fuchsin) in 20% EtOH for 2 minutes. Slides were then washed in DDW for 10 seconds, followed by 20 dips (each dip of slide last for 1 second) in 50% EtOH and washed in DDW for 10 seconds. Slides were then stained with 4% Light Green in 20% EtOH for 5.5 minutes, washed in DDW for 10 seconds and air dried for 30 minutes. Slides were mounted with Eukitt (Sigma Cat No 03989) and closed with cover slips.

Experimental Results
Identification of Squamous Cell Carcinoma in Conventional Cervical Smears—
Cervical smear slides obtained from a subject diagnosed with postmenopausal bleeding were stained as described herein. Another slide from the same patient was stained by the Pap staining method. Analysis of the slide stained by the staining method of the invention revealed discriminative cell staining: the cytoplasm of the cancer cells were stained red, while the cytoplasm of the normal cells including inflammatory cells stained with green. Thus, as shown in FIGS. 4A-D, using staining method of the invention as described herein, cancer cells are easily identifiable, showing bright red even at low magnification such as ×4 (FIG. 4B). In contrast, at such a magnification it is impossible to detect a cancer cell with the Pap staining (FIG. 4D).

These results show that in conventional cytology, used for screening of cervical cancer, the staining method of the invention readily detects the cancer cells amongst normal cell population, providing sensitive and specific color discrimination. These results demonstrate the power of the staining method of the invention to identify a single cancer cell, even at ×4 magnification power.

The Staining Method of the Invention Exhibits a Higher Sensitivity in Detecting Cervical Cancer Using Conventional Cervical Smears as Compared to Currently Practiced Methods—

A pilot cervical conventional cytology on-going study is currently performed in two sites: The Hungarian National Institute of Oncology, and Maccabi HMO in Israel. To date, 64 cases were included in the study. The categorization of the cases according to diagnosis groups is presented in Table 7 below.

TABLE 7

| N | Histological diagnosis |
|---|---|
| 24 | Normal |
| 6 | CIN -1 [early dysplasia] |
| 24 | CIN - ⅔ [moderate to severe dysplasia] |
| 10 | Squamous Cell Carcinoma [SCC, cancer] |

"N" = number of cases in each category.

The result of this study are summarized in the Table 8 below.

TABLE 8

| Specificity | Sensitivity | Staining method |
|---|---|---|
| 85 | 95 | Pap test |
| 85 | 97.5 | staining method according to some embodiments of the invention |
| 24 | 88 | HPV test |

"Pap text" - currently practiced Papanikolaou staining; "HPV test" - human papillomavirus test.

The current data strongly indicates that the diagnosis based on the staining method according to some embodiments of the invention is superior to current methods and shows a significantly increased sensitivity and specificity in comparison to prior art methods.

Example 3

Diagnosis of Cervical Cancer by Staining Liquid Based Slides (Thin-Prep™ Slides) and Comparison to Other Diagnostic Methods This study was designed to validate the staining method and kits of some embodiments of the invention as an adjunct to the diagnosis of cervical neoplastic processes in cervical cytology. This open labeled study was conducted on cervical samples with a known diagnosis, collected at Meir medical center or at Maccabi HMO in Israel. To obtain cervical samples with known diagnosis, subjects were recruited to the study upon visiting the medical facility (e.g., the colposcopy clinic) for follow up examinations following a suspected atypia. This protocol further served to increase the percent of subjects with dysplasia, which are of low prevalence in the general population. Accordingly, the percentage of subjects with dysplasia in this study was high.

The first part of this study entailed calibration and optimization of the staining process towards cervical cell monolayer, including reproducibility tests. FIG. 20 depicts a schematic diagram of the study design. Following completion of this part, a Standard Operating Procedure (SOP) was written and used throughout the remainder of the study. The main part of the study included staining of all cases using the staining method according to some embodiments of the invention and comparison to the current method in use, the H&E stain.

A total of 74 cases were included in the study. The categorization of the cases according to diagnosis groups (made by H&E staining) is presented in the Table 9 below:

TABLE 9

| N | Histological diagnosis |
|---|---|
| 49 | Normal |
| 9 | CIN - 1 [early dysplasia] |
| 16 | CIN - ⅔ [moderate to severe dysplasia] |

"N" - number of cases in each category.

Preparation of Liquid-Base Slides—

Samples were Collected to a Liquid Based preservative (PreserveCyt®, Hologics, USA), and transferred to a pathology laboratory (LEM, Rehovot, ISRAEL), where the liquid samples were processed by a designated device to prepare multiple slides. Briefly, for the preparation of liquid-based slides the cells were collected from the vagina, cervix, and/or cervical canal using a brush and were immediately introduced into a liquid preservative [PreserveCyt®, Hologics, USA) solution, methanol 30-60%, water 40-70%] and were put in the ThinPrep™ machine (Hologics, USA), which filters out the cells from the solution while removing contaminants such as blood and mucus which frequently obscure cells in the traditional cervical smear. The cells were then deposited in a thin and uniform monolayer on glass slides. From each cervical sample one ThinPrep™ slide was stained by the currently practiced Pap staining method, (Papanicolaou staining) while another slide was stained by the staining method of the invention as described hereinbelow.

HPV Testing—

In parallel, aliquots of the liquid samples (prepared using the liquid preservative [PreserveCyt® (Hologics, USA)] as described above were subjected to HPV (human papillomavirus) analysis.

Materials and Experimental Methods

ThinPrep™ slides with cervical cells.

Protocol of Staining Cervical Liquid-Based Slides (ThinPrep™):

Slides were incubated in 10% Trichloroacetic acid (TCA) for 1 hour, washed 4 times with running deionized water from both sides, and then the back of the slide (the side not containing the cervical specimen, cells) was dried on paper towel. The slides were then incubated in Hematoxylin Harris solution for 9 minutes, washed in a jar filled with tap water for 1 minute, washed 4 times in running deionized water from both sides and then the back of the slide was dried on paper towel. The slides were incubated in the *Ficus elastics* plant extract solution for 2 minutes, washed 4 times in running deionized water from both sides and then the back of the slide was dried on paper towel. The slides were incubated in the New Fuchsin solution (0.5% in 20% Ethanol) for 1 minute, washed 4 times with running deionized water from both sides and then the back of the slide was dried on paper towel. The slides were then dipped slowly, 35 times, into 50% Ethanol solution (each dip lasts for 2 seconds), washed 4 times with running deionized water from both sides and then the back of the slide was dried on paper towel. The slides were incubated in the Light Green solution (4% in 20% Ethanol) for 2 minutes, washed 4 times with running deionized water from both sides and then the back of the slide was dried on paper towel. The slides were dipped, 10 times, in 40% Ethanol solution (each dip lasts for 1 second), washed 4 times with running deionized water from both sides and then the back of the slide was dried on paper towel. The slides were dried face down once on a delicate wiper, and air-dried overnight. The slides were closed with cover slip using mounting medium.

Experimental Results

The Staining Method of the Invention Enables Detection of Cervical Cancer at Low Magnification Using Liquid-Based Cervical Monolayers—

FIGS. 5A-D, 6A-F and 7A-F show representative pictures taken from this study, demonstrating the ability of the staining method of the invention to detect cervical cancer from cervical cell monolayer (such as ThinPrep™), even at low magnification such as an Objective magnification of ×4, in which it is impossible to detect cervical cancer or atypical cells using other staining methods such as Pap staining.

The Staining Method of the Invention Provides a Significantly Higher Sensitivity Yet a Comparable Specificity with Respect to Currently Practiced Pap Stain—

74 cases were analyzed. The diagnosis of each subject was made based on by H&E staining of cervical biopsies tissue sections. For each case, the liquid-base slides were stained with the conventional Pap staining and the staining method of the invention as described herein, and were independently analyzed by a pathologist. In parallel, a liquid cervical sample was analyzed by HPV testing. The sensitivity and specificity of the staining method of the invention as compared to those of Pap staining and HPV testing was compared based on the H&E diagnosis. The results are shown in Table 10, hereinbelow.

TABLE 10

| Specificity | Sensitivity | Staining method |
|---|---|---|
| 78% | 80% | Pap test |
| 76% | 90% | Staining method according to some embodiments of the invention |
| 38% | 92% | HPV test |

Analysis of the results reveals that:
The staining method of the invention exhibits a comparable specificity to that of the Pap test, and a much higher specificity as compared to the HPV test.
The staining method of the invention exhibits a greater sensitivity as compared to the Pap test, and similar sensitivity to the HPV test.
All dysplastic cases identified by the Pap test were also identified by the staining method according to some embodiments of the invention; The staining method of the invention correctly identified dysplastic (pre-malignant) cases missed out by the Pap test (Table 10; see the increased sensitivity of the staining method of some embodiments of the invention).

As demonstrated in the study, the staining method of the invention enables simple and reliable detection of Cervical Dysplasia by means of color discrimination at low magnification with concomitant morphological analysis at higher magnification, whereas Pap staining requires high magnification with no color discrepancy resulting in many missed out cases.

This study clearly shows that cytological diagnosis based on the staining method of the invention is superior to current methods (has a sensitivity higher than Pap test and a specificity which is higher than the HPV test), and shows the potential to augment the current drawbacks present in such methods. The staining method of the invention offers a clear view of morphological features, and enables a clear detection of atypical cells based on color discrimination.

It is important to state that the analysis performed when screening for cervical atypia is more stringent. This would explain why in the literature the false negative rates of Pap staining are much larger, on average, by approximately 50%. By using the staining method of the invention, a much lower false negative rate is believed to be achieved in the screening setting. The clear ability for simple detection of atypical cervical cells makes the staining method of the invention an attractive method in screening settings and may reduce the level of expertise required for identification of suspected cervical dysplasia.

In summary, these results show very good sensitivity and specificity of the staining method of the invention in liquid-based cervical monolayer slides such as ThinPrep™ slides. It is clear that the staining method of the invention is superior as compared with conventional staining techniques using the same type of cervical slides.

Example 4

Improved Method of Differentially Staining Cancerous or Pre-Cancerous Cells in Conventional Cervical Smears Following is a non-limiting example of a protocol for staining of cervical smears for detection of cancerous or pre-cancerous cervical cancer cells.

Slides were fixed in a solution of about 10% Trichloroacetic acid (TCA) for one hour. Slides were then washed by running double distilled water (DDW), distilled water (DW) or deionized water for 10 seconds. The slides were stained with Hematoxylin for about 9 minutes and subsequently washed by running tap water for 1 minute and then by running DDW, DW or deionized water for 10 seconds. The slides were incubated with a plant extract solution (Ficus) for about 4 minutes. Following the incubation with the plant extract, the slides were washed by running DDW, DW or deionized water for 10 seconds. The slides were incubated with a New Fuchsin solution [0.25% in 10% ethanol (EtOH)] for 1 minute. Following incubation with New Fuchsin the slides were washed by running DDW, DW or deionized water for 10 seconds and subsequently dipped for about 10 times in 50% EtOH and then washed by running DDW, DW or deionized water for 10 seconds, incubated with a Light Green solution (0.2% in 1% EtOH) and washed by running DDW, DW or deionized water for 10 seconds. The slides were then dipped about 7 times in 40% EtOH, and subsequently washed by running DDW, DW or de-ionized water for 10 seconds. The slides were then air-dried for at least 30 minutes, dipped in 100% Xylene and closed with a cover slip and a mounting medium (Entellan).

Non-limiting examples of cervical cell samples stained according to this protocol are provided in FIGS. 14 [identification of low grade dysplasia cells (LSIL)], 15 [identification of high grade dysplasia cells (HSIL)] and 16 [identification of squamous cell carcinoma (SCC)] using conventional cervical smears.

Example 5

Differential Staining of Cancerous or Pre-Cancerous Cervical Cells Using Fast Green, Ficus Extract and New Fuchsin The following protocol was used for analyzing cervical cells present in a liquid-based sample such as Thin Prep, but can also be used on conventional cervical smears and cervical tissue biopsy.

Slides containing the cervical cells (specimens) were fixed in a solution of 10% Trichloroacetic acid (TCA) for one hour, and washed by running DDW, DW or deionized water for 10 seconds. The slides were then incubated in Hematoxylin (Hematoxylin solution modified according to Gill III for microscopy, or Hematoxylin Harris) for about 9 minutes and washed by running tap water for 1 minute, followed by a further was by running DDW, DW or deionized water for 10 seconds. Following hematoxylin staining, the slides were incubated with the plant extract solution (Ficus) for 4 about minutes (Range from 1 min to 10 min), and then washed by running DDW, DW or deionized water for 10 seconds. The slides were then incubated in the New Fuchsin solution (0.5% in 20% EtOH) for about 1 minute and then washed by running DDW, DW or deionized water for 10 seconds. The slides were then incubated in Fast Green solution (1% in 20% EtOH) for about 45 seconds and washed by running DDW, DW or deionized water for 10 seconds. The slides were then dipped (about 10 times) in a 40% ethanol solution (Range of dips from 5 to 20. Range % of EtOH from 5% to 70%) and subsequently washed by running DDW, DW, or deionized water for 10 seconds. The slides were air dried for at least 30 minutes and then dipped in 100% Xylene. Slides were closed using a cover slip and a mounting medium such as Entellan.

A non-limiting example of a cervical cell sample (liquid-based cervical monolayer) stained according to this protocol is provided in FIG. 17 in which Fast green is used instead of Light green. Note the cluster of high grade dysplasia cells (HSIL) present in the sample. The HSIL cells have red nuclear color, and pink cytoplasm.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method for differential staining a liquid-based cervical monolayer cell sample, the method comprising the steps of:
  (i) incubating a liquid-based cervical monolayer cell sample devoid of blood cells with trichloroacetic acid;
  (ii) contacting the cervical cell sample with a *Ficus elastics* plant extract,
  (iii) staining the cervical cell sample with new fuchsin,
  (iv) staining the cervical cell sample with light green or fast green, and
  (v) staining the cervical cell sample with an agent which differentially stains mucin in the cervical cell sample in a color distinguishable from the color obtained by staining with new fuchsin, light green and fast green to differentially stain the cervical cell sample.

2. A method of diagnosing a pre-malignant or a malignant cervical tumor in a subject, the method comprising the steps of:
  (a) staining a liquid-based cervical monolayer cell sample of the subject according to the method of claim 1, to obtain a stained cervical cell sample,
  (b) identifying at least one cervical cell of said cervical cell sample having a red cytoplasm above a predetermined threshold, wherein a presence of said at least one cervical cell having said red cytoplasm above said predetermined threshold is indicative of a non- or less differentiated cell as compared to a normal cervical cell, thereby diagnosing the pre-malignant or the malignant cervical tumor in the subject.

3. The method of claim 2, further comprising the step of detecting an expression level of a cervical malignant marker or a cervical pre-malignant marker in at least one cervical cell of the cervical cell sample, wherein an expression level above a pre-determined threshold is indicative that said at least one cervical cell is a malignant or a pre-malignant cell, respectively, thereby diagnosing the pre-malignant or the malignant cervical tumor in the subject.

4. The method of claim 3, wherein said cervical malignant or cervical pre-malignant marker is selected from the group consisting of: ki67 antigen (antigen identified by monoclonal antibody Ki-67), Mtn2, Hypoxiainducible factor 1-alpha, Id-1, p161 NK 4a, p21 WAF1/CI P1, Tn antigen, P53 and proliferating cell nuclear antigen.

5. The method of claim 3, further comprising the step of:
  (c) analyzing a morphology of said at least one cervical cell having said red cytoplasm above said pre-determined threshold, wherein a presence of an abnormal morphology in said same cell having said red cytoplasm above said pre-determined threshold as compared to a morphology of a normal cervical cell sample indicates the positive diagnosis of the pre-malignant or the malignant cervical tumor in the subject.

6. The method of claim 1, further comprising the step of:
  (vi) staining the cervical cell sample with hematoxylin.

7. The method of claim 1, further comprising the step of digesting the mucin in the cervical cell sample with an enzyme prior to said staining with new fuchsin.

8. The method of claim 1, further comprising the step of mounting the stained cervical cell sample with amounting medium comprising an anti-oxidant.

9. The method of claim 2, wherein said pre-malignant or malignant cervical tumor is selected from the group consisting of: an intraepithelial neoplasia, a squamous intraepithelial lesion, carcinoma in situ, invasive carcinoma, squamous cell carcinomas and adenocarcinoma.

10. The method of claim 6, wherein said step of staining said cervical cell sample with hematoxylin is effected prior to said step of contacting said cervical cell sample with *Ficus elastics* plant extract.

11. The method of claim 1, wherein said *Ficus elastics* plant extract is selected from the group consisting of: a crude *Ficus elastics* plant extract, a crude ethanol extract of the *Ficus elastics* plant, a crude ethanol extract of the *Ficus elastics* plant, an ethanol extract of leaf tissue of *Ficus elastics* plant and proanthocyanidins.

12. The method of claim 3, wherein said step of detecting the expression level of said cervical malignant or said cervical pre-malignant marker is performed using a high affinity agent selected from the group consisting of: an antibody which specifically binds to said cervical malignant or cervical pre-malignant marker and a polynucleotide.

13. The method of claim 12, wherein said polynucleotide is selected from the group consisting of a polynucleotide which specifically hybridizes to an RNA encoding said cervical malignant or cervical pre-malignant marker and a polynucleotide which specifically amplifies said cervical malignant or cervical pre-malignant marker.

* * * * *